US008846668B2

(12) United States Patent
Himmelsbach et al.

(10) Patent No.: US 8,846,668 B2
(45) Date of Patent: *Sep. 30, 2014

(54) INHIBITORS OF 11BETA-HYDROXYSTEROID DEHYDROGENASE 1

(75) Inventors: Frank Himmelsbach, Mittlelbiberach (DE); Matthias Eckhardt, Biberach (DE); Bradford S. Hamilton, Biberach (DE); Annette Schuler-Metz, Ulm (DE); Linghang Zhuang, Chalfont, PA (US)

(73) Assignees: Vitae Pharmaceuticals, Inc., Fort Washington, PA (US); Boehringer Ingelheim International GmbH (DE)

( * ) Notice: Subject to any disclaimer, the term of this patent is extended or adjusted under 35 U.S.C. 154(b) by 83 days.

This patent is subject to a terminal disclaimer.

(21) Appl. No.: 13/054,954

(22) PCT Filed: Jul. 23, 2009

(86) PCT No.: PCT/EP2009/059509
§ 371 (c)(1),
(2), (4) Date: Feb. 28, 2011

(87) PCT Pub. No.: WO2010/010157
PCT Pub. Date: Jan. 28, 2010

(65) Prior Publication Data
US 2012/0108578 A1    May 3, 2012

Related U.S. Application Data

(60) Provisional application No. 61/135,933, filed on Jul. 25, 2008, provisional application No. 61/206,767, filed on Feb. 4, 2009.

(51) Int. Cl.
*A61K 31/535* (2006.01)
*C07D 413/00* (2006.01)

(52) U.S. Cl.
USPC .......................................... 514/228.8; 544/96

(58) Field of Classification Search
USPC .......................................... 514/228.8; 544/96
See application file for complete search history.

(56) References Cited

U.S. PATENT DOCUMENTS

| | | | |
|---|---|---|---|
| 3,341,538 A | 9/1967 | Block et al. | |
| 3,378,587 A | 4/1968 | Reinhardt | |
| 3,681,349 A | 8/1972 | Schwan et al. | |
| 3,703,529 A | 11/1972 | Frederick et al. | |
| 3,919,047 A | 11/1975 | Vidic et al. | |
| 4,009,171 A | 2/1977 | Albertson | |
| 4,043,927 A | 8/1977 | Duling et al. | |
| 4,108,857 A | 8/1978 | Albertson | |
| 4,136,145 A | 1/1979 | Fuchs et al. | |
| 4,136,162 A | 1/1979 | Fuchs et al. | |
| 4,268,673 A | 5/1981 | Akkerman et al. | |
| 5,089,506 A | 2/1992 | Gray et al. | |
| 5,098,916 A | 3/1992 | Gray et al. | |
| 5,215,992 A | 6/1993 | Gray et al. | |
| 5,393,735 A | 2/1995 | Lange et al. | |
| 5,410,081 A | 4/1995 | Kunde et al. | |
| 5,432,175 A | 7/1995 | Piwinski et al. | |
| 5,480,899 A | 1/1996 | Yano et al. | |
| 5,502,027 A | 3/1996 | Lange et al. | |
| 5,631,209 A | 5/1997 | Lange et al. | |
| 5,776,959 A | 7/1998 | Covey et al. | |
| 5,780,466 A | 7/1998 | Emonds-Alt et al. | |
| 5,811,422 A | 9/1998 | Lam et al. | |
| 5,856,273 A | 1/1999 | Kay et al. | |
| 5,866,702 A | 2/1999 | Mackman et al. | |
| 5,936,124 A | 8/1999 | Hilborn et al. | |
| 5,981,436 A | 11/1999 | Drewes et al. | |
| 6,066,666 A | 5/2000 | Covey et al. | |

(Continued)

FOREIGN PATENT DOCUMENTS

DE          1801556 A1    5/1970
DE        2 105 743 A1    8/1972

(Continued)

OTHER PUBLICATIONS

Claremon et al. CAS: 150:214405, 2009.*
Internatioonal Search Report and Written Opinion for PCT/EP2009/059509 mailed Feb. 9, 2009.
Abstract in English for DE10034623 publication date 2002.
"Khimiia Elementoorganicheskikh Soedineni", 1982, vol. 1982 pp. 22-26.
"Zhurnal Organicheskoi Khimii", 1982, vol. 18, PT 11, p. 2468.
Anderson, (Chem and Biol 10:787-797, 2003).
Bosch et al.: Heterocycles 1980, 14, p. 1983-1988.
CA 1267843-31-1, (Aug. 10, 2009).
CA 154:284276, (Mar. 17, 2011).
Caplus-133:4656—Anantanarayan, A. el. al., "Preparation of heteroarylpyrazoles as P38 kinase inhibitors". 2000.

(Continued)

*Primary Examiner* — Rei-tsang Shiao
(74) *Attorney, Agent, or Firm* — McCarter & English LLP; Steven G. Davis; Michael J. DeGrazia

(57) ABSTRACT

This invention relates to novel compounds of the Formula (I), (Ia$^{1-10}$), (Ib$^{1-10}$), (Ic$^{1-10}$), (Id$^{1-7}$), (Ie$^{1-5}$) pharmaceutically acceptable salts thereof, and pharmaceutical compositions thereof, which are useful for the therapeutic treatment of diseases associated with the modulation or inhibition of 11β-HSD1 in mammals. The invention further relates to pharmaceutical compositions of the novel compounds and methods for their use in the reduction or control of the production of cortisol in a cell or the inhibition of the conversion of cortisone to cortisol in a cell.

(I)

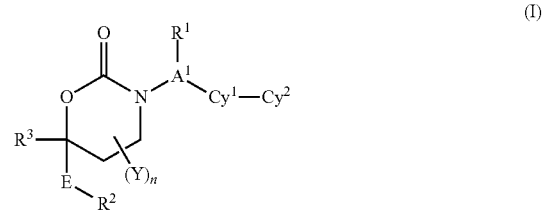

6 Claims, No Drawings

(56) References Cited

U.S. PATENT DOCUMENTS

| | | | |
|---|---|---|---|
| 6,159,990 A | 12/2000 | Lagu et al. |
| 6,242,637 B1 | 6/2001 | Emonds-Alt et al. |
| 6,251,897 B1 | 6/2001 | Ina et al. |
| 6,368,816 B2 | 4/2002 | Walker et al. |
| 6,559,163 B2 | 5/2003 | Cai et al. |
| 6,620,815 B1 | 9/2003 | Lagu et al. |
| 6,635,630 B2 | 10/2003 | Shih et al. |
| 6,638,935 B2 | 10/2003 | Emig et al. |
| 6,653,315 B2 | 11/2003 | Tulshian et al. |
| 6,706,722 B2 | 3/2004 | Emig et al. |
| 6,794,390 B2 | 9/2004 | Lum et al. |
| 6,838,253 B2 | 1/2005 | Walker et al. |
| 6,841,671 B2 | 1/2005 | Noe et al. |
| 6,890,926 B2 | 5/2005 | Emig et al. |
| 6,900,201 B2 | 5/2005 | Noe et al. |
| 6,916,807 B2 | 7/2005 | Freeman-Cook et al. |
| 6,936,615 B2 | 8/2005 | Emig et al. |
| 6,946,487 B2 | 9/2005 | Walker et al. |
| 7,026,310 B2 | 4/2006 | Emig et al. |
| 7,056,912 B2 | 6/2006 | Emig et al. |
| 7,087,400 B2 | 8/2006 | Walker et al. |
| 7,122,531 B2 | 10/2006 | Walker et al. |
| 7,122,532 B2 | 10/2006 | Walker et al. |
| 7,129,231 B2 | 10/2006 | Walker et al. |
| 7,132,551 B2 | 11/2006 | Aquila et al. |
| 7,186,844 B2 | 3/2007 | Ikemoto |
| 7,208,487 B2 | 4/2007 | Bergnes et al. |
| 7,253,198 B2 | 8/2007 | Demont et al. |
| 7,256,005 B2 | 8/2007 | Zitzmann et al. |
| 7,262,212 B2 | 8/2007 | Tsubouchi et al. |
| 7,294,637 B2 | 11/2007 | Aquila et al. |
| 7,417,045 B2 | 8/2008 | Anilkumar et al. |
| 7,566,718 B2 | 7/2009 | Wong et al. |
| 7,652,049 B2 | 1/2010 | Ali et al. |
| 7,897,773 B2 | 3/2011 | Aletru et al. |
| 8,114,868 B2 | 2/2012 | Himmelsbach |
| 8,138,178 B2 | 3/2012 | Claremon et al. |
| 8,202,857 B2 | 6/2012 | Claremon et al. |
| 8,242,111 B2 | 8/2012 | Claremon et al. |
| 8,329,897 B2 | 12/2012 | Xu |
| 8,440,658 B2 | 5/2013 | Claremon et al. |
| 8,569,292 B2 | 10/2013 | Claremon et al. |
| 2001/0039286 A1 | 11/2001 | Dinnell et al. |
| 2006/0063819 A1 | 3/2006 | Lanter et al. |
| 2006/0089349 A1 | 4/2006 | Gundertofte et al. |
| 2006/0116382 A1 | 6/2006 | Yao et al. |
| 2006/0194780 A1 | 8/2006 | Nargund et al. |
| 2006/0276457 A1 | 12/2006 | Yu et al. |
| 2006/0276479 A1 | 12/2006 | Kim et al. |
| 2006/0276480 A1 | 12/2006 | Wong et al. |
| 2007/0021611 A1 | 1/2007 | McGuinness et al. |
| 2007/0054919 A1 | 3/2007 | Rosenblum et al. |
| 2007/0082913 A1 | 4/2007 | Kim et al. |
| 2007/0129345 A1 | 6/2007 | Zhuo et al. |
| 2007/0208001 A1 | 9/2007 | Zhuo et al. |
| 2007/0219182 A1 | 9/2007 | Lubisch et al. |
| 2007/0254875 A1 | 11/2007 | Zhi et al. |
| 2007/0254901 A1 | 11/2007 | Bilodeau et al. |
| 2007/0259891 A1 | 11/2007 | Strobel et al. |
| 2008/0004300 A1 | 1/2008 | Strobel et al. |
| 2008/0021029 A1 | 1/2008 | Strobel et al. |
| 2008/0045518 A1 | 2/2008 | Commons et al. |
| 2008/0045578 A1 | 2/2008 | Commons et al. |
| 2008/0045579 A1 | 2/2008 | Commons et al. |
| 2008/0124384 A1 | 5/2008 | Blum |
| 2008/0188482 A1 | 8/2008 | Rice et al. |
| 2008/0249087 A1 | 10/2008 | Rotstein et al. |
| 2008/0269295 A1 | 10/2008 | Haurand et al. |
| 2008/0280933 A1 | 11/2008 | Efremov et al. |
| 2008/0312271 A1 | 12/2008 | Efremov et al. |
| 2009/0018054 A1 | 1/2009 | Ali et al. |
| 2009/0170894 A1 | 7/2009 | Aletru et al. |
| 2009/0264650 A1 | 10/2009 | Cho et al. |
| 2010/0016164 A1 | 1/2010 | Hino et al. |
| 2010/0025636 A1 | 2/2010 | Gelbin et al. |
| 2010/0041637 A1 | 2/2010 | Claremon et al. |
| 2010/0197675 A1 | 8/2010 | Claremon et al. |
| 2010/0256363 A1 | 10/2010 | Xu |
| 2010/0324045 A1 | 12/2010 | Claremon et al. |
| 2010/0331320 A1 | 12/2010 | Renz et al. |
| 2011/0009402 A1 | 1/2011 | Himmelsbach |
| 2011/0015157 A1* | 1/2011 | Claremon et al. .......... 514/90 |
| 2011/0019643 A1 | 1/2011 | Kim et al. |
| 2011/0021512 A1 | 1/2011 | Claremon et al. |
| 2011/0028445 A1 | 2/2011 | Eckhardt et al. |
| 2011/0034455 A1 | 2/2011 | Claremon et al. |
| 2011/0039286 A1 | 2/2011 | Wu et al. |
| 2011/0053943 A1 | 3/2011 | Claremon et al. |
| 2011/0071139 A1 | 3/2011 | Claremon et al. |
| 2011/0098320 A1 | 4/2011 | Claremon et al. |
| 2011/0105504 A1 | 5/2011 | Claremon et al. |
| 2011/0112062 A1 | 5/2011 | Claremon et al. |
| 2011/0112082 A1 | 5/2011 | Claremon et al. |
| 2011/0124635 A1 | 5/2011 | Claremon et al. |
| 2011/0136800 A1 | 6/2011 | Eckhardt et al. |
| 2011/0136821 A1 | 6/2011 | Claremon et al. |
| 2011/0190262 A1 | 8/2011 | Himmelsbach et al. |
| 2011/0224242 A1 | 9/2011 | Giethlen et al. |
| 2011/0263582 A1 | 10/2011 | Claremon et al. |
| 2011/0263583 A1 | 10/2011 | Claremon et al. |
| 2011/0263584 A1 | 10/2011 | Claremon et al. |
| 2011/0269736 A1 | 11/2011 | Eckhardt et al. |
| 2011/0269791 A1 | 11/2011 | Peters et al. |
| 2011/0269957 A1 | 11/2011 | Fandrick et al. |
| 2011/0275595 A1 | 11/2011 | Eckhardt et al. |
| 2011/0312950 A1 | 12/2011 | Eckhardt et al. |
| 2012/0040973 A1 | 2/2012 | Claremon et al. |
| 2012/0108578 A1 | 5/2012 | Himmelsbach et al. |
| 2012/0108579 A1 | 5/2012 | Renz et al. |
| 2012/0115853 A1 | 5/2012 | Eckhardt et al. |
| 2012/0172357 A1 | 7/2012 | Himmelsbach |
| 2012/0178746 A1 | 7/2012 | Claremon et al. |
| 2012/0184549 A1 | 7/2012 | Himmelsbach |
| 2012/0190675 A1 | 7/2012 | Himmelsbach |
| 2012/0208804 A1 | 8/2012 | Claremon et al. |
| 2012/0232050 A1 | 9/2012 | Claremon et al. |
| 2012/0277149 A1 | 11/2012 | Hamilton et al. |
| 2012/0277455 A1 | 11/2012 | Qu et al. |

FOREIGN PATENT DOCUMENTS

| | | | |
|---|---|---|---|
| DE | 2 108 954 A1 | 9/1972 |
| DE | 2 229 695 A1 | 1/1974 |
| DE | 23 38 369 A1 | 2/1975 |
| DE | 23 54 002 A1 | 5/1975 |
| DE | 2 411 382 A1 | 9/1975 |
| DE | 2 437 610 A1 | 2/1976 |
| DE | 2 828 039 A1 | 1/1980 |
| DE | 19918725 A1 | 10/2000 |
| DE | 19929348 A1 | 12/2000 |
| DE | 10034623 A1 | 1/2002 |
| EP | 0415642 A1 | 3/1991 |
| EP | 0454444 A1 | 10/1991 |
| EP | 0471591 A2 | 2/1992 |
| EP | 0640594 A1 | 3/1995 |
| EP | 0645387 A1 | 3/1995 |
| EP | 0 847 275 A1 | 6/1998 |
| EP | 0928789 A1 | 7/1999 |
| EP | 1156049 A1 | 11/2001 |
| EP | 1270724 A2 | 1/2003 |
| EP | 1801098 A1 | 6/2007 |
| EP | 1852425 A1 | 11/2007 |
| EP | 1 864 971 A1 | 12/2007 |
| EP | 1935420 A1 | 6/2008 |
| GB | 1077711 A | 8/1967 |
| JP | 6092945 A | 4/1994 |
| JP | 7157681 A | 6/1995 |
| JP | 09151179 A | 6/1997 |
| JP | 2002179572 A | 6/2002 |
| JP | 2003096058 A | 4/2003 |
| JP | 2003300884 A | 10/2003 |
| JP | 2005-206503 A | 8/2005 |
| JP | 2005239670 A | 9/2005 |
| JP | 2005272321 A | 10/2005 |

(56) References Cited

FOREIGN PATENT DOCUMENTS

| JP | 2007 140188 A | 6/2007 |
|---|---|---|
| JP | 2007 254409 A | 10/2007 |
| JP | 2009110842 A | 5/2009 |
| JP | 2011519374 A | 7/2011 |
| WO | 92/07838 A1 | 5/1992 |
| WO | 93/07128 A1 | 4/1993 |
| WO | 93/13103 A1 | 7/1993 |
| WO | 95/31440 A1 | 11/1995 |
| WO | 96/14297 A1 | 5/1996 |
| WO | 96/23787 A1 | 8/1996 |
| WO | 96/37494 A1 | 11/1996 |
| WO | 97/07789 A1 | 3/1997 |
| WO | 97/36605 A1 | 10/1997 |
| WO | 98/22462 A1 | 5/1998 |
| WO | 98/57940 A1 | 12/1998 |
| WO | 99/05125 A1 | 2/1999 |
| WO | 99/06395 A1 | 2/1999 |
| WO | WO-0009107 | 2/2000 |
| WO | 01/00595 A1 | 1/2001 |
| WO | WO-0113917 | 3/2001 |
| WO | 01/44200 A2 | 6/2001 |
| WO | 01/55063 A1 | 8/2001 |
| WO | 02/06244 A1 | 1/2002 |
| WO | 02/06277 A1 | 1/2002 |
| WO | 02/22572 A2 | 3/2002 |
| WO | 03/043988 A1 | 5/2003 |
| WO | 03/057673 A1 | 7/2003 |
| WO | 03/093261 A1 | 11/2003 |
| WO | 03/097608 A2 | 11/2003 |
| WO | 2004/004722 A1 | 1/2004 |
| WO | 2004/009559 A2 | 1/2004 |
| WO | 2004/014859 A2 | 2/2004 |
| WO | 2004/046137 A1 | 6/2004 |
| WO | WO-2004056745 | 7/2004 |
| WO | 2004/089896 A1 | 10/2004 |
| WO | 2004/094375 A2 | 11/2004 |
| WO | 2005/000845 A2 | 1/2005 |
| WO | 2005/086700 A2 | 9/2005 |
| WO | 2005/108361 A1 | 11/2005 |
| WO | WO-2005108360 | 11/2005 |
| WO | 2005/113525 A1 | 12/2005 |
| WO | WO-2005116002 | 12/2005 |
| WO | 2006/003494 A2 | 1/2006 |
| WO | WO-2006002349 | 1/2006 |
| WO | 2006/014357 A1 | 2/2006 |
| WO | WO-2006017443 | 2/2006 |
| WO | 2006/024627 A2 | 3/2006 |
| WO | 2006/024628 A1 | 3/2006 |
| WO | 2006/031715 A2 | 3/2006 |
| WO | 2006/040329 A1 | 4/2006 |
| WO | 2006/044174 A2 | 4/2006 |
| WO | 2006/049952 a1 | 5/2006 |
| WO | 2006/066924 A2 | 6/2006 |
| WO | 2006/066948 A1 | 6/2006 |
| WO | 2006/090792 A1 | 8/2006 |
| WO | 2006/104280 A1 | 10/2006 |
| WO | 2006/109056 A1 | 10/2006 |
| WO | 2007/008529 A2 | 1/2007 |
| WO | 2007/022371 A2 | 2/2007 |
| WO | 2007/048595 A1 | 5/2007 |
| WO | 2007/051810 A2 | 5/2007 |
| WO | 2007/061661 A2 | 5/2007 |
| WO | 2007/068330 A1 | 6/2007 |
| WO | 2007/076055 A2 | 7/2007 |
| WO | 2007/079186 A2 | 7/2007 |
| WO | 2007/081569 A2 | 7/2007 |
| WO | 2007/081570 A2 | 7/2007 |
| WO | 2007/081571 A2 | 7/2007 |
| WO | 2007/084314 A2 | 7/2007 |
| WO | 2007/109456 A2 | 9/2007 |
| WO | WO-2007101270 | 9/2007 |
| WO | WO-2007103719 | 9/2007 |
| WO | 2007/118185 A2 | 10/2007 |
| WO | 2007/124254 A2 | 11/2007 |
| WO | 2007/124329 A1 | 11/2007 |
| WO | 2007/124337 A1 | 11/2007 |
| WO | 2007/127763 A2 | 11/2007 |
| WO | 2007123853 A2 | 11/2007 |
| WO | 2007127693 A1 | 11/2007 |
| WO | 2008/000951 A2 | 1/2008 |
| WO | WO-2008024497 | 2/2008 |
| WO | 2008/031227 A1 | 3/2008 |
| WO | 2008/036715 A1 | 3/2008 |
| WO | 2008/046578 A2 | 4/2008 |
| WO | 2008/046758 A2 | 4/2008 |
| WO | 2008/059948 A1 | 5/2008 |
| WO | 2008/106128 A2 | 9/2008 |
| WO | 2008/118332 A2 | 10/2008 |
| WO | 2009/017664 A1 | 2/2009 |
| WO | 2009/017671 A1 | 2/2009 |
| WO | WO-2009020140 | 2/2009 |
| WO | 2009/061498 A1 | 5/2009 |
| WO | 2009/063061 A2 | 5/2009 |
| WO | 2009/075835 A1 | 6/2009 |
| WO | 2009/088997 A1 | 7/2009 |
| WO | 2009/094169 A1 | 7/2009 |
| WO | 2009/100872 A1 | 8/2009 |
| WO | 2009/102428 A2 | 8/2009 |
| WO | 2009/102460 A2 | 8/2009 |
| WO | 2009/107664 A1 | 9/2009 |
| WO | 2009/117109 A1 | 9/2009 |
| WO | WO-2009108332 | 9/2009 |
| WO | WO-2009131669 | 10/2009 |
| WO | 2009/134384 A1 | 11/2009 |
| WO | 2009/134387 A1 | 11/2009 |
| WO | 2009/134392 A1 | 11/2009 |
| WO | 2009/134400 A1 | 11/2009 |
| WO | 2009/138386 A2 | 11/2009 |
| WO | 2010/010149 A1 | 1/2010 |
| WO | 2010/010150 A1 | 1/2010 |
| WO | 2010/010157 A2 | 1/2010 |
| WO | 2010/010174 A1 | 1/2010 |
| WO | 2010/011314 A1 | 1/2010 |
| WO | 2010/023161 A1 | 3/2010 |
| WO | 2010/046445 A2 | 4/2010 |
| WO | 2010/091067 A2 | 8/2010 |
| WO | WO-2010089303 | 8/2010 |
| WO | WO-2010104830 | 9/2010 |
| WO | 2010/127237 A2 | 11/2010 |
| WO | 2010/139673 A1 | 12/2010 |
| WO | WO-2010141424 | 12/2010 |
| WO | WO-2011002910 | 1/2011 |
| WO | WO-2011011123 | 1/2011 |
| WO | WO-2011031979 | 3/2011 |
| WO | 2011/057054 A1 | 5/2011 |
| WO | WO-2011056737 | 5/2011 |
| WO | WO-2011159760 | 12/2011 |
| WO | WO-2011161128 | 12/2011 |
| WO | WO-2012059416 | 5/2012 |

OTHER PUBLICATIONS

Caplus-147:134403, Hembrough, Ta, et al., Composition and methods comprising proteinase activated receptor 2 antagonists for treatment of angiogenesis and inflammatory disorders and cancer. 2007.
Caplus-77:5360, Helsley, G. C. "Antispasmodic 8-carbamoyl-3-phenylnortropanes". 1972.
Chalmers (TIPS vol. 17, pp. 166-172 Apr. 1996).
Chemical Abstracts, Registry No. 351443-37-3 (Available on Aug. 15, 2001.).
Chemical Abstracts, vol. 98, No. 11, 1983, Columbus, Ohio, US; abstract No. 89280k, Lapkin, et al., "Synthesis of 1,3-oxazin-2,4-diones", p. 552 col. 1, XP002504063 abstract.
Chemical Abstracts, vol. 99, No. 23, 1983, Columbus, Ohio, US; abstract No. 195067b, Saitkulova, et al., "Synthesis involving bromozinc alcoholates of carboxylic acid esters", p. 764 col. 1, XP002504064 abstract.
Chimica Therapeutica, 1968, vol. 3(5), pp. 321-324, 1968.
Database CA [Online], Chemical Abstracts Service, Fukushima et al., "Preparation of Imidazolidinone Derivatives as 11.beta.-HSD1 Inhibitors", 2007, XP 002531878.
Database Caplus [Online] Chemical Abstracts Service, Maillard et al., "Spiroheterocyclic Cycloalkane Compounds. II. Synthesis of

(56) References Cited

OTHER PUBLICATIONS

6-Substituted-Tetrahydro-2H-1,3-Oxazine-2-Ones", XP002516521, retrieved from STN Database accession No. 1969:68280 CASRN: 20057-45-8 abstract, (1969).
Database Caplus [Online] Chemical Abstracts Service, Slyusarenko et al., "Synthesis based on Thionylamides.IV. 2-Alkoxy-5,6-Dihydro-1,3-Oxazines", XP002516522, retrieved from STN Database accession No. 1978:563520 CAS RN: 67868-26-2 abstract,(1978).
Database File Registry [Online], Chemical Abstracts Service, Columbus, Ohio, US, 2007, Database accession No. 958599-31-0, Abstract, XP002556900.
Database File Registry [Online], Chemical Abstracts Service, Columbus, Ohio, US, 2007, Database accession No. 958625-83-7, Abstract, XP002556899.
Database File Registry [Online], Chemical Abstracts Service, Columbus, Ohio, US, 2007, Database accession No. 958629-14-6, Abstract, XP002556898.
Database File Registry [Online], Chemical Abstracts Service, Columbus, Ohio, US, 2007, Database accession No. 958629-22-6, Abstract, XP002556897.
Database File Registry [Online], Chemical Abstracts Service, Columbus, Ohio, US, 2007, Database accession No. 958629-39-5, Abstract, XP002556896.
Database File Registry [Online], Chemical Abstracts Service, Columbus, Ohio, US, 2007, Database accession No. 958696-32-7, Abstract, XP002556895.
Database File Registry [Online], Chemical Abstracts Service, Columbus, Ohio, US, 2007, Database accession No. 958696-39-4, Abstract, XP002556894.
Database File Registry [Online], Chemical Abstracts Service, Columbus, Ohio, US, 2007, Database accession No. 958700-63-5, Abstract, XP002556893.
DeMarinis R.M. et.al. Journal of Medicinal Chemistry 1981, vol. 24, No. 12, pp. 1432-1437.
Examiner Interview Summary dated May 2, 2011, in U.S. Appl. No. 12/741,522 (U.S. Patent No. 8,138,178).
Gavezzotti, "Are Crystal Structures Predictable?", Accounts of Chemical Research, 1994, vol. 27, pp. 309-314.
Goubet, et al., "Conversion of a Thiohydantoin to the Corresponding Hydantoin via a Ring-Opening/Ring Closure Mechanism", Tetrahedron Letters, Elsevier, Amsterdam, 1996, vol. 37, pp. 7727-7730.
Gutkowska et al.: Acta Polonaie Pharmaceutica 1987, 39, p. 411-414.
Gutkowska et al.: Acta Poloniae Pharmaceutica 1986, 43, p. 403-405.
Gutkowska et al.: Acta Poloniae Pharmaceutica, 1982, vol. 39, p. 61-64.
Harno et.al. Trends in Endocrinology and Metabolism, Elsevier Science Publishing, New York 2010, vol. 21, No. 10, pp. 619-627.
Ho-Jane Shue et al., "Cyclic Urea Derivatives as Potent NK1 Selective Antagonists", Bioorganic & Medicinal Chemistry Letters, 2005, vol. 15, pp. 3896-3899.
Ho-Jane Shue et al., "Cyclic Urea Derivatives as Potent NK1 Selective Antagonists. Part II: Effects of Fluoro and Benzylic Methyl Substitutions", Bioorganic & Medicinal Chemistry Letters, 2006, vol. 16, pp. 1065-1069.
Hughes, K.A. et al., "11-beta-hydroxysteroid dehydrogenase type 1 (11b-HSD1) inhibitors in Type 2 diabetes mellitus and obesity". Expert Opinion, Investig. Drugs, 17(4), 2008, pp. 481-496.
International Search Report & Written Opinion—(PCT/US2008/002517) Date of Mailing Dec. 29, 2008.
International Search Report & Written Opinion—(PCT/US2008/009017) Date of Mailing Apr. 12, 2008.
International Search Report and Written Opinion for PCT/US2012/050679 mailed Oct. 31, 2012.
International Search Report and Written Opinion—(PCT/US2008/009048) Date of Mailing Dec. 4, 2008.
International Search Report for PCT/EP2009/063913 mailed May 6, 2010.
International Search Report—(PCT/US2008/012618) Date of Mailing Dec. 3, 2009.
International Search Report—(PCT/US2008/013539) Date of Mailing Mar. 19, 2009.
International Search Report—(PCT/US2009/000057) Date of Mailing Mar. 25, 2009.
International Search Report—(PCT/US2009/000421) Date of Mailing Apr. 15, 2009.
International Search Report—(PCT/US2009/000853) Date of Mailing Sep. 2, 2009.
International Search Report—(PCT/US2009/000908) Date of Mailing Sep. 17, 2009.
International Search Report—(PCT/US2009/001712) Date of Mailing Jul. 14, 2009.
International Search Report—(PCT/US2009/002629) Date of Mailing Jul. 3, 2009.
International Search Report—(PCT/US2009/002633) Date of Mailing Jul. 3, 2009.
International Search Report—(PCT/US2009/002641) Date of Mailing Jul. 3, 2009.
International Search Report—(PCT/US2009/002653) Date of Mailing Jul. 3, 2009.
International Search Report—(PCT/US2009/004261) Date of Mailing Oct. 21, 2009.
International Search Report—(PCT/US2010/023021) Date of Mailing Aug. 5, 2010.
Kashima, et al., "Preparation of N-Aryl-2,4-diaminopentanes by the Ring Opening Reaction of 1-Aryl-3,4,5,6-tetrahydro-2-(1H)pyrimidinones", Journal of Heterocyclic Chemistry, vol. 18, 1981, pp. 1595-1596, XP002517485.
Lohray et al., "Enantiospecific Synthesis of 6-Substituted N-Aryl-1,3-Oxazin-2-Ones", Tetrahedron Letters, 1998, vol. 39, pp. 6555-6556.
Ma et al.: Synthesis 2007, p. 161-163.
Ma et al.: Tetrahedron 2007, 63, p. 7523-7531.
Malgorzata Wamil and Jonathan R. Seckl, "Inhibition of 11.beta.-hydroxysteroid Dehydrogenase Type 1 as a Promising Therapeutic Target", Drug Discovery Today, 2007, vol. 12, pp. 504-520.
Morissette et al. Advanced Drug Deliery Reviews 2004, 56, 275-300.
MS Bitar, "Glucocorticoid Dynamics and Impaired Wound Healing in Diabetes Mellitus", Am J Pathol., 1998, vol. 152, pp. 547-554.
MS Bitar, "Insulin and Glucocorticoid-Dependent Suppression of the IGF-I System in Diabetic Wounds", Sugery, 2000, vol. 127, pp. 687-695.
MS Bitar, et al., "Glucocorticoid-Dependent Impairment of Wound Healing in Experimental Diabetes: Amelioration by Adrenalectomy and RU 486", J Surg Res., 1999, vol. 82, pp. 234-243.
MS Bitar, et al., "Heat-Shock Protein 72/73 and Impaired Wound Healing in Diabetic and Hypercortisolemic States", Sugery, 1999, vol. 125, pp. 594-601.
Muehlstadt, et al., "Cyclisation reactions of beta, gamma-unsaturated derivatives of carbonic acid. IX.", Journal Fuer Praktische Chemie, vol. 328, 1986, pp. 163-172, XP002504062 p. 164, compound 4j.
Office Action dated Apr. 3, 2012 for corresponding U.S. Appl. No. 13/318,271.
Office Action dated Jun. 14, 2012 for corresponding U.S. Appl. No. 13/347,784.
Office Action dated May 3, 2012 for corresponding U.S. Appl. No. 13/347,799.
Office Action for U.S. Appl. No. 12/741,522 (U.S. Patent No. 8,138,178), date of mailing Dec. 15, 2010.
Office Action for U.S. Appl. No. 12/741,532 (US Patent No. 8,114,868), date of mailing Dec. 15, 2010.
Office Action for U.S. Appl. No. 12/771,499, date of mailing Dec. 21, 2010.
Olesen et al.: Current Opin Drug Dis Dev, 2001, vol. 4, No. 4, p. 471-478.
Rosenstock et.al. Diabetes Care Jul. 2010, LNKDPUBMED: 20413513, vol. 33, No. 7, pp. 1516-1522.
Schoellkopf, et al., "Umsetzungen Alphametallierter Isocyanide Mit Einigen 1,3-Dipolen//Reactions of Alpha-Metalated Osicyanides with Some 1,3-Dipoles", Liebigs Annalen Der Chemie, Verlag Chemie GMBH. Weinheim, DE, 1980, vol. 4, pp. 600-610.

(56) References Cited

OTHER PUBLICATIONS

Shibata, et al., "Cycloaddition of Oxetanes with Heterocumulenes Catalysed by Organotin Iodine-Lewis Base Complex", Journal of Heterocyclic Chemistry, vol. 24, 1987, pp. 361-363.

Souillac et al., Characterization of Delivery Systems, Differential Scanning Calorimetry, pp. 217-218 (in Encyclopedia of Controlled Drug Delivery, 1999, John Wiley & Sons, pp. 212-227).

Suga, Seiji et al., ""N-Acyliminium Ion Pool" as a Heterodiene in [4+2] Cycloaddition Reaction", Organic Letters, 2003, vol. 5, pp. 945-947.

Suga, Seiji et al., "Cycloaddition of "N-Acyliminium Ion Pools" with Carbon-Carbon Multiple Bonds", Bulletin of the Chemical Society of Japan, Chemical Society of Japan, 2005, vol. 78, pp. 1206-1217.

Sullivan, John M. and Efner, Howard F., "The Preparation of 6-Aryltetrahydro-1,3-oxazin-2-ones and Their Hydrolysis to 3-Substituted Propylamines," The Journal of Organic Chemistry, 33 (5): 2134-2136 (1968).

Taddayon et.al. Expert opinion on Investigational Drugs, Ashley Publication Ltd. 2003, vol. 12, No. 3, pp. 307-324.

Tamaru et al., "Urea as the Most Reactive and Versatile Nitrogen Nucleophile for the Palladium(2+)-Catalyzed Cyclization of Unsaturated Amines", Journal of the American Chemical Society, 1988, vol. 110, pp. 3994-4002.

Thiel (Nature Biotechnol 2:513-519, 2004).

Thornber et al.: Chem Soc Rev, 1979, vol. 8, p. 563-580.

Vidic et al.: Chem. Ber. 1976, 109, p. 2657-2669.

Vippagunta, et al., "Crystalline Solids", Advanced Drug Deliver Reviews, 2001, vol. 48, pp. 3-26.

Wolfling, Janos et al., "Neighboring Group Participation Part 15. Stereoselective Synthesis of Some Steroidal Tetrahydrooxaziin-2-ones, as Novel Presumed Inhibitors of Human 5?-Reductase," Steroids, 69: 451-460 (2004).

Yokoyama et al.: J. Med. Chem. 1979, 22, p. 537-553.

Yoshida, Masaaki et al., "Selective synthesis of five- and six-membered cyclic carbamates by the reaction of 2-(1-haloalkyl)oxiranes with carbon dioxide and aliphatic primary amines", Heterocycles, Elsevier Science Ltd., 1993, vol. 35 (2), pp. 623-626.

Yoshinao Tamaru, "Palladium(2+)-Catalyzed Intramolecular Aminocarbonylation of 3-Hydroxy-4-pentenylamines and 4-Hydroxy-5-hexenylamines", J. Org. Chem., 1988, pp. 5731-5741.

Zhurnal Organicheskoi Khimii, 1978, vol. 14(5), pp. 1092-1094.

Donohoe, T.J. et al., "Stereoselectivity in the double reductive alkylation of pyrroles: synthesis of cis-3,4-disubstituted pyrrolidines". Chemical Communications, vol. 1999, No. 2, Feb. 1, 1999, p. 141-142.

Evans, B.E. et al., "Orally active, nonpeptide osytocin antagonists". Journal of Medicinal Chemistry, American Chem. Soc., Vo. 35, No. 21, Oct. 15, 1992, p. 3919-3927.

Tamaru, Y. et al., "Palladium (2+)-Catalyzed Intramolecular Aminocarbonylation of 3-Hydroxy-4-pentenylamines and 4-Hydroxy-5-hexenylamines". Journal Organic Chemistry, vol. 53, No. 24, 1988, p. 5731-5741.

Aluri. B.R. et al., "Bulky n-Substituted 1,3-Benzazaphospholes: Access via Pd-Catalyzed C-N and C-P Cross Coupling, Lithiation, and Conversion to Novel P=C PtBu2 Hybrid Ligands". Inorganic Chemistry, 2008, 47, p. 6900-6912.

Aluri, B.R. et al., "Sterically and Polarity-Controlled Reactions of tBuLi with P=CH—NR Heterocycles: Novel Heterocyclic P-and P,O-Ligands and Preliminary Tests in Transition-Metal Catalysis", Chem. Eur. Journal, vol. 14, 2008, p. 4328-4335.

Fandrick, Dr. et al., "Copper Catalyzed Asymmetric Propargylation of Aldehydes". JACS Communications, Published on Web May 18, 2010, J. Am. Chem. Soc., vol. 132, No. 22, 2010, p. 7600,7601.

International Search Report and Written Opinion for PCT/EP/2009/059496 mailed Nov. 17, 2009.

International Search Report and Written Opinion for PCT/EP2010/051262 mailed Aug. 7, 2011.

International Search Report and Written Opinion for PCT/EP2011/060386 mailed Sep. 15, 2011.

International Search Report and Written Opinion for PCT/US2010/054912 mailed Mar. 16, 2011.

International Search Report for PCT/EP2011/068938 mailed Mar. 27, 2012.

Lightburn, T.E. et al., "Catalytic Scaffolding Ligands: An Efficient Strategy for Direction Reactions". JACS Communications, Published on Web May 25, 2008, Journal American Chem. Soc., vol. 130, No. 29, 2008, p. 9210-9211.

Senanayake, C. Presentation: "Timely Chemical Process Research is a Critical Part for Efficient Drug Development". 4th Siegfried Symposium, Sep. 23, 2010, p. 1-91, Retrieved from internet: URL: http://www.siegfried/ch/fileadmin/User2/Bilder/Fotogalerien/Symposium_2010/Award_Talk_Senanayake.pdf. Retrieved on Feb. 23, 2010.

Tang, W. et al., "Novel and Efficient Chiral Bisphosphorus Ligands for Rhodium-Catalyzed Asymmetric Hydrogenation". Organic Letters, 2010, vol. 12, No. 5, p. 1104-1107.

Tang, W. et al., "Novel, Tunable, and Efficient Chiral Bisdihydrobenzooxaphosphole Ligands for Asymmetric Hydrogenation". Organic Letters, 2010, vol. 12, No. 1., p. 176-179.

Worthy, AD. et al., "Regioselective Hydroformylation of Sulfonamides using a Scaffolding Ligand". Organic Letters, 2009, vol. 11, No. 13—p. 2764-2767.

Kametani et al. Chem Pharma Bull, 1965 vol. 13, No. 3, p. 295-299.

Patani et al. Chem Rev, 1996 p. 3147-3176.

Stewart et al. *Vitam Horm*. 1999;57:249-324.

\* cited by examiner

INHIBITORS OF 11BETA-HYDROXYSTEROID DEHYDROGENASE 1

FIELD OF THE INVENTION

The present invention relates to inhibitors of 11β-hydroxysteroid dehydrogenase type 1 (11β-HSD1), pharmaceutical compositions thereof and methods of using the same.

BACKGROUND OF THE INVENTION

Glucocorticoids, such as cortisol (hydrocortisone), are steroid hormones that regulate fat metabolism, function and distribution, and play a role in carbohydrate, protein and fat metabolism. Glucocorticoids are also known to have physiological effects on development, neurobiology, inflammation, blood pressure, metabolism, and programmed cell death. Cortisol and other corticosteroids bind both the glucocorticoid receptor (GR) and the mineralocorticoid receptor (MR), which are members of the nuclear hormone receptor superfamily and have been shown to mediate cortisol function in vivo. These receptors directly modulate transcription via DNA-binding zinc finger domains and transcriptional activation domains.

Until recently, the major determinants of glucocorticoid action were attributed to three primary factors: (1) circulating levels of glucocorticoid (driven primarily by the hypothalamic-pituitary-adrenal (HPA) axis); (2) protein binding of glucocorticoids in circulation; and (3) intracellular receptor density inside target tissues. Recently, a fourth determinant of glucocorticoid function has been identified: tissue-specific pre-receptor metabolism by glucocorticoid-activating and -inactivating enzymes. These 11β-hydroxysteroid dehydrogenase (11β-HSD) pre-receptor control enzymes modulate activation of GR and MR by regulation of glucocorticoid hormones. To date, two distinct isozymes of 11-beta-HSD have been cloned and characterized: 11β-HSD1 (also known as 11-beta-HSD type 1, 11betaHSD1, HSD11B1, HDL, and HSD11L) and 11β-HSD2. 11β-HSD1 is a bi-directional oxidoreductase that regenerates active cortisol from inactive 11-keto forms, whereas 11β-HSD2 is a unidirectional dehydrogenase that inactivates biologically active cortisol by converting it into cortisone.

The two isoforms are expressed in a distinct tissue-specific fashion, consistent with the differences in their physiological roles. 11β-HSD1 is widely distributed in rat and human tissues; expression of the enzyme and corresponding mRNA have been detected in human liver, adipose tissue, lung, testis, bone and ciliary epithelium. In adipose tissue, increased cortisol concentrations stimulate adipocyte differentiation and may play a role in promoting visceral obesity. In the eye, 11β-HSD1 may regulate intraocular pressure and may contribute to glaucoma; some data suggest that inhibition of 11β-HSD1 may cause a drop in intraocular pressure in patients with intraocular hypertension (Kotelevstev et al. (1997), Proc. Natl. Acad. Sci. USA 94(26):14924-9). Although 11β-HSD1 catalyzes both 11-beta-dehydrogenation and the reverse 11-oxoreduction reaction, 11β-HSD1 acts predominantly as a NADPH-dependent oxoreductase in intact cells and tissues, catalyzing the formation of active cortisol from inert cortisone (Low et al. (1994) J. Mol. Endocrin. 13: 167-174). In contradistinction, 11β-HSD2 expression is found mainly in mineralocorticoid target tissues such as kidney (cortex and medulla), placenta, sigmoid and rectal colon, salivary gland and colonic epithelial cell lines. 11β-HSD2 acts as an NAD-dependent dehydrogenase catalyzing the inactivation of cortisol to cortisone (Albiston et al. (1994) Mol. Cell. Endocrin. 105: R11-R17), and has been shown to protect the MR from glucocorticoid excess (e.g., high levels of receptor-active cortisol) (Blum, et al. (2003) Prog. Nucl. Acid Res. Mol. Biol. 75:173-216).

Mutations in either the 11β-HSD1 or the 11β-HSD2 genes result in human pathology. For example, individuals with mutations in 11β-HSD2 are deficient in this cortisol-inactivation activity and, as a result, present with a syndrome of apparent mineralocorticoid excess (also referred to as 'SAME') characterized by hypertension, hypokalemia, and sodium retention (Edwards et al. (1988) Lancet 2: 986-989; Wilson et al. (1998) Proc. Natl. Acad. Sci. 95: 10200-10205). Similarly, mutations in 11β-HSD1 and in the gene encoding a co-localized NADPH-generating enzyme, hexose 6-phosphate dehydrogenase (H6PD), can result in cortisone reductase deficiency (CRD); these individuals present with ACTH-mediated androgen excess (hirsutism, menstrual irregularity, hyperandrogenism), a phenotype resembling polycystic ovary syndrome (PCOS) (Draper et al. (2003) Nat. Genet. 34: 434-439).

Notably, disruption of homeostasis in the HPA axis by either deficient or excess secretion or action results in Cushing's syndrome or Addison's disease, respectively (Miller and Chrousos (2001) Endocrinology and Metabolism, eds. Felig and Frohman (McGraw-Hill, New York), $4^{th}$ Ed.: 387-524). Patients with Cushing's syndrome or receiving glucocorticoid therapy develop reversible visceral fat obesity. The phenotype of Cushing's syndrome patients closely resembles that of Reaven's metabolic syndrome (also known as Syndrome X or insulin resistance syndrome), the symptoms of which include visceral obesity, glucose intolerance, insulin resistance, hypertension, type 2 diabetes and hyperlipidemia (Reaven (1993) Ann Rev. Med. 44: 121-131). Although the role of glucocorticoids in human obesity is not fully characterized, there is mounting evidence that 11β-HSD1 activity plays an important role in obesity and metabolic syndrome (Bujalska et al. (1997) Lancet 349: 1210-1213); (Livingstone et al. (2000) Endocrinology 131: 560-563; Rask et al. (2001) J. Clin. Endocrinol. Metab. 86: 1418-1421; Lindsay et al. (2003) J. Clin. Endocrinol. Metab. 88: 2738-2744; Wake et al. (2003) J. Clin. Endocrinol. Metab. 88: 3983-3988).

Data from studies in mouse transgenic models supports the hypothesis that adipocyte 11β-HSD1 activity plays a central role in visceral obesity and metabolic syndrome (Alberts et al. (2002) Diabetologia. 45(11): 1526-32). Over-expression in adipose tissue of 11β-HSD1 under the control of the aP2 promoter in transgenic mice produced a phenotype remarkably similar to human metabolic syndrome (Masuzaki et al. (2001) Science 294: 2166-2170; Masuzaki et al. (2003) J. Clinical Invest. 112: 83-90). Moreover, the increased activity of 11β-HSD1 in these mice is very similar to that observed in human obesity (Rask et al. (2001) J. Clin. Endocrinol. Metab. 86: 1418-1421). In addition, data from studies with 11β-HSD1-deficient mice produced by homologous recombination demonstrate that the loss of 11β-HSD1 leads to an increase in insulin sensitivity and glucose tolerance due to a tissue-specific deficiency in active glucocorticoid levels (Kotelevstev et al. (1997) Proc. Natl. Acad. Sci. 94: 14924-14929; Morton et al. (2001) J. Biol. Chem. 276: 41293-41300; Morton et al. (2004) Diabetes 53: 931-938).

The published data supports the hypothesis that increased expression of 11≈-HSD1 contributes to increased local conversion of cortisone to cortisol in adipose tissue and hence that 11β-HSD1 plays a role in the pathogenesis of central obesity and the appearance of the metabolic syndrome in humans (Engeli, et al., (2004) Obes. Res. 12: 9-17). Therefore, 11β-HSD1 is a promising pharmaceutical target for the treatment of the metabolic syndrome (Masuzaki, et al., (2003) Curr. Drug Targets Immune Endocr. Metabol. Disord. 3: 255-62). Furthermore, inhibition of 1113-HSD1 activity may prove beneficial in treating numerous glucocorticoid-related disorders. For example, 11β-HSD1 inhibitors could be effective in combating obesity and/or aspects of the metabolic syndrome cluster, including glucose intolerance, insulin resistance, hyperglycemia, hypertension, and/or hyperlipidemia (Kotelevstev et al. (1997) Proc. Natl. Acad. Sci. 94: 14924-14929; Morton et al. (2001) J. Biol. Chem. 276: 41293-41300; Morton et al. (2004) Diabetes 53: 931-938). In addition, inhibition of 11β-HSD1 activity may have beneficial effects on the pancreas, including the enhancement of glucose-stimulated insulin release (Billaudel and Sutter (1979) Horm. Metab. Res. 11: 555-560; Ogawa et al. (1992) J. Clin. Invest. 90: 497-504; Davani et al. (2000) J. Biol. Chem. 275: 34841-34844).

Furthermore, given that inter-individual differences in general cognitive function have been linked to variability in the long-term exposure to glucocorticoids (Lupien et al. (1998) Nat. Neurosci. 1: 69-73) and dysregulation of the HPA axis resulting in chronic exposure to glucocorticoid excess in certain brain subregions has been theorized to contribute to the decline of cognitive function (McEwen and Sapolsky (1995) Curr. Opin. Neurobiol. 5: 205-216), one might predict that inhibition of 11β-HSD1 could reduce exposure to glucocorticoids in the brain and thereby protect against deleterious glucocorticoid effects on neuronal function, including cognitive impairment, dementia, and/or depression. Notably, it is known that stress and glucocorticoids influence cognitive function (de Quervain et al. (1998) Nature 394: 787-790); and it has been shown that 11β-HSD1, through its control of glucocorticoid action in the brain, may have effects on neurotoxicity (Rajan et al. (1996) Neuroscience 16: 65-70; Seckl (2000) Neuroendocrinol. 18:49-99).

There is also evidence that glucocorticoids and 11β-HSD1 play a role in regulation of in intra-ocular pressure (IOP) (Stokes et al. (2000) Invest. Ophthalmol. Vis. Sci. 41: 1629-1683; Rauz et al. (2001) Invest. Ophthalmol. Vis. Sci. 42: 2037-2042); if left untreated, elevated IOP can lead to partial visual field loss and eventually blindness. Thus, inhibition of 11β-HSD1 in the eye could reduce local glucocorticoid concentrations and IOP, and 11β-HSD1 hence could potentially be used to treat glaucoma and other visual disorders.

Transgenic aP2-11βHSD1 mice exhibit high arterial blood pressure and have increased sensitivity to dietary salt. Moreover, plasma angiotensinogen levels are elevated in the transgenic mice, as are angiotensin II and aldosterone; and treatment of the mice with an angiotensin II antagonist alleviates the hypertension (Masuzaki et al. (2003) J. Clinical Invest. 112: 83-90). This suggests that hypertension may be caused or exacerbated by 11β-HSD1 activity. Thus, 11β-HSD1 inhibitors may be useful for treatment of hypertension and hypertension-related cardiovascular disorders Inhibition of 11β-HSD1 in mature adipocytes is also expected to attenuate secretion of plasminogen activator inhibitor 1 (PAI-1), which is an independent cardiovascular risk factor (Halleux et al. (1999) J. Clin. Endocrinol. Metabl. 84: 4097-4105).

Glucocorticoids can have adverse effects on skeletal tissues; and prolonged exposure to even moderate glucocorticoid doses can result in osteoporosis (Cannalis (1996) J. Clin. Endocrinol. Metab. 81: 3441-3447). In addition, 11β-HSD1 has been shown to be present in cultures of human primary osteoblasts as well as cells from adult bone (Cooper et al. (2000) Bone 27: 375-381), and the 11β-HSD1 inhibitor carbenoxolone has been shown to attenuate the negative effects of glucocorticoids on bone nodule formation (Bellows et al. (1998) Bone 23: 119-125). Thus, inhibition of 11β-HSD1 is predicted to decrease the local glucocorticoid concentration within osteoblasts and osteoclasts, thereby producing beneficial effects in various forms of bone disease, including osteoporosis.

11β-HSD1 inhibitors may also be useful for immunomodulation. Although glucocorticoids are perceived to suppress the immune system, in actuality, there is a complex, dynamic interaction between the HPA axis and the immune system (Rook (1999) Baillier's Clin. Endocrinol. Metabl. 13: 576-581). Glucocorticoids play a role in modulating the balance between cell-mediated and humoral immune response, with high glucocorticoid activity normally associated with a humoral response Inhibition of 11β-HSD1 therefore can be used a means of shifting the immune response towards a cell-mediated response. Certain disease states, such as tuberculosis, leprosy (Hansen's disease) and psoriasis, trigger immune responses that are biased towards a humoral response whereas the more effective immune response may be a cell-mediated response. Hence, 11β-HSD1 inhibitors may be useful for treating such diseases.

It has been reported that glucocorticoids inhibit wound healing, especially in diabetic patients with ulcers (Bitar et al. (1999) J. Surg. Res. 82: 234-243; Bitar et al. (1999) Surgery 125: 594-601; Bitar (2000) Surgery 127: 687-695; Bitar (1998) Am. J. Pathol. 152: 547-554). Patients that exhibit impaired glucose tolerance and/or type 2 diabetes often also have impaired wound healing. Glucocorticoids have been shown to increase the risk of infection and delay wound healing (Anstead (1998) Adv. Wound Care 11:277-285). Moreover, there is a correlation between elevated levels of cortisol in wound fluid and non-healing wounds (EP Patent App. No. 0 902 288). Recent published patent applications have suggested that certain 11β-HSD1 inhibitors may be useful for promoting wound healing (PCT/US2006/043, 951).

As evidenced herein, there is a continuing need for new and improved drugs that inhibit 11β-HSD1. The novel compounds of the instant invention are effective inhibitors of 11β-HSD1.

SUMMARY OF THE INVENTION

It has now been found that compounds of Formula I or pharmaceutically acceptable salts or prodrugs thereof, are effective inhibitors of 11β-HSD1. In a first embodiment, the invention is a compound represented by Formula I:

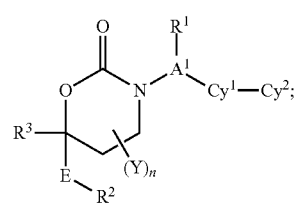

wherein variables are defined herein as follows:
$R^1$ is (a) absent or (b) is selected from $(C_1-C_6)$alkyl, $(C_1-C_6)$ cycloalkyl, $(C_2-C_6)$alkenyl, $(C_2-C_6)$alkynyl, $(C_1-C_3)$ alkoxy$(C_1-C_3)$alkoxy, or $(C_1-C_3)$alkoxy$(C_1-C_3)$alkyl and is optionally substituted with up to four groups independently selected from fluorine, cyano, oxo, $R^4$, $R^4O—$, $(R^4)_2N—$, $R^4O_2C—$, $R^4S$, $R^4S(=O)—$, $R^4S(=O)_2—$, $R^4C(=O)NR^4—$, $(R^4)_2NC(=O)—$, $(R^4)_2NC(=O)O—$, $(R^4)_2NC(=O)NR^4$—, $R^4OC(=O)NR^4$—, $(R^4)_2NC(=NCN)NR^4$—, $(R^4O)_2P(=O)O$—, $(R^4O)_2P(=O)NR^4$—, $R^4OS(=O)_2NR^4$—, $(R^4)_2NS(=O)_2O$—, $(R^4)_2NS(=O)_2NR^4$—, $R^4S(=O)_2NR^4$—, $R^4S(=O)_2NHC(=O)$—, $R^4S(=O)_2NHC(=O)O$—, $R^4S(=O)_2NHC(=O)NR^4$—, $R^4OS(=O)_2NHC(=O)$—, $R^4OS(=O)_2NHC(=O)O$—, $R^4OS(=O)_2NHC(=O)NR^4$—, $(R^4)_2NS(=O)_2NHC(=O)$—, $(R^4)_2NS(=O)_2NHC(=O)O$—, $(R^4)_2NS(=O)_2NHC(=O)NR^4$—, $R^4C(=O)NHS(=O)_2$—, $R^4C(=O)NHS(=O)_2O$—, $R^4C(=O)NHS(=O)_2NR^4$—, $R^4OC(=O)NHS(=O)_2$—, $R^4OC(=O)NHS(=O)_2O$—, $R^4OC(=O)NHS(=O)_2NR^4$—, $(R^4)_2NC(=O)NHS(=O)_2$—, $(R^4)_2NC(=O)NHS(=O)_2O$—, $(R^4)_2NC(=O)NHS(=O)_2NR^4$—, heterocyclyl, heteroaryl, arylamino and heteroarylamino;

$A^1$ is (a) a bond, or (b) $(C_1-C_3)$alkylene, $CH_2CH_2O$, wherein the oxygen is attached to $Cy^1$, or $CH_2C(=O)$, wherein the carbonyl carbon is attached to $Cy^1$;

$Cy^1$ is aryl, heteroaryl, monocyclic cycloalkyl or monocyclic heterocyclyl and is optionally substituted with 1 to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkylalkylthio, halo$(C_1-C_6)$alkylthio, halo$(C_3-C_6)$cycloalkythio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cycloalkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclylsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxy, $(C_1-C_6)$alkylcarbonyl, $(C_3-C_6)$cycloalkylcarbonyl, $(C_3-C_6)$cycloalkylaminocarbonyl, {$(C_3-C_6)$cycloalkyl}{$(C_1-C_6)$alkyl}aminocarbonyl, di$(C_3-C_6)$cycloalkylaminocarbonyl, $(C_3-C_6)$cycloalkylaminosulfonyl, {$(C_3-C_6)$cycloalkyl}{$(C_1-C_6)$alkyl}aminosulfonyl, di$(C_3-C_6)$cycloalkylaminosulfonyl, cyano$(C_1-C_6)$alkyl, aminocarbonyl$(C_1-C_6)$alkyl, $(C_1-C_6)$alkylaminocarbonyl$(C_1-C_6)$alkyl, di$(C_1-C_6)$alkylaminocarbonyl$(C_1-C_6)$alkyl, $(C_3-C_6)$cycloalkylaminocarbonyl$(C_1-C_6)$alkyl, {$(C_3-C_6)$cycloalkyl}{$(C_1-C_6)$alkyl}aminocarbonyl$(C_1-C_6)$alkyl and di$(C_3-C_6)$cycloalkylaminocarbonyl$(C_1-C_6)$alkyl;

$Cy^2$ is benzimidazolyl, benzotriazolyl and piperidinyl and is optionally substituted with 1 to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkylalkylthio, halo$(C_1-C_6)$alkylthio, halo$(C_3-C_6)$cycloalkythio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cycloalkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclylsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkylamino$(C_2-C_6)$alkoxy, $(C_1-C_6)$alkylamino$(C_2-C_6)$alkoxy, di$(C_1-C_6)$alkylamino$(C_2-C_6)$alkoxy, $(C_1-C_6)$alkylcarbonyl, hydroxy$(C_1-C_6)$alkylcarbonyl, $(C_3-C_6)$cycloalkylcarbonyl, $(C_3-C_6)$cycloalkylaminocarbonyl, {$(C_3-C_6)$cycloalkyl}{$(C_1-C_6)$alkyl}aminocarbonyl, di$(C_3-C_6)$cycloalkylaminocarbonyl, $(C_3-C_6)$cycloalkylaminosulfonyl, {$(C_3-C_6)$cycloalkyl}{$(C_1-C_6)$alkyl}aminosulfonyl, di$(C_3-C_6)$cycloalkylaminosulfonyl, cyano$(C_1-C_6)$alkyl, aminocarbonyl$(C_1-C_6)$alkyl, $(C_1-C_6)$alkylaminocarbonyl$(C_1-C_6)$alkyl, di$(C_1-C_6)$alkylaminocarbonyl$(C_1-C_6)$alkyl, $(C_3-C_6)$cycloalkylaminocarbonyl$(C_1-C_6)$alkyl, {$(C_3-C_6)$cycloalkyl}{$(C_1-C_6)$alkyl}aminocarbonyl$(C_1-C_6)$alkyl and di$(C_3-C_6)$cycloalkylaminocarbonyl$(C_1-C_6)$alkyl; wherein the piperidinyl represented by $Cy^1$ is attached to $Cy^1$ through a ring carbon atom. In another embodiment, when $Cy^2$ is piperidinyl, oxo is also a possible substituent.

Alternatively, when $R^3$ is methoxymethyl, $Cy^2$ is (a) halogen or —O—$SO_3$—R or (b) cycloalkyl, aryl, heterocyclyl or heteroaryl, optionally substituted with 1 to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_3-C_7)$cycloalkyl$(C_1-C_2)$alkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_3-C_7)$cycloalkyl$(C_1-C_2)$alkyl, $(C_1-C_6)$alkoxy, $(C_3-C_6)$cycloalkoxy, $(C_3-C_7)$cycloalkyl$(C_1-C_2)$alkoxy, halo$(C_1-C_6)$alkoxy, halo$(C_3-C_6)$cyclo alkoxy, halo$(C_3-C_7)$cyclo alkyl$(C_1-C_2)$alkoxy, $(C_1-C_6)$alkylthio, $(C_3-C_6)$cycloalkythio, $(C_3-C_7)$cycloalkyl$(C_1-C_2)$alkylthio, halo$(C_1-C_6)$alkylthio, halo($C_3$-$C_6$)cycloalkythio, halo($C_3$-$C_7$)cycloalkyl($C_1$-$C_2$) alkylthio, ($C_1$-$C_6$)alkanesulfinyl, ($C_3$-$C_6$)cycloalkanesulfinyl, ($C_3$-$C_7$)cycloalkyl($C_1$-$C_2$)alkanesulfinyl, halo($C_1$-$C_6$)alkanesulfinyl, halo($C_3$-$C_6$)cycloalkanesulfinyl, halo($C_3$-$C_7$)cycloalkyl($C_1$-$C_2$)alkanesulfinyl, ($C_1$-$C_6$)alkanesulfonyl, ($C_3$-$C_6$)cycloalkanesulfonyl, ($C_3$-$C_7$)cycloalkyl($C_1$-$C_2$)alkanesulfonyl, halo($C_1$-$C_6$)alkanesulfonyl, halo($C_3$-$C_6$)cycloalkanesulfonyl, halo($C_3$-$C_7$)cycloalkyl($C_1$-$C_2$)alkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2$NCO, $H_2$N$SO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclylsulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl, amino($C_1$-$C_6$)alkyl, ($C_1$-$C_6$)alkylamino($C_1$-$C_6$)alkyl, di($C_1$-$C_6$)alkylamino($C_1$-$C_6$)alkylamino($C_2$-$C_6$)alkoxy, ($C_1$-$C_6$)alkylamino($C_2$-$C_6$)alkoxy, di($C_1$-$C_6$)alkylamino($C_2$-$C_6$)alkoxy, ($C_1$-$C_6$)alkylcarbonyl, ($C_3$-$C_6$)cycloalkylcarbonyl, ($C_3$-$C_6$)cycloalkylaminocarbonyl, {($C_3$-$C_6$)cycloalkyl}{($C_1$-$C_6$)alkyl}aminocarbonyl, di($C_3$-$C_6$)cycloalkylaminocarbonyl, ($C_3$-$C_6$)cycloalkylaminosulfonyl, {($C_3$-$C_6$)cycloalkyl}{($C_1$-$C_6$)alkyl}aminosulfonyl, di($C_3$-$C_6$)cycloalkylaminosulfonyl, cyano($C_1$-$C_6$)alkyl, aminocarbonyl($C_1$-$C_6$)alkyl, ($C_1$-$C_6$)alkylaminocarbonyl($C_1$-$C_6$)alkyl, di($C_1$-$C_6$)alkylaminocarbonyl($C_1$-$C_6$)alkyl, ($C_3$-$C_6$)cycloalkylaminocarbonyl($C_1$-$C_6$)alkyl, {($C_3$-$C_6$)cycloalkyl}{($C_1$-$C_6$)alkyl}aminocarbonyl($C_1$-$C_6$)alkyl and di($C_3$-$C_6$)cycloalkylaminocarbonyl($C_1$-$C_6$)alkyl;

Y is ($C_1$-$C_6$)alkyl, halo($C_1$-$C_6$)alkyl or oxo;

n is 0, 1 or 2;

E is (a) a bond or (b) ($C_1$-$C_3$)alkylene or ($C_1$-$C_2$)alkylenyloxy, wherein the O is attached to $R^2$, each of which is optionally substituted with 1 to 4 groups independently selected from methyl, ethyl, trifluoromethyl or oxo;

$R^2$ is ($C_1$-$C_6$)alkyl, aryl, heteroaryl, cycloalkyl or heterocyclyl and is optionally substituted with up to 4 groups independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$)alkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkythio, ($C_4$-$C_7$)cycloalkylalkylthio, halo($C_1$-$C_6$)alkylthio, halo($C_3$-$C_6$)cycloalkythio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkanesulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$)cycloalkanesulfonyl, halo($C_4$-$C_7$)cycloalkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2$NCO, $H_2$N$SO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclylsulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl, oxo, amino($C_1$-$C_6$)alkyl, ($C_1$-$C_6$)alkylamino($C_1$-$C_6$)alkyl, di($C_1$-$C_6$)alkylamino($C_1$-$C_6$)alkylamino($C_2$-$C_6$)alkoxy, ($C_1$-$C_6$)alkylamino($C_2$-$C_6$)alkoxy, di($C_1$-$C_6$)alkylamino($C_2$-$C_6$)alkoxy, ($C_1$-$C_6$)alkylcarbonyl, ($C_3$-$C_6$)cycloalkylcarbonyl, ($C_3$-$C_6$)cycloalkylaminocarbonyl, {($C_3$-$C_6$)cycloalkyl}{($C_1$-$C_6$)alkyl}aminocarbonyl, di($C_3$-$C_6$)cycloalkylaminocarbonyl, ($C_3$-$C_6$)cycloalkylaminosulfonyl, {($C_3$-$C_6$)cycloalkyl}{($C_1$-$C_6$)alkyl}aminosulfonyl, di($C_3$-$C_6$)cycloalkylaminosulfonyl, cyano($C_1$-$C_6$)alkyl, aminocarbonyl($C_1$-$C_6$)alkyl, ($C_1$-$C_6$)alkylaminocarbonyl($C_1$-$C_6$)alkyl, di($C_1$-$C_6$)alkylaminocarbonyl($C_1$-$C_6$)alkyl, ($C_3$-$C_6$)cycloalkylaminocarbonyl($C_1$-$C_6$)alkyl, {($C_3$-$C_6$)cycloalkyl}{($C_1$-$C_6$)alkyl}aminocarbonyl($C_1$-$C_6$)alkyl and di($C_3$-$C_6$)cycloalkylaminocarbonyl($C_1$-$C_6$)alkyl;

$R^3$ is selected from ($C_1$-$C_6$)alkyl, ($C_2$-$C_6$)alkenyl, ($C_2$-$C_6$)alkynyl, ($C_3$-$C_5$)cycloalkyl($C_1$-$C_4$)alkyl, ($C_1$-$C_3$)alkoxy($C_1$-$C_3$)alkoxy, or ($C_1$-$C_3$)alkoxy($C_1$-$C_3$)alkyl and is optionally substituted with up to four groups independently selected from fluorine, cyano, oxo, $R^4$, $R^4$O—, $(R^4)_2$N—, $R^4O_2$C—, $R^4$C(=O)O—, $R^4$S, $R^4$S(=O)—, $R^4$S(=O)$_2$—, $R^4$C(=O)N$R^4$—, $(R^4)_2$NC(=O)—, $(R^4)_2$NC(=O)O—, $(R^4)_2$NC(=O)N$R^4$—, $R^4$OC(=O)N$R^4$—, $(R^4)_2$NC(=NCN)N$R^4$—, $(R^{40})_2$P(=O)O—, $(R^{40})_2$P(=O)N$R^4$—, $R^4$OS(=O)$_2$N$R^4$—, $(R^4)_2$NS(=O)$_2$O—, $(R^4)_2$NS(=O)$_2$N$R^4$—, $R^4$S(=O)$_2$N$R^4$—, $R^4$S(=O)$_2$NHC(=O)—, $R^4$S(=O)$_2$NHC(=O)O—, $R^4$S(=O)$_2$NHC(=O)N$R^4$—, $R^4$OS(=O)$_2$NHC(=O)—, $R^4$OS(=O)$_2$NHC(=O)O—, $R^4$OS(=O)$_2$NHC(=O)N$R^4$—, $(R^4)_2$NS(=O)$_2$NHC(=O)—, $(R^4)_2$NS(=O)$_2$NHC(=O)O—, $(R^4)_2$NS(=O)$_2$NHC(=O)N$R^4$—, $R^4$C(=O)NHS(=O)$_2$—, $R^4$C(=O)NHS(=O)$_2$O—, $R^4$C(=O)NHS(=O)$_2$N$R^4$—, $R^4$OC(=O)NHS(=O)$_2$—, $R^4$OC(=O)NHS(=O)$_2$O—, $R^4$OC(=O)NHS(=O)$_2$N$R^4$—, $(R^4)_2$NC(=O)NHS(=O)$_2$—, $(R^4)_2$NC(=O)NHS(=O)$_2$O—, $(R^4)_2$NC(=O)NHS(=O)$_2$N$R^4$—, spirocycloalkyl; heterocyclyl (which in turn may be optionally substituted with alkyl, haloalkyl, halogen or oxo), heteroaryl (which in turn may be optionally substituted with alkyl, haloalkyl, alkoxy, alkylthio, alkylsulfonyl, halogen, trifluoromethyl, dialkylamino, nitro, cyano, $CO_2$H, $CONH_2$, N-monoalkyl-substituted amido, N,N-dialkyl-substituted amido, or oxo), arylamino (which in turn may be optionally substituted with alkyl, alkoxy, alkylthio, alkylsulfonyl, halogen, trifluoromethyl, dialkylamino, nitro, cyano, $CO_2$H, $CONH_2$, N-monoalkyl-substituted amido and N,N-dialkyl-substituted amido) and heteroarylamino (which in turn may be optionally substituted with alkyl, haloalkyl, alkoxy, alkylthio, alkylsulfonyl, halogen, trifluoromethyl, dialkylamino, nitro, cyano, $CO_2$H, $CONH_2$, N-monoalkyl-substituted amido, N,N-dialkyl-substituted amido, or oxo); and $R^4$ is independently selected from H, ($C_1$-$C_6$)alkyl, halo($C_1$-$C_6$)alkyl, amino($C_1$-$C_6$)alkyl, ($C_1$-$C_6$)alkylamino($C_1$-$C_6$)alkyl, di($C_1$-$C_6$)alkylamino($C_1$-$C_6$)alkyl, hydroxy($C_1$-$C_6$)alkyl and ($C_1$-$C_6$)alkoxy($C_1$-$C_6$)alkyl; and R is (i) ($C_1$-$C_4$)alkyl optionally substituted with one or more halogen or (ii) phenyl, optionally substituted with halogen, ($C_1$-$C_4$)alkyl or $NO_2$;

or a pharmaceutically acceptable salt, enantiomer or diastereomer thereof.

In a second embodiment, the invention is a compound represented by Formula I, wherein variables are defined herein as follows:

$R^1$ is (a) absent or (b) is selected from $(C_1-C_6)$alkyl, $(C_2-C_6)$alkenyl, $(C_2-C_6)$alkynyl, $(C_1-C_3)$alkoxy$(C_1-C_3)$alkoxy, or $(C_1-C_3)$alkoxy$(C_1-C_3)$alkyl and is optionally substituted with up to four groups independently selected from fluorine, cyano, oxo, $R^4$, $R^4O$—, $(R^4)_2N$—, $R^4O_2C$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$—, $(R^4O)_2P(=O)O$—, $(R^4O)_2P(=O)NR^4$—, $R^4OS(=O)_2NR^4$—, $(R^4)_2NS(=O)_2O$—, $(R^4)_2NS(=O)_2NR^4$—, $R^4S(=O)_2NR^4$—, $R^4S(=O)_2NHC(=O)$—, $R^4S(=O)_2NHC(=O)O$—, $R^4S(=O)_2NHC(=O)NR^4$—, $R^4OS(=O)_2NHC(=O)$—, $R^4OS(=O)_2NHC(=O)O$—, $R^4OS(=O)_2NHC(=O)NR^4$—, $(R^4)_2NS(=O)_2NHC(=O)$—, $(R^4)_2NS(=O)_2NHC(=O)O$—, $(R^4)_2NS(=O)_2NHC(=O)NR^4$—, $R^4C(=O)NHS(=O)_2$—, $R^4C(=O)NHS(=O)_2O$—, $R^4C(=O)NHS(=O)_2NR^4$—, $R^4OC(=O)NHS(=O)_2$—, $R^4OC(=O)NHS(=O)_2O$—, $R^4OC(=O)NHS(=O)_2NR^4$—, $(R^4)_2NC(=O)NHS(=O)_2$—, $(R^4)_2NC(=O)NHS(=O)_2O$—, $(R^4)_2NC(=O)NHS(=O)_2NR^4$—, heterocyclyl, heteroaryl, arylamino and heteroarylamino;

$A^1$ is (a) a bond, or (b) $(C_1-C_3)$alkylene, $CH_2CH_2O$, wherein the oxygen is attached to $Cy^1$, or $CH_2C(=O)$, wherein the carbonyl carbon is attached to $Cy^1$;

$Cy^1$ is aryl, heteroaryl, monocyclic cycloalkyl or monocyclic heterocyclyl and is optionally substituted with 1 to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkylalkylthio, halo$(C_1-C_6)$alkylthio, halo$(C_3-C_6)$cycloalkythio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cycloalkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclylsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkylamino$(C_2-C_6)$alkoxy, $(C_1-C_6)$alkylamino$(C_2-C_6)$alkoxy, di$(C_1-C_6)$alkylamino$(C_2-C_6)$alkoxy, $(C_1-C_6)$alkylcarbonyl, $(C_3-C_6)$cycloalkylcarbonyl, $(C_3-C_6)$cycloalkylaminocarbonyl, $\{(C_3-C_6)$cycloalkyl$\}\{(C_1-C_6)$alkyl$\}$aminocarbonyl, di$(C_3-C_6)$cycloalkylaminocarbonyl, $(C_3-C_6)$cycloalkylaminosulfonyl, $\{(C_3-C_6)$cycloalkyl$\}\{(C_1-C_6)$alkyl$\}$aminosulfonyl, di$(C_3-C_6)$cycloalkylaminosulfonyl, cyano$(C_1-C_6)$alkyl, aminocarbonyl$(C_1-C_6)$alkyl, $(C_1-C_6)$alkylaminocarbonyl$(C_1-C_6)$alkyl, di$(C_1-C_6)$alkylaminocarbonyl$(C_1-C_6)$alkyl, $(C_3-C_6)$cycloalkylaminocarbonyl$(C_1-C_6)$alkyl, $\{(C_3-C_6)$cycloalkyl$\}\{(C_1-C_6)$alkyl$\}$aminocarbonyl$(C_1-C_6)$alkyl and di$(C_3-C_6)$cycloalkylaminocarbonyl$(C_1-C_6)$alkyl;

$Cy^2$ is benzimidazolyl, benzotriazolyl and piperidinyl and is optionally substituted with 1 to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkylalkylthio, halo$(C_1-C_6)$alkylthio, halo$(C_3-C_6)$cycloalkythio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cycloalkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclylsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkylamino$(C_2-C_6)$alkoxy, $(C_1-C_6)$alkylamino$(C_2-C_6)$alkoxy, di$(C_1-C_6)$alkylamino$(C_2-C_6)$alkoxy, $(C_1-C_6)$alkylcarbonyl, $(C_3-C_6)$cycloalkylcarbonyl, $(C_3-C_6)$cycloalkylaminocarbonyl, $\{(C_3-C_6)$cycloalkyl$\}\{(C_1-C_6)$alkyl$\}$aminocarbonyl, di$(C_3-C_6)$cycloalkylaminocarbonyl, $(C_3-C_6)$cycloalkylaminosulfonyl, $\{(C_3-C_6)$cycloalkyl$\}\{(C_1-C_6)$alkyl$\}$aminosulfonyl, di$(C_3-C_6)$cycloalkylaminosulfonyl, cyano$(C_1-C_6)$alkyl, aminocarbonyl$(C_1-C_6)$alkyl, $(C_1-C_6)$alkylaminocarbonyl$(C_1-C_6)$alkyl, di$(C_1-C_6)$alkylaminocarbonyl$(C_1-C_6)$alkyl, $(C_3-C_6)$cycloalkylaminocarbonyl$(C_1-C_6)$alkyl, $\{(C_3-C_6)$cycloalkyl$\}\{(C_1-C_6)$alkyl$\}$aminocarbonyl$(C_1-C_6)$alkyl and di$(C_3-C_6)$cycloalkylaminocarbonyl$(C_1-C_6)$alkyl; wherein the piperidinyl represented by $Cy^1$ is attached to $Cy^1$ through a ring carbon atom. In another embodiment, when $Cy^2$ is piperidinyl, oxo is also a possible substituent.

Alternatively, when $R^3$ is methoxymethyl, $Cy^2$ is (a) halogen or —O—$SO_3$—R or (b) cycloalkyl, aryl, heterocyclyl or heteroaryl, optionally substituted with 1 to 4 groups independently selected from fluorine, chlorine, bromine, iodine, cyano, nitro, amino, hydroxy, carboxy, $(C_1-C_6)$ alkyl, hydroxy($C_1$-$C_6$)alkyl, ($C_3$-$C_6$)cycloalkyl, hydroxy($C_3$-$C_6$)cycloalkyl, ($C_3$-$C_7$)cycloalkyl($C_1$-$C_2$)alkyl, ($C_2$-$C_6$)alkenyl, halo($C_2$-$C_6$)alkenyl, hydroxy($C_2$-$C_6$)alkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_3$-$C_7$)cycloalkyl($C_1$-$C_2$)alkyl, ($C_1$-$C_6$)alkoxy, ($C_3$-$C_6$)cycloalkoxy, ($C_3$-$C_7$)cycloalkyl($C_1$-$C_2$)alkoxy, halo($C_1$-$C_6$)alkoxy, halo($C_3$-$C_6$)cyclo alkoxy, halo($C_3$-$C_7$)cyclo alkyl($C_1$-$C_2$)alkoxy, ($C_1$-$C_6$)alkylthio, ($C_3$-$C_6$)cycloalkythio, ($C_3$-$C_7$)cycloalkyl($C_1$-$C_2$)alkylthio, halo($C_1$-$C_6$)alkylthio, halo($C_3$-$C_6$)cycloalkythio, halo($C_3$-$C_7$)cycloalkyl($C_1$-$C_2$)alkylthio, ($C_1$-$C_6$)alkanesulfinyl, ($C_3$-$C_6$)cycloalkanesulfinyl, ($C_3$-$C_7$)cycloalkyl($C_1$-$C_2$)alkanesulfinyl, halo($C_1$-$C_6$)alkanesulfinyl, halo($C_3$-$C_6$)cycloalkanesulfinyl, halo($C_3$-$C_7$)cycloalkyl($C_1$-$C_2$)alkanesulfinyl, ($C_1$-$C_6$)alkanesulfonyl, ($C_3$-$C_6$)cycloalkanesulfonyl, ($C_3$-$C_7$)cycloalkyl($C_1$-$C_2$)alkanesulfonyl, halo($C_1$-$C_6$)alkanesulfonyl, halo($C_3$-$C_6$)cycloalkanesulfonyl, halo($C_3$-$C_7$)cycloalkyl($C_1$-$C_2$)alkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclylsulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl, amino($C_1$-$C_6$)alkyl, ($C_1$-$C_6$)alkylamino($C_1$-$C_6$)alkyl, di($C_1$-$C_6$)alkylamino($C_1$-$C_6$)alkylamino($C_2$-$C_6$)alkoxy, ($C_1$-$C_6$)alkylamino($C_2$-$C_6$)alkoxy, di($C_1$-$C_6$)alkylamino($C_2$-$C_6$)alkoxy, ($C_1$-$C_6$)alkylcarbonyl, ($C_3$-$C_6$)cycloalkylcarbonyl, ($C_3$-$C_6$)cycloalkylaminocarbonyl, {($C_3$-$C_6$)cycloalkyl}{($C_1$-$C_6$)alkyl}aminocarbonyl, di($C_3$-$C_6$)cycloalkylaminocarbonyl, ($C_3$-$C_6$)cycloalkylaminosulfonyl, {($C_3$-$C_6$)cycloalkyl}{($C_1$-$C_6$)alkyl}aminosulfonyl, di($C_3$-$C_6$)cycloalkylaminosulfonyl, cyano($C_1$-$C_6$)alkyl, aminocarbonyl($C_1$-$C_6$)alkyl, ($C_1$-$C_6$)alkylaminocarbonyl($C_1$-$C_6$)alkyl, di($C_1$-$C_6$)alkylaminocarbonyl($C_1$-$C_6$)alkyl, ($C_3$-$C_6$)cycloalkylaminocarbonyl($C_1$-$C_6$)alkyl, {($C_3$-$C_6$)cycloalkyl}{($C_1$-$C_6$)alkyl}aminocarbonyl($C_1$-$C_6$)alkyl and di($C_3$-$C_6$)cycloalkylaminocarbonyl($C_1$-$C_6$)alkyl;

Y is ($C_1$-$C_6$)alkyl, halo($C_1$-$C_6$)alkyl or oxo;

n is 0, 1 or 2;

E is (a) a bond or (b) ($C_1$-$C_3$)alkylene or ($C_1$-$C_2$)alkylenyloxy, wherein the O is attached to $R^2$, each of which is optionally substituted with 1 to 4 groups independently selected from methyl, ethyl, trifluoromethyl or oxo;

$R^2$ is ($C_1$-$C_6$)alkyl, aryl, heteroaryl, cycloalkyl or heterocyclyl and is optionally substituted with up to 4 groups independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$)alkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkythio, ($C_4$-$C_7$)cycloalkylalkylthio, halo($C_1$-$C_6$)alkylthio, halo($C_3$-$C_6$)cycloalkythio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkanesulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$)cycloalkanesulfonyl, halo($C_4$-$C_7$)cycloalkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclylsulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl, oxo, amino($C_1$-$C_6$)alkyl, ($C_1$-$C_6$)alkylamino($C_1$-$C_6$)alkyl, di($C_1$-$C_6$)alkylamino($C_1$-$C_6$)alkylamino($C_2$-$C_6$)alkoxy, ($C_1$-$C_6$)alkylamino($C_2$-$C_6$)alkoxy, di($C_1$-$C_6$)alkylamino($C_2$-$C_6$)alkoxy, ($C_1$-$C_6$)alkylcarbonyl, ($C_3$-$C_6$)cycloalkylcarbonyl, ($C_3$-$C_6$)cycloalkylaminocarbonyl, {($C_3$-$C_6$)cycloalkyl}{($C_1$-$C_6$)alkyl}aminocarbonyl, di($C_3$-$C_6$)cycloalkylaminocarbonyl, ($C_3$-$C_6$)cycloalkylaminosulfonyl, {($C_3$-$C_6$)cycloalkyl}{($C_1$-$C_6$)alkyl}aminosulfonyl, di($C_3$-$C_6$)cycloalkylaminosulfonyl, cyano($C_1$-$C_6$)alkyl, aminocarbonyl($C_1$-$C_6$)alkyl, ($C_1$-$C_6$)alkylaminocarbonyl($C_1$-$C_6$)alkyl, di($C_1$-$C_6$)alkylaminocarbonyl($C_1$-$C_6$)alkyl, ($C_3$-$C_6$)cyclo alkylaminocarbonyl($C_1$-$C_6$)alkyl, {($C_3$-$C_6$)cycloalkyl}{($C_1$-$C_6$)alkyl}aminocarbonyl($C_1$-$C_6$)alkyl and di($C_3$-$C_6$)cycloalkylaminocarbonyl($C_1$-$C_6$)alkyl;

$R^3$ is selected from ($C_1$-$C_6$)alkyl, ($C_2$-$C_6$)alkenyl, ($C_2$-$C_6$)alkynyl, ($C_3$-$C_5$)cycloalkyl($C_1$-$C_4$)alkyl, ($C_1$-$C_3$)alkoxy($C_1$-$C_3$)alkoxy, or ($C_1$-$C_3$)alkoxy($C_1$-$C_3$)alkyl and is optionally substituted with up to four groups independently selected from fluorine, cyano, oxo, $R^4$, $R^4O$—, $(R^4)_2N$—, $R^4O_2C$—, $R^4C(=O)O$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$—, $(R^4O)_2P(=O)O$—, $(R^4O)_2P(=O)NR^4$—, $R^4OS(=O)_2NR^4$—, $(R^4)_2NS(=O)_2O$—, $(R^4)_2NS(=O)_2NR^4$—, $R^4S(=O)_2NR^4$—, $R^4S(=O)_2NHC(=O)$—, $R^4S(=O)_2NHC(=O)O$—, $R^4S(=O)_2NHC(=O)NR^4$—, $R^4OS(=O)_2NHC(=O)$—, $R^4OS(=O)_2NHC(=O)O$—, $R^4OS(=O)_2NHC(=O)NR^4$—, $(R^4)_2NS(=O)_2NHC(=O)$—, $(R^4)_2NS(=O)_2NHC(=O)O$—, $(R^4)_2NS(=O)_2NHC(=O)NR^4$—, $R^4C(=O)NHS(=O)_2$—, $R^4C(=O)NHS(=O)_2O$—, $R^4C(=O)NHS(=O)_2NR^4$—, $R^4OC(=O)NHS(=O)_2$—, $R^4OC(=O)NHS(=O)_2O$—, $R^4OC(=O)NHS(=O)_2NR^4$—, $(R^4)_2NC(=O)NHS(=O)_2$—, $(R^4)_2NC(=O)NHS(=O)_2O$—, $(R^4)_2NC(=O)NHS(=O)_2NR^4$—, spirocycloalkyl; heterocyclyl (which in turn may be optionally substituted with alkyl, haloalkyl, halogen or oxo), heteroaryl (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo), arylamino (which in turn may be optionally substituted with alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido) and heteroarylamino (which in turn may be optionally substituted with alkyl, haloalkyl, alkoxy, alkylthio, alkylsulfonyl, halogen, trifluoromethyl, dialkylamino, nitro, cyano, CO$_2$H, CONH$_2$, N-monoalkyl-substituted amido, N,N-dialkyl-substituted amido, or oxo); and R$^4$ is independently selected from H, (C$_1$-C$_6$)alkyl, halo(C$_1$-C$_6$)alkyl, amino(C$_1$-C$_6$)alkyl, (C$_1$-C$_6$)alkylamino(C$_1$-C$_6$)alkyl, di(C$_1$-C$_6$)alkylamino(C$_1$-C$_6$)alkyl, hydroxy(C$_1$-C$_6$)alkyl and (C$_1$-C$_6$)alkoxy(C$_1$-C$_6$)alkyl; and R is (i) (C$_1$-C$_4$)alkyl optionally substituted with one or more halogen or (ii) phenyl, optionally substituted with halogen, (C$_1$-C$_4$)alkyl or NO$_2$;

or a pharmaceutically acceptable salt, enantiomer or diastereomer thereof.

Another embodiment of the invention is a method of inhibiting 11β-HSD1 activity comprising the step of administering to a mammal in need of such treatment an effective amount of a compound of Formulas I, Ia$^{1-10}$, Ib$^{1-10}$, Ic$^{1-10}$, Id$^{1-7}$ or Ie$^{1-5}$ or a pharmaceutically acceptable salt, enantiomer or diastereomer thereof.

Another embodiment of the invention is a method of treating a subject with a disease associated with the activity or expression of 11β-HSD1, comprising the step of administering to the subject an effective amount of a compound of Formulas I, Ia$^{1-10}$, Ib$^{1-10}$, Ic$^{1-10}$, Id$^{1-7}$ or Ie$^{1-5}$ or a pharmaceutically acceptable salt, enantiomer or diastereomer thereof.

Another embodiment of the invention is the use of a compound of Formulas I, Ia$^{1-10}$, Ib$^{1-10}$, Ic$^{1-10}$, Id$^{1-7}$ or Ie$^{1-5}$ or a pharmaceutically acceptable salt, enantiomer or diastereomer thereof for the manufacture of a medicament for inhibiting 11β-HSD1 activity in a mammal in need of such treatment.

Another embodiment of the invention is the use of a compound of Formulas I, Ia$^{1-10}$, Ib$^{1-10}$, Ic$^{1-10}$, Id$^{1-7}$ or Ie$^{1-5}$ or a pharmaceutically acceptable salt, enantiomer or diastereomer thereof for the manufacture of a medicament for treating a subject with a disease associated with the activity or expression of 11β-HSD1.

Another embodiment of the invention is a compound of Formulas I, Ia$^{1-10}$, Ib$^{1-10}$, Ic$^{1-10}$, Id$^{1-7}$ or Ie$^{1-5}$ or a pharmaceutically acceptable salt, enantiomer or diastereomer thereof for use in inhibiting 11β-HSD1 activity in a mammal in need of such treatment.

Another embodiment of the invention is a compound of Formulas I, Ia$^{1-10}$, Ib$^{1-10}$, Ic$^{1-10}$, Id$^{1-7}$ or Ie$^{1-5}$ or a pharmaceutically acceptable salt, enantiomer or diastereomer thereof for use in for treating a subject with a disease associated with the activity or expression of 11β-HSD1.

Another embodiment of the present invention is a pharmaceutical composition comprising: i) a pharmaceutically acceptable carrier or diluent; and ii) compound of Formulas I, Ia$^{1-10}$, Ib$^{1-10}$, Ic$^{1-10}$, Id$^{1-7}$ or Ie$^{1-5}$ or a pharmaceutically acceptable salt, enantiomer or diastereomer, thereof.

DETAILED DESCRIPTION OF THE INVENTION

In a third embodiment, the variables in Formula I:

R$^1$ is (a) absent or (b) (C$_1$-C$_6$)alkyl or (C$_1$-C$_6$)cycloalkyl and is optionally substituted with up to four groups independently selected from fluorine, cyano, oxo, R$^4$, R$^4$O—, (R$^4$)$_2$N—, R$^4$O$_2$C—, R$^4$S, R$^4$S(=O)—, R$^4$S(=O)$_2$—, R$^4$C(=O)NR$^4$—, (R$^4$)$_2$NC(=O)—, (R$^4$)$_2$NC(=O)O—, (R$^4$)$_2$NC(=O)NR$^4$—, R$^4$OC(=O)NR$^4$—, (R$^4$)$_2$NS(=O)$_2$NR$^4$— and R$^4$S(=O)$_2$NR$^4$—.

A$^1$ is (a) a bond, (b) (C$_1$-C$_2$)alkylene, or (c) CH if R$^1$ is present.

n is 0.

E is a bond or CH$_2$.

R$^2$ is (C$_1$-C$_6$)alkyl, aryl, heteroaryl, cycloalkyl or heterocyclyl and is optionally substituted with up to 4 groups independently selected from fluorine, chlorine, bromine, iodine, cyano, nitro, amino, hydroxy, carboxy, (C$_1$-C$_6$)alkyl, hydroxy(C$_1$-C$_6$)alkyl, (C$_3$-C$_6$)cycloalkyl, hydroxy(C$_3$-C$_6$)cycloalkyl, halo(C$_1$-C$_6$)alkyl, (C$_1$-C$_6$)alkoxy, (C$_3$-C$_6$)cycloalkoxy, halo(C$_1$-C$_6$)alkoxy, (C$_1$-C$_6$)alkanesulfonyl, halo(C$_1$-C$_6$)alkanesulfonyl, halo(C$_3$-C$_6$)cycloalkanesulfonyl, H$_2$NCO, H$_2$NSO$_2$, (C$_1$-C$_6$)alkylaminocarbonyl, di(C$_1$-C$_6$)alkylaminocarbonyl, heterocyclylcarbonyl, (C$_1$-C$_6$)alkylaminosulfonyl, di(C$_1$-C$_6$)alkylaminosulfonyl, heterocyclylsulfonyl, (C$_1$-C$_6$)alkylcarbonylamino, (C$_1$-C$_6$)alkylcarbonylamino(C$_1$-C$_6$)alkyl, (C$_1$-C$_6$)alkylsulfonylamino and oxo.

R$^3$ is selected from (C$_1$-C$_6$)alkyl, (C$_2$-C$_6$)alkenyl, (C$_2$-C$_6$)alkynyl, (C$_3$-C$_5$)cycloalkyl(C$_1$-C$_4$)alkyl, (C$_1$-C$_3$)alkoxy(C$_1$-C$_3$)alkoxy, or (C$_1$-C$_3$)alkoxy(C$_1$-C$_3$)alkyl and is optionally substituted with up to four groups independently selected from fluorine, cyano, oxo, R$^4$, R$^{40}$—, R$^4$S—, (R$^4$)$_2$N—, R$^4$OCR$^4$$_2$CR$^4$$_2$NR$^4$—, R$^4$OCR$^4$$_2$C(=O)NR$^4$—, R$^4$OCR$^4$$_2$CR$^4$$_2$O—, R$^4$O$_2$C—, R$^4$S, R$^4$S(=O)—, R$^4$S(=O)$_2$—, R$^4$C(=O)NR$^4$—, (R$^4$)$_2$NC(=O)—, (R$^4$)$_2$NC(=O)O—, (R$^4$)$_2$NC(=O)NR$^4$—, R$^4$OC(=O)NR$^4$—, (R$^4$)$_2$NS(=O)$_2$NR$^4$—, R$^4$S(=O)$_2$NR$^4$—, R$^4$$_2$NS(=O)$_2$O—, (R$^{40}$)$_2$P(=O)O—, R$^4$$_2$NCR$^4$$_2$C(=O)NR$^4$—, N(R$^4$)$_2$C(=NCN)NR$^4$—, R$^4$S(=O)$_2$NR$^4$C(=O)—, imidazolylamino-, imidazolyl, tetrazolyl, 4-morpholino, azetidinyl, pyrrolidinyl, fluoropyrrolidinyl, oxopiperazinyl, 1, dioxoisothiazolidinyl, methylimidazolyl, methyloxadiazolyl, methylthiadiazolyl and (1-hydroxycyclopropyl)methyl.

Alternatively, R$^3$ is methoxymethyl.

R$^4$ is independently selected from H, (C$_1$-C$_6$)alkyl and halo(C$_1$-C$_6$)alkyl;

or a pharmaceutically acceptable salt, enantiomer or diastereomer thereof. Values for the remaining variables are as defined above for the first or second embodiment of Formula (I).

In a fourth embodiment, the variables in Formula I:

R$^1$ is (a) absent or (b) (C$_1$-C$_6$)alkyl is optionally substituted with up to four groups independently selected from fluorine, cyano, oxo, R$^4$, R$^4$O—, (R$^4$)$_2$N—, R$^4$O$_2$C—, R$^4$S, R$^4$S(=O)—, R$^4$S(=O)$_2$—, R$^4$C(=O)NR$^4$—, (R$^4$)$_2$NC(=O)—, (R$^4$)$_2$NC(=O)O—, (R$^4$)$_2$NC(=O)NR$^4$—, R$^4$OC(=O)NR$^4$—, (R$^4$)$_2$NS(=O)$_2$NR$^4$— and R$^4$S(=O)$_2$NR$^4$—.

A$^1$ is (a) a bond, (b) (C$_1$-C$_2$)alkylene, or (c) CH if R$^1$ is present.

n is 0.

E is a bond or CH$_2$.

R$^2$ is (C$_1$-C$_6$)alkyl, aryl, heteroaryl, cycloalkyl or heterocyclyl and is optionally substituted with up to 4 groups independently selected from fluorine, chlorine, bromine, iodine, cyano, nitro, amino, hydroxy, carboxy, (C$_1$-C$_6$)alkyl, hydroxy(C$_1$-C$_6$)alkyl, (C$_3$-C$_6$)cycloalkyl, hydroxy(C$_3$-C$_6$)cycloalkyl, halo(C$_1$-C$_6$)alkyl, (C$_1$-C$_6$)alkoxy, (C$_3$-C$_6$)cycloalkoxy, halo(C$_1$-C$_6$)alkoxy, (C$_1$-C$_6$)alkanesulfonyl, halo(C$_1$-C$_6$)alkanesulfonyl, halo(C$_3$-C$_6$)cycloalkanesulfonyl, H$_2$NCO, H$_2$NSO$_2$, (C$_1$-C$_6$)alkylaminocarbonyl, di(C$_1$-C$_6$)alkylaminocarbonyl, heterocyclylcarbonyl, (C$_1$-C$_6$)alkylaminosulfonyl, di(C$_1$-C$_6$)alkylaminosulfonyl, heterocyclylsulfonyl, (C$_1$-C$_6$)alkylcarbonylamino, (C$_1$-C$_6$)alkylcarbonylamino(C$_1$-C$_6$)alkyl, (C$_1$-C$_6$)alkylsulfonylamino and oxo.

R$^3$ is selected from (C$_1$-C$_6$)alkyl, (C$_2$-C$_6$)alkenyl, (C$_2$-C$_6$)alkynyl, (C$_3$-C$_5$)cycloalkyl(C$_1$-C$_4$)alkyl, (C$_1$-C$_3$)alkoxy(C$_1$-C$_3$)alkoxy, or (C$_1$-C$_3$)alkoxy(C$_1$-C$_3$)alkyl and is optionally substituted with up to four groups independently selected from fluorine, cyano, oxo, R$^4$, R$^4$O—, R$^4$S—, (R$^4$)$_2$N—, R$^4$OCR$^4$$_2$CR$^4$$_2$NR$^4$—, R$^4$OCR$^4$$_2$C(=O)NR$^4$—, $R^4OCR^4{}_2CR^4{}_2O-$, $R^4O_2C-$, $R^4S-$, $R^4S(=O)-$, $R^4S(=O)_2-$, $R^4C(=O)NR^4-$, $(R^4)_2NC(=O)-$, $(R^4)_2NC(=O)O-$, $(R^4)_2NC(=O)NR^4-$, $R^4OC(=O)NR^4-$, $(R^4)_2NS(=O)_2NR^4-$, $R^4S(=O)_2NR^4-$, $R^4{}_2NS(=O)_2O-$, $(R^4O)_2P(=O)O-$, $R^4{}_2NCR^4{}_2C(=O)NR^4-$, $N(R^4)_2C(=NCN)NR^4-$, $R^4S(=O)_2NR^4C(=O)-$, imidazolylamino-, imidazolyl, tetrazolyl, 4-morpholino, azetidinyl, pyrrolidinyl, fluoropyrrolidinyl, oxopiperazinyl, 1, dioxoisothiazolidinyl, methylimidazolyl, methyloxadiazolyl, methylthiadiazolyl and (1-hydroxycyclopropyl)methyl.

Alternatively, $R^3$ is methoxymethyl.

$R^4$ is independently selected from H, $(C_1-C_6)$alkyl and halo$(C_1-C_6)$alkyl;

or a pharmaceutically acceptable salt, enantiomer or diastereomer thereof. Values for the remaining variables are as defined above for the first or second embodiment of Formula (I).

In a fifth embodiment, the variables in Formula I or any one of Formulas $Ia^{1-10}$-$Ie^{1-5}$ are as defined in the following paragraphs:

$R^1$ is absent or is methyl, ethyl or cyclopropyl.

$A^1$ is a bond or $CH_2$ or CH when $R^1$ is present.

$Cy^1$ is phenyl, cyclohexyl, pyridyl, N-oxo-pyridyl, thiazolyl or pyrimidinyl each optionally substituted with 1 to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, $(C_3-C_6)$cycloalkyl$(C_1-C_2)$alkyl, hydroxy$(C_3-C_6)$cycloalkyl, halo$(C_1-C_6)$alkyl, $(C_1-C_6)$alkoxy, $(C_3-C_6)$cycloalkoxy, halo$(C_1-C_6)$alkoxy, $(C_1-C_6)$alkanesulfonyl, halo$(C_1-C_6)$alkanesulfonyl, halo$(C_3-C_6)$cycloalkanesulfonyl, $H_2NCO$, $H_2NSO_2$, $(C_1-C_6)$alkylaminocarbonyl, di$(C_1-C_6)$alkylaminocarbonyl, heterocyclylcarbonyl, $(C_1-C_6)$alkylaminosulfonyl, di$(C_1-C_6)$alkylaminosulfonyl, heterocyclylsulfonyl, $(C_1-C_6)$alkylcarbonylamino, $(C_1-C_6)$alkylcarbonylamino$(C_1-C_6)$alkyl, $(C_1-C_6)$alkylsulfonylamino, oxo, cyano$(C_1-C_6)$alkyl, aminocarbonyl$(C_1-C_6)$alkyl, $(C_1-C_6)$alkylaminocarbonyl$(C_1-C_6)$alkyl and di$(C_1-C_6)$alkylaminocarbonyl$(C_1-C_6)$alkyl.

$Cy^2$ is benzimidazolyl, benzotriazolyl and piperidinyl each optionally substituted by 1 to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, $(C_3-C_6)$cycloalkyl$(C_1-C_2)$alkyl, hydroxy$(C_3-C_6)$cycloalkyl, halo$(C_1-C_6)$alkyl, $(C_1-C_6)$alkoxy, $(C_3-C_6)$cycloalkoxy, halo$(C_1-C_6)$alkoxy, $(C_1-C_6)$alkanesulfonyl, halo$(C_1-C_6)$alkanesulfonyl, halo$(C_3-C_6)$cycloalkanesulfonyl, $H_2NCO$, $H_2NSO_2$, $(C_1-C_6)$alkylaminocarbonyl, di$(C_1-C_6)$alkylaminocarbonyl, $(C_1-C_6)$cycloalkylcarbonyl, heterocyclylcarbonyl, $(C_1-C_6)$alkylaminosulfonyl, di$(C_1-C_6)$alkylaminosulfonyl, heterocyclylsulfonyl, $(C_1-C_6)$alkylcarbonylamino, $(C_1-C_6)$alkylcarbonyl, hydroxy$(C_1-C_6)$alkylcarbonyl, $(C_1-C_6)$alkylcarbonylamino$(C_1-C_6)$alkyl, $(C_1-C_6)$alkoxycarbonyl, $(C_1-C_6)$alkylsulfonylamino, oxo, cyano$(C_1-C_6)$alkyl, aminocarbonyl$(C_1-C_6)$alkyl, $(C_1-C_6)$alkylaminocarbonyl$(C_1-C_6)$alkyl and di$(C_1-C_6)$alkylaminocarbonyl$(C_1-C_6)$alkyl. Alternatively, when $Cy^2$ is piperidinyl, oxo is also a possible substituent.

Alternatively, when $R^3$ is methoxymethyl, $Cy^2$ is (a) halogen or $-O-SO_3-R$, or (b) cycloalkyl, aryl, heterocyclyl, heteroaryl, optionally substituted by 1 to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, $(C_3-C_6)$cycloalkyl$(C_1-C_2)$alkyl, hydroxy$(C_3-C_6)$cycloalkyl, halo$(C_1-C_6)$alkyl, $(C_1-C_6)$alkoxy, $(C_3-C_6)$cycloalkoxy, halo$(C_1-C_6)$alkoxy, $(C_1-C_6)$alkanesulfonyl, halo$(C_1-C_6)$alkanesulfonyl, halo$(C_3-C_6)$cycloalkanesulfonyl, $H_2NCO$, $H_2NSO_2$, $(C_1-C_6)$alkylaminocarbonyl, di$(C_1-C_6)$alkylaminocarbonyl, heterocyclylcarbonyl, $(C_1-C_6)$alkylaminosulfonyl, di$(C_1-C_6)$alkylaminosulfonyl, heterocyclylsulfonyl, $(C_1-C_6)$alkylaminosulfonyl, heterocyclylsulfonyl, $(C_1-C_6)$alkylcarbonylamino, $(C_1-C_6)$alkylcarbonyl, $(C_1-C_6)$alkylcarbonylamino$(C_1-C_6)$alkyl, $(C_1-C_6)$alkoxycarbonyl, $(C_1-C_6)$alkylsulfonylamino, oxo, cyano$(C_1-C_6)$alkyl, aminocarbonyl$(C_1-C_6)$alkyl, $(C_1-C_6)$alkylaminocarbonyl$(C_1-C_6)$alkyl and di$(C_1-C_6)$alkylaminocarbonyl$(C_1-C_6)$alkyl.

$R^2$ is methyl, ethyl, propyl, phenyl, thienyl or pyridyl each optionally substituted with halo, cyano, $CONH_2$, $(C_1-C_4)$alkyl, $(C_1-C_4)$haloalkyl, and $SO_2Me$.

$R^3$ is methyl, ethyl, propyl, butyl, vinyl, allyl or ethoxyethyl each optionally substituted with up to two groups independently selected from methyl, HO—, MeO—, $H_2N$—, MeC(=O)NH—, MeS(=O)$_2$NH—, $H_2NC$(=O)—, MeNHC(=O)—, $HO_2C$—, $(HO)_2P$(=O)O—, $H_2NS$(=O)$_2$O—, $H_2NS$(=O)$_2$NH—, MeNHC(=O)NH—, MeNHC(=O)O—, oxo, cyano, $HO_2C$—, $HOCH_2CH_2NH$—, 4-morpholino, $HOCH_2C$(=O)NH—, $H_2NCH_2C$(=O)NH—, EtNHC(=O)NH, MeOC(=O)NH—, MeNHC(=NCN)NH—, Me—, MeS—, $MeSO_2$—$MeSO_2N$(Me)—, MeS(=O)$_2$NHC(=O)—, imidazolylamino-, imidazolyl, tetrazolyl, $H_2NCONH$—, $H_2NCO_2$—, $HOCH_2CH_2O$—, MeNH—, $Me_2N$—, MeCON(Me)—, 2-fluoroethylamino, azetidinyl, pyrrolidinyl, 3-fluoropyrrolidinyl, 3-oxopiperazinyl, 1,1-dioxoisothiazolidin-2-yl, 5-methyl-1H-imidazol-2-yl, 5-methyl-1,3,4-oxadiazol-2-yl, 5-methyl-1,3,4-thiadiazol-2-yl, EtOC(=O)NH—, fluoro or (1-hydroxycyclopropyl)methyl. Alternatively, $R^3$ is methoxymethyl.

R is (i) $(C_1-C_4)$alkyl optionally substituted with one or more halogen or (ii) phenyl, optionally substituted with halogen, $(C_1-C_4)$alkyl or $NO_2$;

Pharmaceutically acceptable salts, enantiomers or diastereomers thereof are also included; and values for the remaining variables are as defined for Formula (I) and for first, second, third or fourth embodiment.

In a sixth embodiment, the variables of Formula I or any one of Formulas $Ia^{1-10}$-$Ie^{1-5}$ are as defined in the following paragraphs:

$R^1$ is absent or is methyl or ethyl.

$A^1$ is a bond or $CH_2$ or CH when $R^1$ is present.

$Cy^1$ is phenyl, cyclohexyl, pyridyl, N-oxo-pyridyl, thiazolyl or pyrimidinyl each optionally substituted with 1 to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, $(C_3-C_6)$cycloalkyl$(C_1-C_2)$alkyl, hydroxy$(C_3-C_6)$cycloalkyl, halo$(C_1-C_6)$alkyl, $(C_1-C_6)$alkoxy, $(C_3-C_6)$cycloalkoxy, halo$(C_1-C_6)$alkoxy, $(C_1-C_6)$alkanesulfonyl, halo$(C_1-C_6)$alkanesulfonyl, halo$(C_3-C_6)$cycloalkanesulfonyl, $H_2NCO$, $H_2NSO_2$, $(C_1-C_6)$alkylaminocarbonyl, di$(C_1-C_6)$alkylaminocarbonyl, heterocyclylcarbonyl, $(C_1-C_6)$alkylaminosulfonyl, di$(C_1-C_6)$alkylaminosulfonyl, heterocyclylsulfonyl, $(C_1-C_6)$alkylcarbonylamino, $(C_1-C_6)$alkylcarbonylamino$(C_1-C_6)$alkyl, $(C_1-C_6)$alkylsulfonylamino, oxo, cyano$(C_1-C_6)$alkyl, aminocarbonyl$(C_1-C_6)$alkyl, $(C_1-C_6)$alkylaminocarbonyl$(C_1-C_6)$alkyl and di$(C_1-C_6)$alkylaminocarbonyl$(C_1-C_6)$alkyl.

$Cy^2$ is benzimidazolyl, benzotriazolyl and piperidinyl each optionally substituted by 1 to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, $(C_3-C_6)$cycloalkyl$(C_1-C_2)$alkyl, hydroxy$(C_3-C_6)$cycloalkyl, halo$(C_1-C_6)$alkyl, $(C_1-C_6)$alkoxy, $(C_3-C_6)$cycloalkoxy, halo$(C_1-C_6)$alkoxy, $(C_1-C_6)$alkanesulfonyl, halo $(C_1-C_6)$alkanesulfonyl, halo$(C_3-C_6)$cycloalkanesulfonyl, $H_2NCO$, $H_2NSO_2$, $(C_1-C_6)$alkylaminocarbonyl, di$(C_1-C_6)$alkylaminocarbonyl, heterocyclylcarbonyl, $(C_1-C_6)$alkylaminosulfonyl, di$(C_1-C_6)$alkylaminosulfonyl, heterocyclylsulfonyl, $(C_1-C_6)$alkylcarbonylamino, $(C_1-C_6)$alkylcarbonyl, $(C_1-C_6)$alkylcarbonylamino$(C_1-C_6)$alkyl, $(C_1-C_6)$alkoxycarbonyl, $(C_1-C_6)$alkylsulfonylamino, oxo, cyano$(C_1-C_6)$alkyl, aminocarbonyl$(C_1-C_6)$alkyl, $(C_1-C_6)$alkylaminocarbonyl $(C_1-C_6)$alkyl and di$(C_1-C_6)$alkylaminocarbonyl$(C_1-C_6)$alkyl. Alternatively, when $Cy^2$ is piperidinyl, oxo is also a possible substituent.

Alternatively, when $R^3$ is methoxymethyl, $Cy^2$ is (a) halogen or —O—$SO_3$—R, or (b) cycloalkyl, aryl, heterocyclyl, heteroaryl, optionally substituted by 1 to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, $(C_3-C_6)$cycloalkyl$(C_1-C_2)$alkyl, hydroxy$(C_3-C_6)$cycloalkyl, halo$(C_1-C_6)$alkyl, $(C_1-C_6)$alkoxy, $(C_3-C_6)$cycloalkoxy, halo$(C_1-C_6)$alkoxy, $(C_1-C_6)$alkanesulfonyl, halo$(C_1-C_6)$alkanesulfonyl, halo$(C_3-C_6)$cycloalkanesulfonyl, $H_2NCO$, $H_2NSO_2$, $(C_1-C_6)$alkylaminocarbonyl, di$(C_1-C_6)$alkylaminocarbonyl, heterocyclylcarbonyl, $(C_1-C_6)$alkylaminosulfonyl, di$(C_1-C_6)$alkylaminosulfonyl, heterocyclylsulfonyl, $(C_1-C_6)$alkylcarbonylamino, $(C_1-C_6)$alkylcarbonyl, $(C_1-C_6)$alkylcarbonylamino$(C_1-C_6)$alkyl, $(C_1-C_6)$alkoxycarbonyl, $(C_1-C_6)$alkylsulfonylamino, oxo, cyano$(C_1-C_6)$alkyl, aminocarbonyl$(C_1-C_6)$alkyl, $(C_1-C_6)$alkylaminocarbonyl$(C_1-C_6)$alkyl and di$(C_1-C_6)$alkylaminocarbonyl$(C_1-C_6)$alkyl.

$R^2$ is phenyl, thienyl or pyridyl each optionally substituted with halo, cyano, $CONH_2$, $(C_1-C_4)$alkyl, $(C_1-C_4)$haloalkyl, and $SO_2Me$.

$R^3$ is methyl, ethyl, propyl, butyl, vinyl, allyl or ethoxyethyl each optionally substituted with up to two groups independently selected from methyl, HO—, MeO—, $H_2N$—, MeC(=O)NH—, MeS(=O)$_2$NH—, $H_2NC$(=O)—, MeNHC(=O)—, $HO_2C$—, $(HO)_2P$(=O)O—, $H_2NS$(=O)$_2$O—, $H_2NS$(=O)$_2$NH—, MeNHC(=O)NH—, MeNHC(=O)O—, oxo, cyano, $HO_2C$—, $HOCH_2CH_2NH$—, 4-morpholino, $HOCH_2C$(=O)NH—, $H_2NCH_2C$(=O)NH—, EtNHC(=O)NH, MeOC(=O)NH—, MeNHC(=NCN)NH—, Me—, MeS—, $MeSO_2$—, $MeSO_2N$(Me)—, MeS(=O)$_2$NHC(=O)—, imidazolylamino-, imidazolyl, tetrazolyl, $H_2NCONH$—, $H_2NCO_2$—, $HOCH_2CH_2O$—, MeNH—, $Me_2N$—, MeCON(Me)—, 2-fluoroethylamino, azetidinyl, pyrrolidinyl, 3-fluoropyrrolidinyl, 3-oxopiperazinyl, 1,1-dioxoisothiazolidin-2-yl, 5-methyl-1H-imidazol-2-yl, 5-methyl-1,3,4-oxadiazol-2-yl, 5-methyl-1,3,4-thiadiazol-2-yl, EtOC(=O)NH—, fluoro or (1-hydroxycyclopropyl)methyl. Alternatively, $R^3$ is methoxymethyl.

R is (i) $(C_1-C_4)$alkyl optionally substituted with one or more halogen or (ii) phenyl, optionally substituted with halogen, $(C_1-C_4)$alkyl or $NO_2$;

Pharmaceutically acceptable salts, enantiomers or diastereomers thereof are also included; and values for the remaining variables are as defined for first second, third or fourth embodiment.

In a seventh embodiment, the variables in Formula I or any one of Formulas Ia$^{1-10}$-Ie$^{1-5}$ are as defined in the following paragraphs:

$Cy^1$ is phenyl, cyclopropyl, cyclohexyl, pyrrolidinyl, pyridyl, N-oxo-pyridyl, thiazolyl, pyrimidinyl, piperidinyl, each optionally substituted with 1 to 4 groups independently selected from halo, nitro, $(C_1-C_4)$alkyl, $(C_1-C_4)$haloalkyl, trifluoromethyl, hydroxy, $(C_1-C_4)$alkoxy, $(C_1-C_4)$haloalkoxy, methoxycarbonyl, carboxy, ethoxycarbonylmethoxy, 2-hydroxy-2-methylpropoxy, cyano, difluoromethoxy, t-butoxycarbonyl, hydroxy, hydroxymethyl, 2-hydroxyethyl, 2-hydroxy-2-propyl, methoxymethyl, methylsulfonyl, methylsulfonylamino, trifluoromethoxy and 2,2,2-trifluoroethoxy.

$Cy^2$ is benzimidazolyl, benzotriazolyl and piperidinyl each optionally substituted by 1 to 4 groups independently selected from fluorine, chlorine, cyano, hydroxy, amino, $(C_1-C_4)$alkyl, $(C_3-C_4)$cycloalkyl, $(C_3-C_4)$cycloalkyl$(C_1-C_2)$alkyl, $(C_1-C_4)$alkoxy, $(C_1-C_4)$haloalkoxy, $(C_1-C_4)$alkanesulfonyl, $(C_1-C_4)$alkyloxycarbonyl, $(C_1-C_4)$alkylcarbonyl, hydroxy$(C_1-C_4)$alkylcarbonyl, tetrahydrofuranylcarbonyl, $CONH_2$, $(C_1-C_4)$alkylaminocarbonyl, di$(C_1-C_4)$alkylaminocarbonyl, $(C_1-C_4)$alkylcarbonylamino and $(C_1-C_4)$haloalkyl. Alternatively, when $Cy^2$ is piperidinyl, oxo is also a possible substituent.

Alternatively, when $R^3$ is methoxymethyl, $Cy^2$ is (a) halogen or —O—$SO_3$—R; or (b) cycloalkyl, aryl, heterocyclyl or heteroaryl, optionally substituted by 1 to 4 groups independently selected from fluorine, chlorine, cyano, hydroxy, amino, $C_1-C_4$ alkyl, $(C_3-C_4)$cycloalkyl, $(C_3-C_4)$cycloalkyl$(C_1-C_2)$alkyl, $(C_1-C_4)$alkoxy, $(C_1-C_4)$haloalkoxy, $CONH_2$, $(C_1-C_4)$alkylaminocarbonyl, di$(C_1-C_4)$alkylaminocarbonyl and $(C_1-C_4)$alkylcarbonylamino and $C_1-C_4$ haloalkyl; and R is (i) $(C_1-C_4)$alkyl optionally substituted with one or more halogen or (ii) phenyl, optionally substituted with halogen, $(C_1-C_4)$alkyl or $NO_2$;

or a pharmaceutically acceptable salt, enantiomer or diastereomer thereof. Values for the remaining variables are as defined for first second, third, fourth, fifth or sixth embodiment.

In a eighth embodiment, the variables in Formula I or any one of Formulas Ia$^{1-10}$-Ie$^{1-5}$ are as defined in the following paragraphs:

$Cy^1$ is phenyl, cyclopropyl, cyclohexyl, pyrrolidinyl, pyridyl, N-oxo-pyridyl, thiazolyl, pyrimidinyl, piperidinyl, each optionally substituted with 1 to 4 groups independently selected from halo, nitro, $(C_1-C_4)$alkyl, $(C_1-C_4)$haloalkyl, trifluoromethyl, hydroxy, $(C_1-C_4)$alkoxy, $(C_1-C_4)$haloalkoxy, methoxycarbonyl, carboxy, ethoxycarbonylmethoxy, 2-hydroxy-2-methylpropoxy, cyano, difluoromethoxy, t-butoxycarbonyl, hydroxy, hydroxymethyl, 2-hydroxyethyl, 2-hydroxy-2-propyl, methoxymethyl, methylsulfonyl, methylsulfonylamino, trifluoromethoxy and 2,2,2-trifluoroethoxy.

$Cy^2$ is benzimidazolyl, benzotriazolyl and piperidinyl each optionally substituted by 1 to 4 groups independently selected from fluorine, chlorine, cyano, hydroxy, amino, $(C_1-C_4)$alkyl, $(C_3-C_4)$cycloalkyl, $(C_3-C_4)$cycloalkyl$(C_1-C_2)$alkyl, $(C_1-C_4)$alkoxy, $(C_1-C_4)$haloalkoxy, $CONH_2$, $(C_1-C_4)$alkylaminocarbonyl, di$(C_1-C_4)$alkylaminocarbonyl, $(C_1-C_4)$alkylcarbonylamino and $(C_1-C_4)$haloalkyl. Alternatively, when $Cy^2$ is piperidinyl, oxo is also a possible substituent.

Alternatively, when $R^3$ is methoxymethyl, $Cy^2$ is (a) halogen or —O—$SO_3$—R; or (b) cycloalkyl, aryl, heterocyclyl or heteroaryl, optionally substituted by 1 to 4 groups independently selected from fluorine, chlorine, cyano, hydroxy, amino, $C_1-C_4$ alkyl, $(C_3-C_4)$cycloalkyl, $(C_3-C_4)$cycloalkyl$(C_1-C_2)$alkyl, $(C_1-C_4)$alkoxy, $(C_1-C_4)$haloalkoxy, $CONH_2$, $(C_1-C_4)$alkylaminocarbonyl, di$(C_1-C_4)$alkylaminocarbonyl and $(C_1-C_4)$alkylcarbonylamino and $C_1-C_4$ haloalkyl; and R is (i) $(C_1-C_4)$alkyl optionally substituted with one or more halogen or (ii) phenyl, optionally substituted with halogen, $(C_1-C_4)$alkyl or $NO_2$;

or a pharmaceutically acceptable salt, enantiomer or diastereomer thereof. Values for the remaining variables are as defined for first second, third, fourth, fifth or sixth embodiment.

In a ninth embodiment, the variables Formula I or any one of Formulas $Ia^{1-10}$-$Ie^{1-5}$ are as defined in the following paragraphs:

$Cy^2$ is benzimidazolyl, benzotriazolyl and piperidinyl each optionally substituted by 1 to 4 groups independently selected from $(C_1$-$C_6)$alkyl, $(C_3$-$C_7)$cycloalkyl, $(C_3$-$C_7)$cycloalkyl$(C_1$-$C_2)$alkyl, $(C_1$-$C_4)$alkanesulfonyl, hydroxy$(C_1$-$C_4)$alkylcarbonyl, tetrahydrofuranylcarbonyl, $CONH_2$, $(C_1$-$C_4)$alkylaminocarbonyl, di$(C_1$-$C_4)$alkylaminocarbonyl, $(C_1$-$C_4)$alkylcarbonyl, $(C_1$-$C_4)$alkoxycarbonyl. Alternatively, when $R^3$ is methoxymethyl, $Cy^2$ is (a) halogen or —O—$SO_3$—R, wherein R is (i) $(C_1$-$C_4)$alkyl optionally substituted with one or more halogen or (ii) phenyl, optionally substituted with halogen, $(C_1$-$C_4)$alkyl or $NO_2$; or (b) cycloalkyl, aryl, heterocyclyl or heteroaryl optionally substituted by 1 to 4 groups independently selected from $(C_1$-$C_6)$alkyl, $(C_3$-$C_7)$cycloalkyl, $(C_3$-$C_7)$cycloalkyl$(C_1$-$C_2)$alkyl, $(C_1$-$C_4)$alkylaminocarbonyl, di$(C_1$-$C_4)$alkylaminocarbonyl, $(C_1$-$C_4)$alkylcarbonyl, $(C_1$-$C_4)$alkoxycarbonyl;

or a pharmaceutically acceptable salt, enantiomer or diastereomer thereof, wherein values for the remaining variables are as defined for first second, third, fourth, fifth, sixth seventh or eighth embodiments.

In a tenth embodiment, the variables in Formula I or any one of Formulas $Ia^{1-10}$-$Ie^{1-5}$ are as defined in the following paragraphs:

$Cy^2$ is benzimidazolyl, benzotriazolyl and piperidinyl each optionally substituted by 1 to 4 groups independently selected from $(C_1$-$C_6)$alkyl, $(C_3$-$C_7)$cycloalkyl, $(C_3$-$C_7)$cycloalkyl$(C_1$-$C_2)$alkyl, $(C_1$-$C_4)$alkylaminocarbonyl, di$(C_1$-$C_4)$alkylaminocarbonyl, $(C_1$-$C_4)$alkylcarbonyl, $(C_1$-$C_4)$alkoxycarbonyl. Alternatively, when $R^3$ is methoxymethyl, $Cy^2$ is (a) halogen or —O—$SO_3$—R, wherein R is (i) $(C_1$-$C_4)$alkyl optionally substituted with one or more halogen or (ii) phenyl, optionally substituted with halogen, $(C_1$-$C_4)$alkyl or $NO_2$; or (b) cycloalkyl, aryl, heterocyclyl or heteroaryl optionally substituted by 1 to 4 groups independently selected from $(C_1$-$C_6)$alkyl, $(C_3$-$C_7)$cycloalkyl, $(C_3$-$C_7)$cycloalkyl$(C_1$-$C_2)$ alkyl, $(C_1$-$C_4)$alkylaminocarbonyl, di$(C_1$-$C_4)$alkylaminocarbonyl, $(C_1$-$C_4)$alkylcarbonyl, $(C_1$-$C_4)$alkoxycarbonyl;

or a pharmaceutically acceptable salt, enantiomer or diastereomer thereof, wherein values for the remaining variables are as defined for first second, third, fourth, fifth, sixth seventh or eighth embodiments.

Another embodiment of the invention is a compound of any one of Formulas $Ia^{1-10}$ or a pharmaceutically acceptable salt, enantiomer or diastereomer thereof; or of any one of Formulas $Iba^{1-10}$ or a pharmaceutically acceptable salt, enantiomer or diastereomer thereof:

$Ia^1$

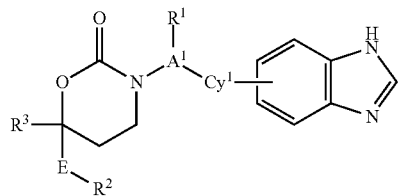

$Ia^2$

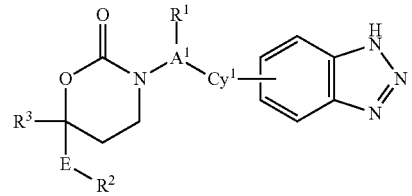

$Ia^3$ $Ia^4$

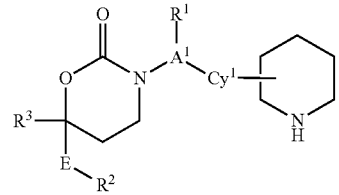

$Ia^5$

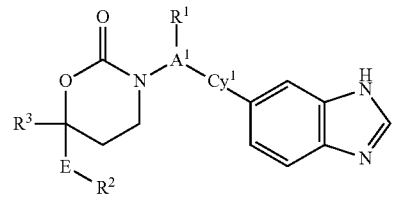

$Ia^6$

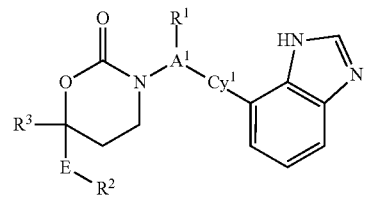

$Ia^7$

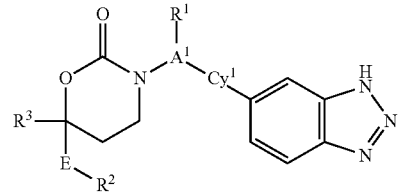

$Ia^8$

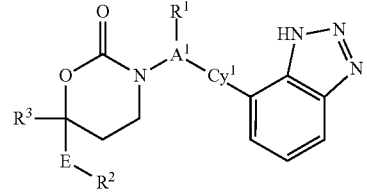

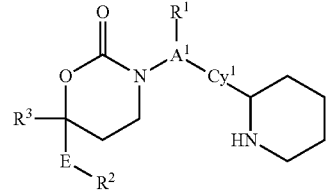

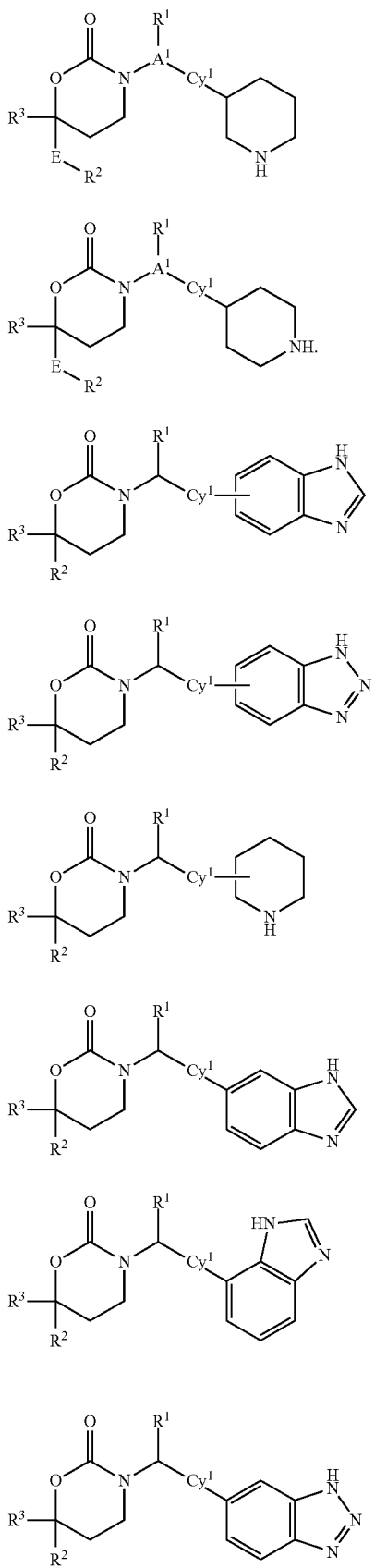
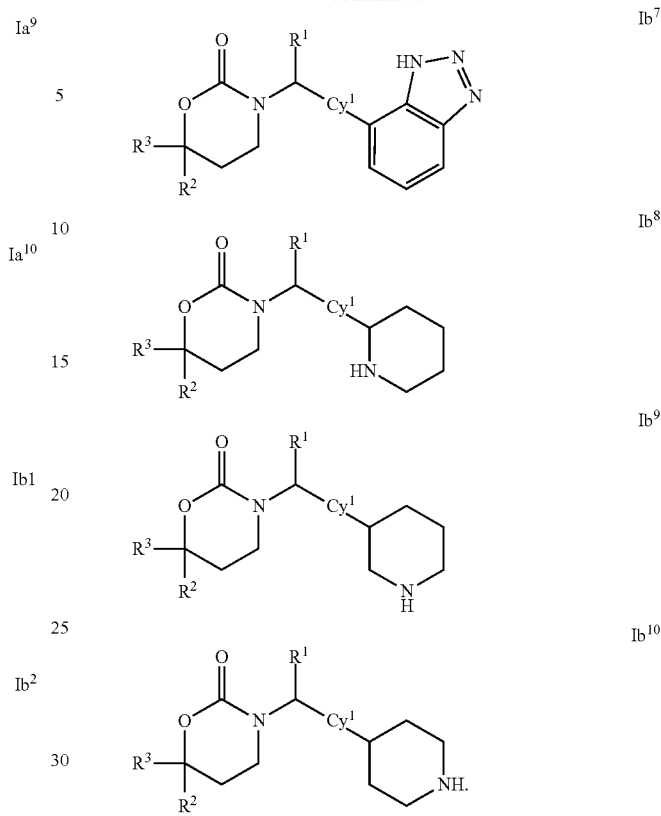

In Formulas Ia$^{1-10}$ and Ib$^{1-10}$, the benzimidazolyl, benzotriazolyl and piperidinyl rings are optionally substituted at each substitutable ring nitrogen atom with ($C_1$-$C_4$)alkyl, ($C_3$-$C_4$)cycloalkyl, ($C_3$-$C_4$)cycloalkyl($C_1$-$C_2$)alkyl, ($C_1$-$C_4$)alkylcarbonyl, ($C_1$-$C_4$)alkoxycarbonyl or ($C_1$-$C_4$)haloalkyl and optionally substituted at each substitutable ring carbon atom with fluorine, chlorine, cyano, hydroxy, amino, ($C_1$-$C_4$)alkyl, ($C_3$-$C_4$)cycloalkyl, ($C_3$-$C_4$)cycloalkyl($C_1$-$C_2$)alkyl, halo($C_1$-$C_4$)alkyl, ($C_1$-$C_4$)alkoxy, ($C_1$-$C_4$)haloalkoxy, ($C_1$-$C_4$)alkanesulfonyl, hydroxy($C_1$-$C_4$)alkylcarbonyl, tetrahydrofuranylcarbonyl, $CONH_2$, ($C_1$-$C_4$)alkylcarbonyl, ($C_1$-$C_4$)alkoxycarbonyl, ($C_1$-$C_4$)alkylaminocarbonyl, di($C_1$-$C_4$)alkylaminocarbonyl or ($C_1$-$C_4$)alkylcarbonylamino Suitable values for the remainder of the variables are as defined in any one of the first, second, third, fourth fifth, sixth, seventh eighth ninth or tenth embodiments.

In another embodiment in Formulas Ia$^{1-10}$ and Ib$^{1-10}$, the benzimidazolyl, benzotriazolyl and piperidinyl rings are optionally substituted at each substitutable ring nitrogen atom with ($C_1$-$C_4$)alkyl, ($C_3$-$C_4$)cycloalkyl, ($C_3$-$C_4$)cycloalkyl ($C_1$-$C_2$)alkyl, ($C_1$-$C_4$)alkylcarbonyl, ($C_1$-$C_4$)alkoxycarbonyl or ($C_1$-$C_4$)haloalkyl and optionally substituted at each substitutable ring carbon atom with fluorine, chlorine, cyano, hydroxy, amino, ($C_1$-$C_4$)alkyl, ($C_3$-$C_4$)cycloalkyl, ($C_3$-$C_4$)cycloalkyl($C_1$-$C_2$)alkyl, halo($C_1$-$C_4$)alkyl, ($C_1$-$C_4$)alkoxy, ($C_1$-$C_4$)haloalkoxy, $CONH_2$, ($C_1$-$C_4$)alkylcarbonyl, ($C_1$-$C_4$) alkoxycarbonyl, ($C_1$-$C_4$)alkylaminocarbonyl, di($C_1$-$C_4$)alkylaminocarbonyl or ($C_1$-$C_4$)alkylcarbonylamino Suitable values for the remainder of the variables are as defined in any one of the first, second, third fourth fifth, sixth, seventh eighth ninth or tenth embodiments.

For each of the embodiments described in the previous two paragraphs, $R^1$ is preferably methyl or ethyl.

Alternatively, for each of the embodiments described in the two paragraphs immediately following Formulas Ia$^{1-10}$ and Ib$^{1-10}$, R$^1$ is preferably methyl or ethyl; and R$^3$ is MeSO$_2$NHCH$_2$CH$_2$CH$_2$, H$_2$NC(=O)CH$_2$CH$_2$, H$_2$NC(=O)CMe$_2$CH$_2$, 3-hydroxypropyl, 3-hydroxy-3-methylbutyl, 2-hydroxyethyl, 2-hydroxy-2-methylpropyl or 2-cyano-2-methylpropyl.

Alternatively, for each of the embodiments described in the two paragraphs immediately following Formulas Ia$^{1-10}$ and Formulas Ib$^{1-10}$, R$^1$ is preferably methyl or ethyl; R$^2$ is isopropyl or phenyl which is optionally substituted with 1, 2 or 3 substituents selected from halo, cyano, CONH$_2$, (C$_1$-C$_4$)alkyl, (C$_1$-C$_4$)haloalkyl and SO$_2$Me; and R$^3$ is MeSO$_2$NHCH$_2$CH$_2$CH$_2$, H$_2$NC(=O)CH$_2$CH$_2$, H$_2$NC(=O)CMe$_2$CH$_2$, 3-hydroxypropyl, 3-hydroxy-3-methylbutyl, 2-hydroxyethyl, 2-hydroxy-2-methylpropyl or 2-cyano-2-methylpropyl.

Alternatively, for each of the embodiments described in the two paragraphs immediately following Formulas Ia$^{1-10}$ and Formulas Ib$^{1-10}$, R$^1$ is preferably methyl or ethyl; R$^2$ is phenyl optionally substituted with 1, 2 or 3 substituents selected from halo, cyano, CONH$_2$, (C$_1$-C$_4$)alkyl, (C$_1$-C$_4$)haloalkyl and SO$_2$Me; and R$^3$ is MeSO$_2$NHCH$_2$CH$_2$CH$_2$, H$_2$NC(=O)CH$_2$CH$_2$, H$_2$NC(=O)CMe$_2$CH$_2$, 3-hydroxypropyl, 3-hydroxy-3-methylbutyl, 2-hydroxyethyl, 2-hydroxy-2-methylpropyl or 2-cyano-2-methylpropyl.

Alternatively, for each of the embodiments described in the two paragraphs immediately following Formulas Ia$^{1-10}$ and Formulas Ib$^{1-10}$, R$^1$ is preferably methyl or ethyl; R$^2$ is isopropyl or phenyl which is optionally substituted with 1, 2 or 3 substituents selected from halo, cyano, CONH$_2$, (C$_1$-C$_4$)alkyl, (C$_1$-C$_4$)haloalkyl and SO$_2$Me; and R$^3$ is H$_2$NC(=O)CMe$_2$CH$_2$, 3-hydroxy-3-methylbutyl, 2-hydroxy-2-methylpropyl or 2-cyano-2-methylpropyl.

Alternatively, for each of the embodiments described in the two paragraphs immediately following Formulas Ia$^{1-10}$ and Formulas Ib$^{1-10}$, R$^1$ is preferably methyl or ethyl; R$^2$ is phenyl optionally substituted with 1, 2 or 3 substituents selected from halo, cyano, CONH$_2$, (C$_1$-C$_4$)alkyl, (C$_1$-C$_4$)haloalkyl and SO$_2$Me; and R$^3$ is H$_2$NC(=O)CMe$_2$CH$_2$, 3-hydroxy-3-methylbutyl, 2-hydroxy-2-methylpropyl or 2-cyano-2-methylpropyl.

Alternatively, for each of the embodiments described in the two paragraphs immediately following Formulas Ia$^{1-10}$ and Formulas Ib$^{1-10}$, R$^1$ is preferably methyl or ethyl; R$^2$ is isopropyl or phenyl which is optionally substituted with 1, 2 or 3 substituents selected from halo, cyano, and (C$_1$-C$_4$)alkyl; and R$^3$ is 2-hydroxy-2-methylpropyl or 2-cyano-2-methylpropyl.

Alternatively, for each of the embodiments described in the two paragraphs immediately following Formulas Ia$^{1-10}$ and Formulas Ib$^{1-10}$, R$^1$ is preferably methyl or ethyl; R$^2$ is phenyl optionally substituted with 1, 2 or 3 substituents selected from halo, cyano, and (C$_1$-C$_4$)alkyl; and R$^3$ is 2-hydroxy-2-methylpropyl or 2-cyano-2-methylpropyl.

Alternatively, for each of the embodiments described in the two paragraphs immediately following Formulas Ia$^{1-10}$ and Formulas Ib$^{1-10}$, R$^1$ is preferably methyl or ethyl; R$^2$ is phenyl optionally substituted with 1, 2 or 3 substituents selected from halo, cyano, CONH$_2$, (C$_1$-C$_4$)alkyl, (C$_1$-C$_4$)haloalkyl and SO$_2$Me; and R$^3$ is 2-hydroxy-2-methylpropyl or 2-cyano-2-methylpropyl.

For each of the embodiments described in the two paragraphs immediately following Formulas Ia$^{1-10}$ and Formulas Ib$^{1-10}$, R$^1$ is preferably methyl or ethyl; R$^2$ is isopropyl, phenyl or fluorophenyl; and R$^3$ is 2-hydroxy-2-methylpropyl or 2-cyano-2-methylpropyl.

For each of the embodiments described in the two paragraphs immediately following Formulas Ia$^{1-10}$ and Formulas Ib$^{1-10}$, R$^1$ is preferably methyl or ethyl; R$^2$ is phenyl or fluorophenyl; and R$^3$ is 2-hydroxy-2-methylpropyl or 2-cyano-2-methylpropyl.

For each of the embodiments described in the two paragraphs immediately following Formulas Ia$^{1-10}$ and Formulas Ib$^{1-10}$, R$^1$ is preferably methyl or ethyl; R$^2$ is isopropyl, phenyl or fluorophenyl; R$^3$ is 2-hydroxy-2-methylpropyl or 2-cyano-2-methylpropyl; substitutable ring nitrogen atoms in the benzimidazolyl and benzotriazolyl rings in Formulas Ib$^{1-10}$ are optionally substituted with (C$_1$-C$_4$)alkyl, (C$_3$-C$_4$)cycloalkyl, (C$_3$-C$_4$)cycloalkyl(C$_1$-C$_2$)alkyl, or (C$_1$-C$_2$)haloalkyl; substitutable ring nitrogen atoms in the piperidinyl rings in Formulas Ib$^{1-10}$ are optionally substituted with (C$_1$-C$_2$)alkanesulfonyl, hydroxy(C$_1$-C$_3$)alkylcarbonyl, tetrahydrofuranylcarbonyl, CONH$_2$, (C$_1$-C$_2$)alkylaminocarbonyl, di(C$_1$-C$_2$)alkylaminocarbonyl, (C$_1$-C$_2$)alkylcarbonyl or (C$_1$-C$_2$)allyl; and one or two substitutable ring carbon atoms in the benzimidazolyl, benzotriazolyl and piperidinyl rings in Formulas Ia$^{1-10}$ and Ib$^{1-10}$ are optionally substituted with methyl or ethyl; and one substitutable ring carbon atoms in piperidinyl rings in Formulas Ia$^{1-10}$ and Ib$^{1-10}$ is optionally substituted with oxo;

For each of the embodiments described in the two paragraphs immediately following Formulas Ia$^{1-10}$ and Formulas Ib$^{1-10}$, R$^1$ is preferably methyl or ethyl; R$^2$ is phenyl or fluorophenyl; R$^3$ is 2-hydroxy-2-methylpropyl or 2-cyano-2-methylpropyl; substitutable ring nitrogen atoms in the benzimidazolyl and benzotriazolyl rings in Formulas Ib$^{1-10}$ are optionally substituted with (C$_1$-C$_4$)alkyl, (C$_3$-C$_4$)cycloalkyl, (C$_3$-C$_4$)cycloalkyl(C$_1$-C$_2$)alkyl, or (C$_1$-C$_2$)haloalkyl; and one or two substitutable ring carbon atoms in the benzimidazolyl, benzotriazolyl and piperidinyl rings in Formulas Ia$^{1-10}$ and Ib$^{1-10}$ are optionally substituted with methyl or ethyl;

For each of the embodiments described in the two paragraphs immediately following Formulas Ia$^{1-10}$ and Formulas Ib$^{1-10}$, R$^1$ is preferably methyl or ethyl; R$^2$ is phenyl or fluorophenyl; R$^3$ is 2-hydroxy-2-methylpropyl or 2-cyano-2-methylpropyl; substitutable ring nitrogen atoms in the benzimidazolyl, benzotriazolyl and piperidinyl rings in Formulas Ib$^{1-10}$ are optionally substituted with (C$_1$-C$_4$)alkyl, (C$_3$-C$_4$)cycloalkyl, (C$_3$-C$_4$)cycloalkyl(C$_1$-C$_2$)alkyl, or (C$_1$-C$_2$)haloalkyl; and one or two substitutable ring carbon atoms in the benzimidazolyl, benzotriazolyl and piperidinyl rings in Formulas Ia$^{1-10}$ and Ib$^{1-10}$ are optionally substituted with methyl or ethyl.

Another embodiment of the invention is a compound of any one for Formulas Ic$^{1-10}$, or a pharmaceutically acceptable salt thereof:

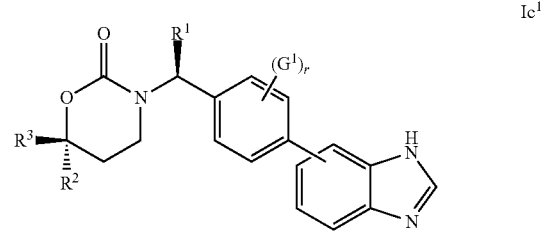

Ic$^1$

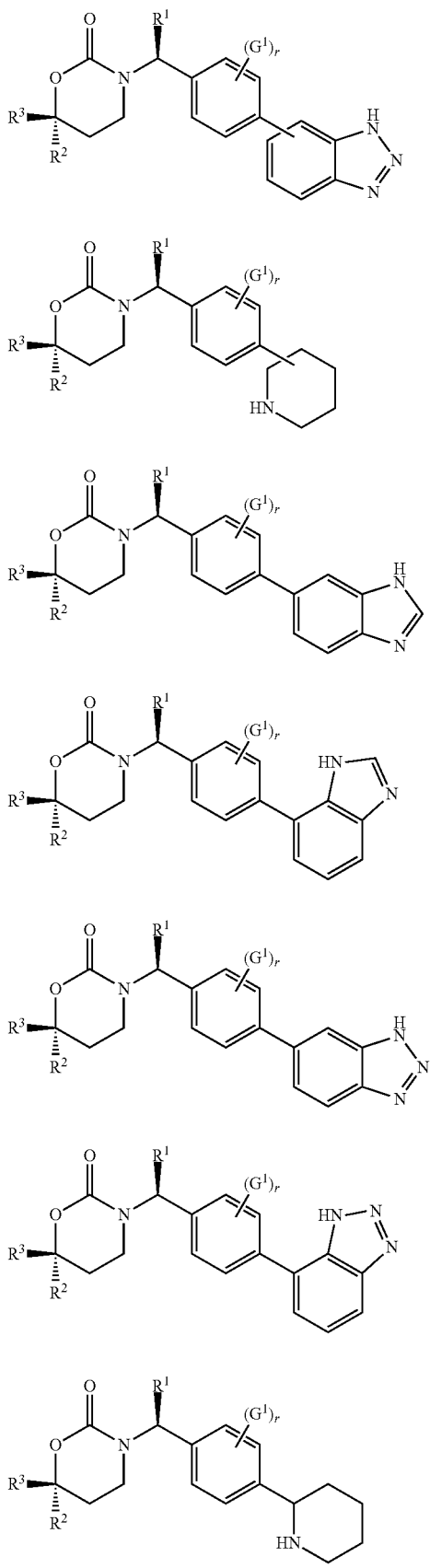
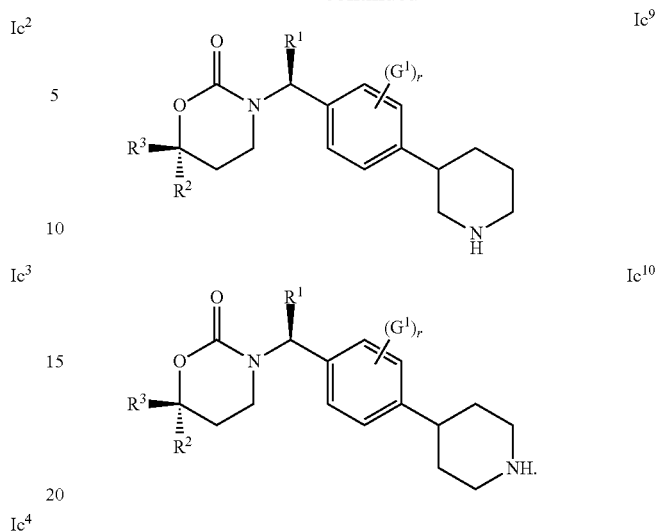

In Formulas Ic$^{1-10}$, the benzimidazolyl, benzotriazolyl and piperidinyl rings are optionally substituted at each substitutable ring nitrogen atom with (C$_1$-C$_4$)alkyl, (C$_3$-C$_4$)cycloalkyl, (C$_3$-C$_4$)cycloalkyl(C$_1$-C$_2$)alkyl, (C$_1$-C$_4$)alkylcarbonyl, (C$_1$-C$_4$)alkoxycarbonyl or (C$_1$-C$_4$)haloalkyl and optionally substituted at each substitutable ring carbon atom with fluorine, chlorine, cyano, hydroxy, amino, (C$_1$-C$_4$)alkyl, (C$_3$-C$_4$)cycloalkyl, (C$_3$-C$_4$)cycloalkyl(C$_1$-C$_2$)alkyl, halo(C$_1$-C$_4$)alkyl, (C$_1$-C$_4$)alkoxy, (C$_1$-C$_4$)haloalkoxy, (C$_1$-C$_4$)alkanesulfonyl, hydroxy(C$_1$-C$_4$)alkylcarbonyl, tetrahydrofuranylcarbonyl, CONH$_2$, (C$_1$-C$_4$)alkylcarbonyl, (C$_1$-C$_4$)alkoxycarbonyl, (C$_1$-C$_4$)alkylaminocarbonyl, di(C$_1$-C$_4$)alkylaminocarbonyl or (C$_1$-C$_4$)alkylcarbonylamino. Suitable values for the remainder of the variables are as defined in any one of the first, second, third, fourth, fifth, sixth, seventh eighth ninth or tenth embodiments.

For each of the embodiments described in the previous paragraph, R$^1$ is preferably methyl or ethyl.

Alternatively, for each of the embodiments described in the paragraph immediately following Formulas Ic$^{1-10}$, R$^1$ is preferably methyl or ethyl; and R$^3$ is MeSO$_2$NHCH$_2$CH$_2$CH$_2$, H$_2$NC(=O)CH$_2$CH$_2$, H$_2$NC(=O)CMe$_2$CH$_2$, 3-hydroxypropyl, 3-hydroxy-3-methylbutyl, 2-hydroxyethyl, 2-hydroxy-2-methylpropyl or 2-cyano-2-methylpropyl.

Alternatively, for each of the embodiments described in the paragraph immediately following Formulas Ic$^{1-10}$, R$^1$ is preferably methyl or ethyl; R$^2$ is isopropyl or phenyl which is optionally substituted with 1, 2 or 3 substituents selected from halo, cyano, CONH$_2$, (C$_1$-C$_4$)alkyl, (C$_1$-C$_4$)haloalkyl and SO$_2$Me; and R$^3$ is MeSO$_2$NHCH$_2$CH$_2$CH$_2$, H$_2$NC(=O)CH$_2$CH$_2$, H$_2$NC(=O)CMe$_2$CH$_2$, 3-hydroxypropyl, 3-hydroxy-3-methylbutyl, 2-hydroxyethyl, 2-hydroxy-2-methylpropyl or 2-cyano-2-methylpropyl.

Alternatively, for each of the embodiments described in the paragraph immediately following Formulas Ic$^{1-10}$, R$^1$ is preferably methyl or ethyl; R$^2$ is isopropyl or phenyl which is optionally substituted with 1, 2 or 3 substituents selected from halo, cyano, CONH$_2$, (C$_1$-C$_4$)alkyl, (C$_1$-C$_4$)haloalkyl and SO$_2$Me; and R$^3$ is H$_2$NC(=O)CMe$_2$CH$_2$, 3-hydroxy-3-methylbutyl, 2-hydroxy-2-methylpropyl or 2-cyano-2-methylpropyl.

Alternatively, for each of the embodiments described in the paragraph immediately following Formulas Ic$^{1-10}$, R$^1$ is preferably methyl or ethyl; R$^2$ is isopropyl or phenyl which is optionally substituted with 1, 2 or 3 substituents selected from halo, cyano, and $(C_1-C_4)$alkyl; and $R^3$ is 2-hydroxy-2-methylpropyl or 2-cyano-2-methylpropyl.

For each of the embodiments described in the paragraph immediately following Formulas $Ic^{1-10}$, $R^1$ is preferably methyl or ethyl; $R^2$ is isopropyl, phenyl or fluorophenyl; and $R^3$ is 2-hydroxy-2-methylpropyl or 2-cyano-2-methylpropyl.

For each of the embodiments described in the paragraph immediately following Formulas $Ic^{1-10}$, $R^1$ is preferably methyl or ethyl; $R^2$ is isopropyl, phenyl or fluorophenyl; $R^3$ is 2-hydroxy-2-methylpropyl or 2-cyano-2-methylpropyl; substitutable ring nitrogen atoms in the benzimidazolyl and benzotriazolyl rings in Formulas $Ic^{1-10}$ are optionally substituted with $(C_1-C_4)$alkyl, $(C_3-C_4)$cycloalkyl, $(C_3-C_4)$cycloalkyl$(C_1-C_2)$alkyl, or $(C_1-C_2)$haloalkyl; substitutable ring nitrogen atoms in the piperidinyl rings in Formulas $Ic^{1-10}$ are optionally substituted with $(C_1-C_2)$alkanesulfonyl, hydroxy$(C_1-C_3)$alkylcarbonyl, tetrahydrofuranylcarbonyl, $CONH_2$, $(C_1-C_2)$alkylaminocarbonyl, di$(C_1-C_2)$alkylaminocarbonyl, $(C_1-C_2)$alkylcarbonyl or $(C_1-C_2)$alkyl; and one or two substitutable ring carbon atoms in the benzimidazolyl, benzotriazolyl and piperidinyl rings in Formulas $Ic^{1-10}$ are optionally substituted with methyl or ethyl; and one substitutable ring carbon atoms in piperidinyl rings in Formulas $Ic^{1-10}$ is optionally substituted with oxo; Alternatively in Formulas $Ic^{1-10}$, the benzimidazolyl, benzotriazolyl and piperidinyl rings are optionally substituted at each substitutable ring nitrogen atom with $(C_1-C_4)$alkyl, $(C_3-C_4)$cycloalkyl, $(C_3-C_4)$cycloalkyl$(C_1-C_2)$alkyl, $(C_1-C_4)$alkylcarbonyl, $(C_1-C_4)$alkoxycarbonyl or $(C_1-C_4)$haloalkyl and optionally substituted at each substitutable ring carbon atom with fluorine, chlorine, cyano, hydroxy, amino, $(C_1-C_4)$alkyl, $(C_3-C_4)$cycloalkyl, $(C_3-C_4)$cycloalkyl$(C_1-C_2)$alkyl, halo$(C_1-C_4)$alkyl, $(C_1-C_4)$alkoxy, $(C_1-C_4)$haloalkoxy, $CONH_2$, $(C_1-C_4)$alkylcarbonyl, $(C_1-C_4)$alkoxycarbonyl, $(C_1-C_4)$alkylaminocarbonyl, di$(C_1-C_4)$alkylaminocarbonyl or $(C_1-C_4)$alkylcarbonylamino; each $G^1$ is independently halogen, cyano, oxo, nitro, hydroxy, amino, $(C_1-C_4)$alkyl, $(C_3-C_4)$cycloalkyl, $(C_3-C_4)$cycloalkyl$(C_1-C_2)$alkyl, halo$(C_1-C_4)$alkyl, $(C_1-C_4)$alkoxy, $(C_1-C_4)$haloalkoxy, $(C_1-C_4)$alkoxycarbonyl, benzoxycarbony, $CONH_2$, $(C_1-C_4)$alkylaminocarbonyl, di$(C_1-C_4)$alkylaminocarbonyl, $(C_3-C_4)$cycloalkylaminocarbonyl, $\{(C_1-C_4)$alkyl$\}\{(C_3-C_4)$cycloalkyl$\}$aminocarbonyl and $(C_1-C_4)$alkylcarbonylamino; r is 0, 1 or 2; and suitable values for the remainder of the variables are as defined in any one of the first, second, third, fourth or fifth, embodiments.

Alternatively, oxo is also a possible substituent for the piperidinyl group in Formulas $Ic^3$, $Ic^{8-10}$.

For each of the embodiments described in the previous paragraph, $R^1$ is preferably methyl or ethyl.

Alternatively, for each of the embodiments described in the paragraph immediately following Formulas $Ic^{1-10}$, $R^1$ is preferably methyl or ethyl; and $R^3$ is $MeSO_2NHCH_2CH_2CH_2$, $H_2NC(=O)CH_2CH_2$, $H_2NC(=O)CMe_2CH_2$, 3-hydroxypropyl, 3-hydroxy-3-methylbutyl, 2-hydroxyethyl, 2-hydroxy-2-methylpropyl or 2-cyano-2-methylpropyl.

Alternatively, for each of the embodiments described in the paragraph immediately following Formulas $Ic^{1-10}$, $R^1$ is preferably methyl or ethyl; $R^2$ is phenyl optionally substituted with 1, 2 or 3 substituents selected from halo, cyano, $CONH_2$, $(C_1-C_4)$alkyl, $(C_1-C_4)$haloalkyl and $SO_2Me$; and $R^3$ is $MeSO_2NHCH_2CH_2CH_2$, $H_2NC(=O)CH_2CH_2$, $H_2NC(=O)CMe_2CH_2$, 3-hydroxypropyl, 3-hydroxy-3-methylbutyl, 2-hydroxyethyl, 2-hydroxy-2-methylpropyl or 2-cyano-2-methylpropyl.

Alternatively, for each of the embodiments described in the paragraph immediately following Formulas $Ic^{1-10}$, $R^1$ is preferably methyl or ethyl; $R^2$ is phenyl optionally substituted with 1, 2 or 3 substituents selected from halo, cyano, $CONH_2$, $(C_1-C_4)$alkyl, $(C_1-C_4)$haloalkyl and $SO_2Me$; and $R^3$ is $H_2NC(=O)CMe_2CH_2$, 3-hydroxy-3-methylbutyl, 2-hydroxy-2-methylpropyl or 2-cyano-2-methylpropyl.

Alternatively, for each of the embodiments described in the paragraph immediately following Formulas $Ic^{1-10}$, $R^1$ is preferably methyl or ethyl; $R^2$ is phenyl optionally substituted with 1, 2 or 3 substituents selected from halo, cyano, $CONH_2$, $(C_1-C_4)$alkyl, $(C_1-C_4)$haloalkyl and $SO_2Me$; and $R^3$ is 2-hydroxy-2-methylpropyl or 2-cyano-2-methylpropyl.

Alternatively, for each of the embodiments described in the paragraph immediately following Formulas $Ic^{1-10}$, $R^1$ is preferably methyl or ethyl; $R^2$ is phenyl or fluorophenyl; and $R^3$ is 2-hydroxy-2-methylpropyl or 2-cyano-2-methylpropyl.

Alternatively, for each of the embodiments described in the paragraph immediately following Formulas $Ic^{1-10}$, $R^1$ is preferably methyl or ethyl; $R^2$ is phenyl or fluorophenyl; $R^3$ is 2-hydroxy-2-methylpropyl or 2-cyano-2-methylpropyl; substitutable ring nitrogen atoms in the benzimidazolyl, benzotriazolyl and piperidinyl rings in Formulas $Ic^{1-10}$ are optionally substituted with $(C_1-C_4)$alkyl, $(C_3-C_4)$cycloalkyl, $(C_3-C_4)$cycloalkyl$(C_1-C_2)$allyl, or $(C_1-C_2)$ haloalkyl; and one or two substitutable ring carbon atoms in the benzimidazolyl, benzotriazolyl and piperidinyl rings in Formulas $Ic^{1-10}$ are optionally substituted with methyl or ethyl.

Another embodiment of the invention is a compound represented by any one of Formulas $Id^{1-7}$, or a pharmaceutically acceptable salt thereof:

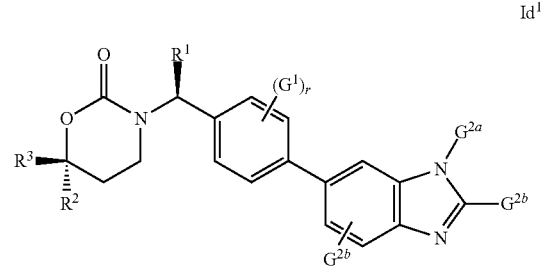

Id¹

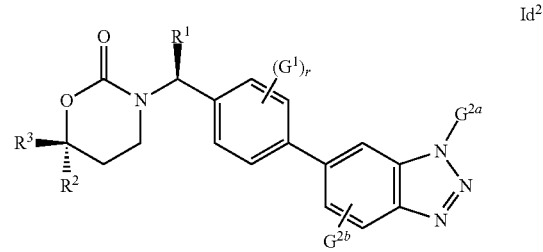

Id²

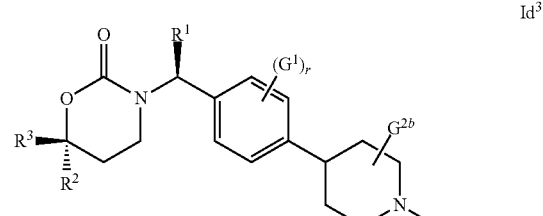

Id³

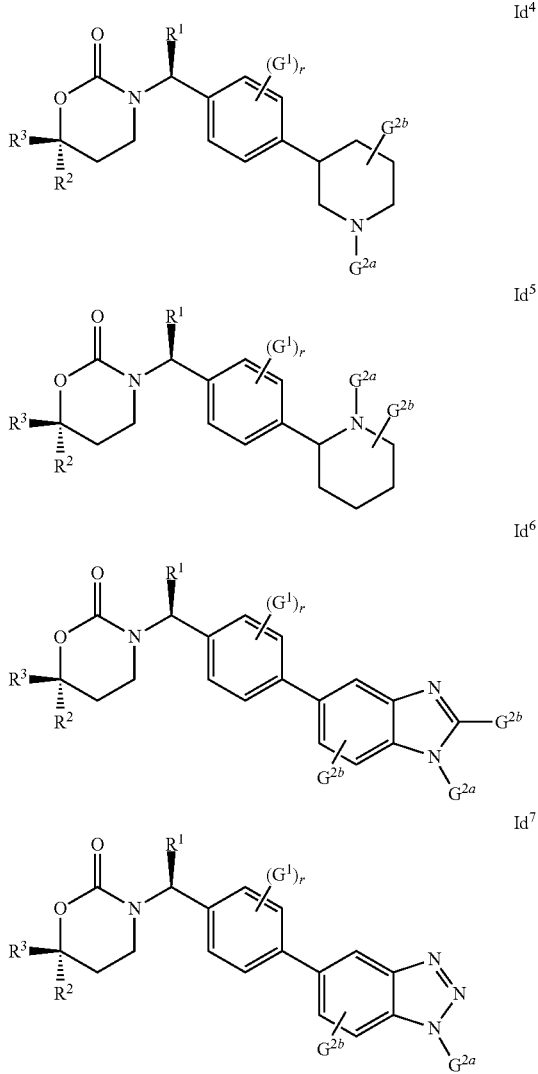

In Formulas Id¹, Id², Id⁶ and Id⁷, $G^1$ is $(C_1-C_4)$alkyl, $(C_1-C_4)$alkoxy, $(C_1-C_4)$haloalkyl, $(C_1-C_4)$haloalkoxy, halogen, cyano or nitro; r is 0, 1 or 2; $G^{2a}$ is $(C_1-C_4)$alkyl, $(C_3-C_4)$cycloalkyl or $(C_1-C_4)$haloalkyl; each $G^{2b}$ is independently hydrogen, fluorine, chlorine, cyano, hydroxy, amino, $(C_1-C_4)$alkyl, $(C_3-C_4)$cycloalkyl, $(C_3-C_4)$cycloalkyl$(C_1-C_2)$alkyl, halo$(C_1-C_4)$alkyl, $(C_1-C_4)$alkoxy, $(C_1-C_4)$haloalkoxy, $CONH_2$, $(C_1-C_4)$alkylaminocarbonyl, di$(C_1-C_4)$alkylaminocarbonyl or $(C_1-C_4)$alkylcarbonylamino; and suitable values for $R^1$, $R^2$ and $R^3$ are as defined in any one of the first, second, third, fourth, fifth, sixth, seventh, eighth, ninth or tenth embodiments, or a pharmaceutically acceptable salt, enantiomer or diastereomer thereof.

In Formulas Id³, Id⁴, and Id⁵, $G^1$ is $(C_1-C_4)$alkyl, $(C_1-C_4)$alkoxy, $(C_1-C_4)$haloalkyl, $(C_1-C_4)$haloalkoxy, halogen, cyano or nitro; r is 0, 1 or 2; $G^{2a}$ is $(C_1-C_4)$alkyl, $(C_1-C_4)$alkanesulfonyl, hydroxy$(C_1-C_4)$alkylcarbonyl, tetrahydrofuranylcarbonyl, $CONH_2$, $(C_1-C_4)$alkylaminocarbonyl, di$(C_1-C_4)$alkylaminocarbonyl, $(C_1-C_4)$alkylcarbonyl, $(C_1-C_4)$alkoxycarbonyl; each $G^{2b}$ is independently hydrogen, fluorine, chlorine, cyano, hydroxy, amino, $(C_1-C_4)$alkyl, $(C_3-C_4)$cycloalkyl, $(C_3-C_4)$cycloalkyl$(C_1-C_2)$alkyl, halo$(C_1-C_4)$alkyl, $(C_1-C_4)$alkoxy, $(C_1-C_4)$haloalkoxy, $CONH_2$, $(C_1-C_4)$alkylaminocarbonyl, di$(C_1-C_4)$alkylaminocarbonyl or $(C_1-C_4)$alkylcarbonylamino; and suitable values for $R^1$, $R^2$ and $R^3$ are as defined in any one of the first, second, third, fourth, fifth, sixth, seventh, eighth, ninth or tenth embodiments, or a pharmaceutically acceptable salt, enantiomer or diastereomer thereof.

For each of the embodiments described in the previous two paragraphs, $R^1$ is preferably methyl or ethyl.

Alternatively, for each of the embodiments described in the two paragraphs immediately following Formulas Id$^{1-7}$, $R^1$ is preferably methyl or ethyl; and $R^3$ is $MeSO_2NHCH_2CH_2CH_2$, $H_2NC(=O)CH_2CH_2$, $H_2NC(=O)CMe_2CH_2$, 3-hydroxypropyl, 3-hydroxy-3-methylbutyl, 2-hydroxyethyl, 2-hydroxy-2-methylpropyl or 2-cyano-2-methylpropyl.

Alternatively, for each of the embodiments described in the two paragraphs immediately following Formulas Id$^{1-7}$, $R^1$ is preferably methyl or ethyl; $R^2$ is isopropyl or phenyl which is optionally substituted with 1, 2 or 3 substituents selected from halo, cyano, $CONH_2$, $(C_1-C_4)$alkyl, $(C_1-C_4)$haloalkyl and $SO_2Me$; and $R^3$ is $MeSO_2NHCH_2CH_2CH_2$, $H_2NC(=O)CH_2CH_2$, $H_2NC(=O)CMe_2CH_2$, 3-hydroxypropyl, 3-hydroxy-3-methylbutyl, 2-hydroxyethyl, 2-hydroxy-2-methylpropyl or 2-cyano-2-methylpropyl. Alternatively, for each of the embodiments described in the two paragraphs immediately following Formulas Id$^{1-7}$, $R^1$ is preferably methyl or ethyl; $R^2$ is phenyl optionally substituted with 1, 2 or 3 substituents selected from halo, cyano, $CONH_2$, $(C_1-C_4)$alkyl, $(C_1-C_4)$haloalkyl and $SO_2Me$; and $R^3$ is $MeSO_2NHCH_2CH_2CH_2$, $H_2NC(=O)CH_2CH_2$, $H_2NC(=O)CMe_2CH_2$, 3-hydroxypropyl, 3-hydroxy-3-methylbutyl, 2-hydroxyethyl, 2-hydroxy-2-methylpropyl or 2-cyano-2-methylpropyl.

Alternatively, for each of the embodiments described in the two paragraphs immediately following Formulas Id$^{1-7}$, $R^1$ is preferably methyl or ethyl; $R^2$ is isopropyl or phenyl which is optionally substituted with 1, 2 or 3 substituents selected from halo, cyano, $CONH_2$, $(C_1-C_4)$alkyl, $(C_1-C_4)$haloalkyl and $SO_2Me$; and $R^3$ is $H_2NC(=O)CMe_2CH_2$, 3-hydroxy-3-methylbutyl, 2-hydroxy-2-methylpropyl or 2-cyano-2-methylpropyl. Alternatively, for each of the embodiments described in the two paragraphs immediately following Formulas Id$^{1-7}$, $R^1$ is preferably methyl or ethyl; $R^2$ is phenyl optionally substituted with 1, 2 or 3 substituents selected from halo, cyano, $CONH_2$, $(C_1-C_4)$alkyl, $(C_1-C_4)$haloalkyl and $SO_2Me$; and $R^3$ is $H_2NC(=O)CMe_2CH_2$, 3-hydroxy-3-methylbutyl, 2-hydroxy-2-methylpropyl or 2-cyano-2-methylpropyl.

Alternatively, for each of the embodiments described in the two paragraphs immediately following Formulas Id$^{1-7}$, $R^1$ is preferably methyl or ethyl; $R^2$ is isopropyl or phenyl which is optionally substituted with 1, 2 or 3 substituents selected from halo, cyano and $(C_1-C_4)$alkyl; and $R^3$ is 2-hydroxy-2-methylpropyl or 2-cyano-2-methylpropyl.

Alternatively, for each of the embodiments described in the two paragraphs immediately following Formulas Id$^{1-7}$, $R^1$ is preferably methyl or ethyl; $R^2$ is phenyl optionally substituted with 1, 2 or 3 substituents selected from halo, cyano and $(C_1-C_4)$alkyl; and $R^3$ is 2-hydroxy-2-methylpropyl or 2-cyano-2-methylpropyl.

Alternatively, for each of the embodiments described in the two paragraphs immediately following Formulas Id$^{1-7}$, $R^1$ is preferably methyl or ethyl; $R^2$ is phenyl optionally substituted with 1, 2 or 3 substituents selected from halo, cyano, $CONH_2$ and $(C_1-C_4)$alkyl, $(C_1-C_4)$haloalkyl and $SO_2Me$; and $R^3$ is 2-hydroxy-2-methylpropyl or 2-cyano-2-methylpropyl.

Alternatively, for each of the embodiments described in the two paragraphs immediately following Formulas Id$^{1-7}$, $R^1$ is preferably methyl or ethyl; $R^2$ is isopropyl, phenyl or fluorophenyl; and $R^3$ is 2-hydroxy-2-methylpropyl or 2-cyano-2-methylpropyl.

Alternatively, for each of the embodiments described in the two paragraphs immediately following Formulas $Id^{1-7}$, $R^1$ is preferably methyl or ethyl; $R^2$ is phenyl or fluorophenyl; and $R^3$ is 2-hydroxy-2-methylpropyl or 2-cyano-2-methylpropyl.

Alternatively, for each of the embodiment described in the two paragraphs immediately following Formulas $Id^{1-7}$, $R^1$ is preferably methyl or ethyl; $R^2$ is isopropyl, phenyl or fluorophenyl; $R^3$ is 2-hydroxy-2-methylpropyl or 2-cyano-2-methylpropyl; the substituent $G^{2a}$ is selected from $(C_1-C_4)$alkyl, $(C_3-C_4)$cycloalkyl, $(C_3-C_4)$cycloalkyl$(C_1-C_2)$alkyl, and $(C_1-C_2)$haloalkyl; and each $G^{2b}$ is independently selected from hydrogen, methyl or ethyl.

Alternatively, for each of the embodiment described in the two paragraphs immediately following Formulas $Id^{1-7}$, $R^1$ is preferably methyl or ethyl; $R^2$ is phenyl or fluorophenyl; $R^3$ is 2-hydroxy-2-methylpropyl or 2-cyano-2-methylpropyl; the substituent $G^{2a}$ is selected from $(C_1-C_4)$alkyl, $(C_3-C_4)$cycloalkyl, $(C_3-C_4)$cycloalkyl$(C_1-C_2)$alkyl, and $(C_1-C_2)$haloalkyl; and each $G^{2b}$ is independently selected from hydrogen, methyl or ethyl.

Alternatively, for each of the embodiments described in the two paragraphs immediately following Formulas $Id^{1-7}$, $R^1$ is preferably methyl or ethyl; $R^2$ is isopropyl, phenyl or fluorophenyl; $R^3$ is 2-hydroxy-2-methylpropyl or 2-cyano-2-methylpropyl; in Formulas $Id^1$, $Id^2$, $Id^6$ and $Id^7$, the substituent $G^{2a}$ is selected from selected from hydrogen, methyl or ethyl; and each $G^{2b}$ is independently selected from hydrogen or methyl.

Alternatively, for each of the embodiment described in the two paragraphs immediately following Formulas $Id^{1-7}$, $R^1$ is preferably methyl or ethyl; $R^2$ is isopropyl, phenyl or fluorophenyl; $R^3$ is 2-hydroxy-2-methylpropyl or 2-cyano-2-methylpropyl; in Formulas $Id^3$, $Id^4$, and $Id^5$ the substituent $G^{2a}$ is selected from hydrogen, methyl, methanesulfonyl, acetyl, tetrahydrofuranylcarbonyl, methoxycarbonyl, methylaminocarbonyl and dimethylaminocarbonyl; and each $G^{2b}$ is independently selected from hydrogen or methyl.

Another embodiment of the invention is a compound represented by Formula $Ie^1$ or a pharmaceutically acceptable salt thereof:

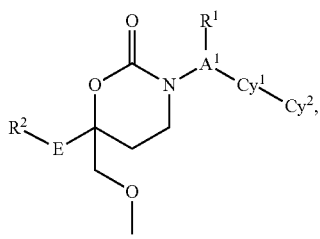

$Ie^1$ $Cy^2$ is (a) halogen or —O—$SO_3$—R; or (b) cycloalkyl, aryl, heterocyclyl or heteroaryl, optionally substituted with 1 to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_3-C_7)$cycloalkyl$(C_1-C_2)$alkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_3-C_7)$cycloalkyl$(C_1-C_2)$alkyl, $(C_1-C_6)$alkoxy, $(C_3-C_6)$cycloalkoxy, $(C_3-C_7)$ cycloalkyl$(C_1-C_2)$alkoxy, halo$(C_1-C_6)$alkoxy, halo$(C_3-C_6)$cycloalkoxy, halo$(C_3-C_7)$cycloalkyl$(C_1-C_2)$alkoxy, $(C_1-C_6)$alkylthio, $(C_3-C_6)$cycloalkythio, $(C_3-C_7)$cycloalkyl$(C_1-C_2)$alkylthio, halo$(C_1-C_6)$alkylthio, halo$(C_3-C_6)$cycloalkythio, halo$(C_3-C_7)$cycloalkyl$(C_1-C_2)$alkylthio, $(C_1-C_6)$alkanesulfinyl, $(C_3-C_6)$cycloalkanesulfinyl, $(C_3-C_7)$cycloalkyl$(C_1-C_2)$alkanesulfinyl, halo$(C_1-C_6)$alkanesulfinyl, halo$(C_3-C_6)$cycloalkanesulfinyl, halo$(C_3-C_7)$cycloalkyl$(C_1-C_2)$alkanesulfinyl, $(C_1-C_6)$alkanesulfonyl, $(C_3-C_6)$cycloalkanesulfonyl, $(C_3-C_7)$cycloalkyl$(C_1-C_2)$alkanesulfonyl, halo$(C_1-C_6)$alkanesulfonyl, halo$(C_3-C_6)$cycloalkanesulfonyl, halo$(C_3-C_7)$cycloalkyl$(C_1-C_2)$alkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclylsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, amino$(C_1-C_6)$alkyl, $(C_1-C_6)$alkylamino$(C_1-C_6)$alkyl, di$(C_1-C_6)$alkylamino$(C_1-C_6)$alkylamino$(C_2-C_6)$alkoxy, $(C_1-C_6)$alkylamino$(C_2-C_6)$alkoxy, di$(C_1-C_6)$alkylamino$(C_2-C_6)$alkoxy, $(C_1-C_6)$alkylcarbonyl, $(C_3-C_6)$cycloalkylcarbonyl, $(C_3-C_6)$cycloalkylaminocarbonyl, {$(C_3-C_6)$cycloalkyl}{$(C_1-C_6)$alkyl}aminocarbonyl, di$(C_3-C_6)$cycloalkylaminocarbonyl, $(C_3-C_6)$cycloalkylaminosulfonyl, {$(C_3-C_6)$cycloalkyl}{$(C_1-C_6)$alkyl}aminosulfonyl, di$(C_3-C_6)$cycloalkylaminosulfonyl, cyano$(C_1-C_6)$alkyl, aminocarbonyl$(C_1-C_6)$alkyl, $(C_1-C_6)$alkylaminocarbonyl$(C_1-C_6)$alkyl, di$(C_1-C_6)$alkylaminocarbonyl$(C_1-C_6)$alkyl, $(C_3-C_6)$cycloalkylaminocarbonyl$(C_1-C_6)$alkyl, {$(C_3-C_6)$cycloalkyl}{$(C_1-C_6)$alkyl}aminocarbonyl$(C_1-C_6)$alkyl and di$(C_3-C_6)$cycloalkylaminocarbonyl$(C_1-C_6)$alkyl; R is (i) $(C_1-C_4)$alkyl optionally substituted with one or more halogen or (ii) phenyl, optionally substituted with halogen, $(C_1-C_4)$alkyl or $NO_2$; the phenyl ring is optionally substituted with $(C_1-C_4)$alkyl, $(C_1-C_4)$alkoxy, $(C_1-C_4)$haloalkyl, $(C_1-C_4)$ haloalkoxy, halogen, cyano and nitro; and suitable values for the remainder of the variables are as defined in any one of the first, second, third, fourth or fifth embodiments.

For each of the embodiments described in the previous paragraph, $R^1$ is preferably methyl or ethyl.

Another embodiment of the invention is a compound represented by any one of Formulas $Ie^{2-5}$, or a pharmaceutically acceptable salt thereof:

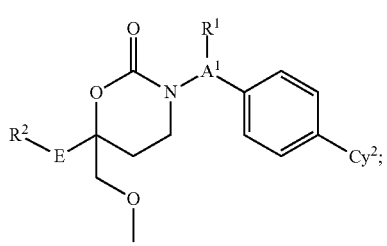

$Ie^2$

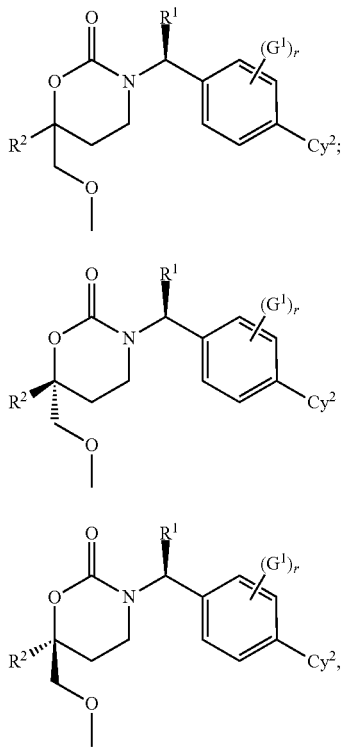

r is 0, 1, 2 or 3; each $G^1$ is independently $(C_1-C_4)$alkyl, $(C_1-C_4)$alkoxy, $(C_1-C_4)$haloalkyl, $(C_1-C_4)$haloalkoxy, halogen, cyano and nitro; suitable substituents for the group represented by $Cy^2$ are as described for Formula $Ie^1$ and suitable values for the remainder of the variables are as defined for the variables in Formula $Ie^1$.

For each of the embodiments described in the paragraph immediately following Formulas $Ie^{1-5}$, $Cy^2$ is preferably phenyl, thienyl, pyridyl, piperidinyl, piperazinyl, morpholinyl, thiazolyl, oxadiazolyl, thiadiazolyl, pyrazolyl, 1,2,3-triazolyl, 1,2,4-triazolyl, tetrazolyl, pyridazinyl, pyrimidinyl, pyrazinyl, benzimidazolyl, benztriazolyl, oxodihydropyridyl, oxodihydropyridazinyl, oxodihydropyrimidinyl and oxodihydropyrazinyl, each optionally substituted by 1 to 4 groups, wherein suitable substituents for a substitutable ring nitrogen atom are selected from $(C_1-C_4)$alkyl, $(C_3-C_4)$cycloalkyl, $(C_3-C_4)$cycloalkyl$(C_1-C_2)$alkyl, $(C_1-C_4)$halo alkyl, $(C_1-C_4)$alkoxycarbonyl, $(C_1-C_4)$alkylcarbonyl and benzyloxycarbonyl; and suitable substituents for a ring carbon atom in the are selected from fluorine, chlorine, cyano, hydroxy, amino, $(C_1-C_4)$alkyl, $(C_3-C_4)$cycloalkyl, $(C_3-C_4)$cycloalkyl $(C_1-C_2)$alkyl, halo$(C_1-C_4)$alkyl, $(C_1-C_4)$alkoxy, $(C_1-C_4)$haloalkoxy, $CONH_2$, $(C_1-C_4)$alkylaminocarbonyl, di$(C_1-C_4)$alkylaminocarbonyl and $(C_1-C_4)$alkylcarbonylamino.

Alternatively, for each of the embodiments described in the paragraph immediately following Formulas $Ie^{1-5}$, preferably $Cy^2$ is as described in the previous paragraph, and $R^2$ is phenyl, thienyl, or pyridyl, each optionally substituted with halogen, nitro, cyano, $(C_1-C_6)$alkyl, halo$(C_1-C_6)$alkyl, hydroxy$(C_1-C_3)$alkyl, $(C_1-C_3)$alkoxy, halo$(C_1-C_3)$alkoxy, $CONH_2$ and $SO_2Me$.

For each of the embodiments described in the paragraph immediately following Formulas $Ie^{1-5}$, preferably $Cy^2$ is as described in the previous paragraph, $R^2$ is phenyl, thienyl, or pyridyl, each optionally substituted with halogen, nitro, cyano, $(C_1-C_6)$alkyl, halo$(C_1-C_6)$alkyl, hydroxy$(C_1-C_3)$alkyl, $(C_1-C_3)$alkoxy, halo$(C_1-C_3)$alkoxy, $CONH_2$ and $SO_2Me$, and $R^1$ is methyl or ethyl. More preferably, $R^2$ is phenyl optionally substituted with 1, 2 or 3 substituents selected from halo, cyano, $CONH_2$, $(C_1-C_4)$alkyl, $(C_1-C_4)$haloalkyl and $SO_2Me$.

For the embodiments described in the previous paragraph, $R^2$ is more preferably phenyl or fluorophenyl.

The present invention further provides methods of inhibiting 11β-HSD1 by contacting 11β-HSD1 with a compound of Formula I, $Ia^{1-10}$, $Ib^{1-10}$, $Ic^{1-10}$, $Id^{1-7}$, $Ie^{1-5}$ of the invention.

The present invention further provides methods of inhibiting or reducing the conversion of cortisone to cortisol in a cell using a compound of Formula I, $Ia^{1-10}$, $Ib^{1-10}$, $Ic^{1-10}$, $Id^{1-7}$ or $Ie^{1-5}$ of the invention.

The present invention further provides methods of inhibiting or reducing production of cortisol in a cell using a compound of Formula I, $Ia^{1-10}$, $Ib^{1-10}$, $Ic^{1-10}$, $Id^{1-7}$ or $Ie^{1-5}$ of the invention.

The present invention further provides methods of increasing insulin sensitivity in a subject in need thereof using a compound of Formula I, $Ia^{1-10}$, $Ib^{1-10}$, $Ic^{1-10}$, $Id^{1-7}$ or $Ie^{1-5}$ of the invention.

The present invention further provides methods of treating a subject with a disease associated with activity of expression of 11β-HSD1 using a compound of Formula I, $Ia^{1-10}$, $Ib^{1-10}$, $Ic^{1-10}$, $Id^{1-7}$ or $Ie^{1-5}$ of the invention.

Preferred values for the variables in the above-described structural formulas I, $Ia^{1-10}$, $Ib^{1-10}$, $Ic^{1-10}$, $Id^{1-7}$ or $Ie^{1-5}$ are provided below:

DEFINITIONS

The term "alkyl" means a straight or branched hydrocarbon radical having 1-10 carbon atoms and includes, for example, methyl, ethyl, n-propyl, isopropyl, n-butyl, sec-butyl, isobutyl, tert-butyl, n-pentyl, n-hexyl, n-heptyl, n-octyl, n-nonyl, n-decyl and the like.

The term "cycloalkyl" means a monocyclic, bicyclic or tricyclic, saturated hydrocarbon ring having 3-10 carbon atoms and includes, for example, cyclopropyl (c-Pr), cyclobutyl, cyclopentyl, cyclohexyl, cycloheptyl, cyclooctyl, bicyclo[2.2.2]octyl, bicyclo[2.2.1]heptyl, spiro[4.4]nonane, adamantyl and the like.

The term "aryl" means an aromatic radical which is a phenyl group, a naphthyl group, an indanyl group or a tetrahydronaphthalene group. When substituted, an aryl group has 1-4 substituents. Exemplary substituents include alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido.

The term "heteroaryl" means a 5- and 6-membered heteroaromatic radical which may optionally be fused to a saturated or unsaturated ring containing 0-4 heteroatoms selected from N, O, and S and includes, for example, a heteroaromatic radical which is 2- or 3-thienyl, 2- or 3-furanyl, 2- or 3-pyrrolyl, 2-, 3-, or 4-pyridyl, 2-pyrazinyl, 2-, 4-, or 5-pyrimidinyl, 3- or 4-pyridazinyl, 1H-indol-6-yl, 1H-indol-5-yl, 1H-benzimidazol-6-yl, 1H-benzimidazol-5-yl, 2-, 4-, 5-, 6-, 7- or 8-quinazolinyl, 2-, 3-, 5-, 6-, 7- or 8-quinoxalinyl, 2-, 3-, 4-, 5-, 6-, 7- or 8-quinolinyl, 1-, 3-, 4-, 5-, 6-, 7- or 8-isoquinolinyl, 2-, 4-, or 5-thiazolyl, 2-, 3-, 4-, or 5-pyrazolyl, 2-, 3-, 4-, or 5-imidazolyl. Exemplary substituents for a substituted heteroaryl include alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido, or by oxo to form an N-oxide.

The term "heterocyclyl" means a 4-, 5-, 6- and 7-membered saturated or partially unsaturated heterocyclic ring containing 1 to 4 heteroatoms independently selected from N, O, and S. Exemplary heterocyclyls include pyrrolidine, 1-methylpyrrolidine, pyrrolidin-2-one, 1-methylpyrrolidin-2-one, piperidine, piperidin-2-one, dihydropyridine, tetrahydropyridine, piperazine, 1-(2,2,2-trifluoroethyl)piperazine, 1,2-dihydro-2-oxopyridine, 1,4-dihydro-4-oxopyridine, piperazin-2-one, 3,4,5,6-tetrahydro-4-oxopyrimidine, 3,4-dihydro-4-oxopyrimidine, tetrahydrofuran, tetrahydropyran, tetrahydrothiophene, tetrahydrothiopyran, isoxazolidine, 1,3-dioxolane, 1,3-dithiolane, 1,3-dioxane, 1,4-dioxane, 1,3-dithiane, 1,4-dithiane, oxazolidin-2-one, imidazolidin-2-one, imidazolidine-2,4-dione, tetrahydropyrimidin-2(1H)-one, morpholine, N-methylmorpholine, morpholin-3-one, 1,3-oxazinan-2-one, thiomorpholine, thiomorpholine 1,1-dioxide, tetrahydro-1,2,5-thiaoxazole 1,1-dioxide, tetrahydro-2H-1,2-thiazine 1,1-dioxide, hexahydro-1,2,6-thiadiazine 1,1-dioxide, tetrahydro-1,2,5-thiadiazole 1,1-dioxide isothiazolidine 1,1-dioxide, 6-oxo-1,6-dihydropyridazin-3-yl, 6-oxo-1,6-dihydropyridazin-4-yl, 5-oxo-4,5-dihydro-1H-1,2,4-triazol-3-yl and 5-oxo-4,5-dihydro-1H-imidazol-2-yl. When substituted, a heterocyclyl has 1-4 substituents. Exemplary substituents include alkyl, haloalkyl, halogen and oxo.

"Substitutable ring nitrogen atom" refers to a ring nitrogen atom in a heteroaryl or heterocyclyl group that is bonded to a hydrogen atom. The hydrogen atom can be replaced, i.e., substituted, with a substituent. A "substitutable ring carbon atom" refers to a carbon atom in an aryl or cycloalkyl that is bonded to a hydrogen atom. The hydrogen atom can be replaced, i.s., substituted, with a substituent.

The term "spirocycloalkyl" means a cycloalkyl group which shares one ring carbon with another alkyl or cycloalkyl group.

As used herein the terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

When a disclosed compound or its pharmaceutically acceptable salt is named or depicted by structure, it is to be understood that solvates or hydrates of the compound or its pharmaceutically acceptable salts are also included. "Solvates" refer to crystalline forms wherein solvent molecules are incorporated into the crystal lattice during crystallization. Solvate may include water or nonaqueous solvents such as ethanol, isopropanol, DMSO, acetic acid, ethanolamine, and EtOAc. Solvates, wherein water is the solvent molecule incorporated into the crystal lattice, are typically referred to as "hydrates." Hydrates include stoichiometric hydrates as well as compositions containing variable amounts of water.

Certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms. The symbol "*" in a structural formula represents the presence of a chiral carbon center. "R" and "S" represent the configuration of substituents around one or more chiral carbon atoms. Thus, "R*" and "S*" denote the relative configurations of substituents around one or more chiral carbon atoms.

"Racemate" or "racemic mixture" means a compound of equimolar quantities of two enantiomers, wherein such mixtures exhibit no optical activity; i.e., they do not rotate the plane of polarized light.

"Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration.

"R," "S," "S*," "R*," "E," "Z," "cis," and "trans," indicate configurations relative to the core molecule.

Tautomeric forms exist when a compound is a mixture of two or more structurally distinct compounds that are in rapid equilibrium. Certain compounds of the invention exist as tautomeric forms. For example, the following compound represented by Structural Formula (A) and (B) include at least the following tautomers forms:

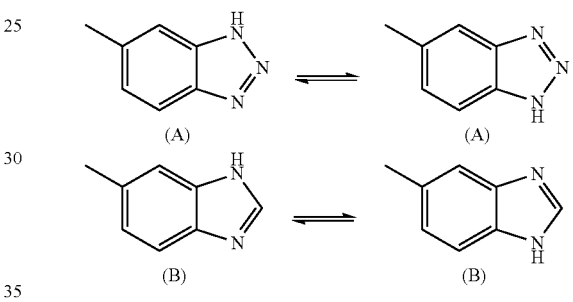

It is to be understood that when one tautormeric form of a compound is depicted by name or structure, all tautomeric forms of the compound are included.

The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

When the stereochemistry of a disclosed compound is named or depicted by structure, the named or depicted stereoisomer is at least 60%, 70%, 80%, 90%, 99% or 99.9% by weight pure relative to the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enantiomer over the weight of the enantiomer plus the weight of its optical isomer.

When a disclosed compound is named or depicted by structure without indicating the stereochemistry, and the compound has at least one chiral center, it is to be understood that the name or structure encompasses one enantiomer of compound free from the corresponding optical isomer, a racemic mixture of the compound and mixtures enriched in one enantiomer relative to its corresponding optical isomer.

When a disclosed compound is named or depicted by structure without indicating the stereochemistry and has at least two chiral centers, it is to be understood that the name or structure encompasses a diastereomer free of other diastereomers, a pair of diastereomers free from other diastereomeric pairs, mixtures of diastereomers, mixtures of diastereomeric pairs, mixtures of diastereomers in which one diastereomer is enriched relative to the other diastereomer(s) and mixtures of diastereomeric pairs in which one diastereomeric pair is enriched relative to the other diastereomeric pair(s).

The compounds of the invention may be present in the form of pharmaceutically acceptable salts. For use in medicines, the salts of the compounds of the invention refer to non-toxic "pharmaceutically acceptable salts." Pharmaceutically acceptable salt forms include pharmaceutically acceptable acidic/anionic or basic/cationic salts.

Pharmaceutically acceptable basic/cationic salts include, the sodium, potassium, calcium, magnesium, diethanolamine, n-methyl-D-glucamine, L-lysine, L-arginine, ammonium, ethanolamine, piperazine and triethanolamine salts.

Pharmaceutically acceptable acidic/anionic salts include, the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, malonate, mandelate, mesylate, methylsulfate, mucate, napsylate, nitrate, pamoate, pantothenate, phosphate/diphospate, polygalacturonate, salicylate, stearate, subacetate, succinate, sulfate, hydrogensulfate, tannate, tartrate, teoclate, tosylate, and triethiodide salts.

The following abbreviations have the indicated meanings:

| Abbreviation | Meaning |
| --- | --- |
| A % | Area percentage |
| Boc | tert-butoxy carbonyl or t-butoxy carbonyl |
| (Boc)$_2$O | di-tert-butyl dicarbonate |
| Cbz | Benzyloxycarbonyl |
| CbzCl | Benzyl chloroformate |
| c-Pr | cyclopropyl |
| DAST | diethylaminosulfur trifluoride |
| DBU | 1,8-diazabicyclo[5.4.0]undec-7-ene |
| DCC | N,N'-dicyclohexylcarbodiimide |
| DCU | N,N'-dicyclohexylurea |
| DIAD | diisopropyl azodicarboxylate |
| DIBAL-H | diisobutylaluminum hydride |
| DIEA | N,N-diisopropylethylamine |
| DMAP | 4-(dimethylamino)pyridine |
| DMF | N,N-dimethylformamide |
| DMPU | 1,3-dimethyl-3,4,5,6-tetrahydro-2(1H)-pyrimidinone |
| 2,4-DNP | 2,4-dinitrophenylhydrazine |
| DPTBS | Diphenyl-t-butylsilyl |
| dr | diastereomer ratio |
| EDC•HCl, EDCI | 1-[3-(dimethylamino)propyl]-3-ethylcarbodiimide hydrochloride |
| Equiv | equivalents |
| EtOAc | ethyl acetate |
| Fmoc | 1-[[(9H-fluoren-9-ylmethoxy)carbonyl]oxy]- |
| Fmoc—OSu | 1-[[(9H-fluoren-9-ylmethoxy)carbonyl]oxy]-2,5-pyrrolidinedione |
| h, hr | hour(s) |
| HOBt | 1-hydroxybenzotriazole |
| HATU | 2-(7-Aza-1H-benzotriazole-1-yl)-1,1,3,3-tetramethyluronium hexafluorophosphate |
| HBTU | 2-(1H-Benzotriazol-1-yl)-1,1,3,3-tetramethyluronium hexafluorophosphate |
| KHMDS | potassium hexamethyldisilazane |

-continued

| Abbreviation | Meaning |
| --- | --- |
| LAH or LiAlH$_4$ | lithium aluminum hydride |
| LC-MS | liquid chromatography-mass spectroscopy |
| LHMDS | lithium hexamethyldisilazane |
| m-CPBA | meta-chloroperoxybenzoic acid |
| Me | methyl |
| MsCl | methanesulfonyl chloride |
| Min | minute |
| MS | mass spectrum |
| NaH | sodium hydride |
| NaHCO$_3$ | sodium bicarbonate |
| NaN$_3$ | sodium azide |
| NaOH | sodium hydroxide |
| Na$_2$SO$_4$ | sodium sulfate |
| NMM | N-methylmorpholine |
| NMP | N-methylpyrrolidinone |
| Pd$_2$(dba)$_3$ | tris(dibenzylideneacetone)dipalladium(0) |
| PE | petroleum ether |
| Quant | quantitative yield |
| rt | room temperature |
| Satd | saturated |
| SOCl$_2$ | thionyl chloride |
| SFC | supercritical fluid chromatography |
| SPA | scintillation proximity assay |
| SPE | solid phase extraction |
| TBAF | tetrabutylammonium fluoride |
| TBS | t-butyldimethylsilyl |
| TBDPS | t-butyldiphenylsilyl |
| TBSCl | t-butyldimethylsilyl chloride |
| TBDPSCl | t-butyldiphenylsilyl chloride |
| TEA | triethylamine or Et$_3$N |
| TEMPO | 2,2,6,6-tetramethyl-1-piperidinyloxy free radical |
| Teoc | 1-[2-(trimethylsilyl)ethoxycarbonyloxy]- |
| Teoc-OSu | 1-[2-(trimethylsilyl)ethoxycarbonyloxy]pyrrolidin-2,5-dione |
| T$_{ext}$ | External temperature |
| T$_{int}$ | Internal temperature |
| TFA | trifluoroacetic acid |
| Tlc, TLC | thin layer chromatography |
| TMS | trimethylsilyl |
| TMSCl | chlorotrimethylsilane or trimethylsilyl chloride |
| t$_R$ | retention time |
| TsOH | p-toluenesulfonic acid |

General Description of Synthetic Methods

Compounds of Formula I can be prepared by several processes. In the discussion below, $A^1$, $Cy^1$, $Cy^2$, E, $R^1$, $R^2$, $R^3$, Y and n have the meanings indicated above unless otherwise noted. In cases where the synthetic intermediates and final products of Formulas I described below contain potentially reactive functional groups, for example amino, hydroxyl, thiol and carboxylic acid groups, that may interfere with the desired reaction, it may be advantageous to employ protected forms of the intermediate. Methods for the selection, introduction and subsequent removal of protecting groups are well known to those skilled in the art (see e.g. T. W. Greene and P. G. M. Wuts "Protective Groups in Organic Synthesis" John Wiley & Sons, Inc., New York 1999). Such protecting group manipulations are assumed in the discussion below and not described explicitly. Generally, reagents in the reaction schemes are used in equimolar amounts; however, in certain cases it may be beneficial to use an excess of one reagent to drive a reaction to completion. This is especially the case when the excess reagent can be readily removed by evaporation or extraction. Bases employed to neutralize HCl in reaction mixtures are generally used in slight to substantial excess (1.05-5 equivalents).

Compounds of Formula I can be prepared by reaction of a ketocarbamate of Formula II, wherein $R^D$ is alkyl or arylalkyl such as methyl, t-butyl or benzyl, with an organometallic reagent of Formula III wherein M includes, but is not limited to, MgCl, MgBr, MgI or Li:

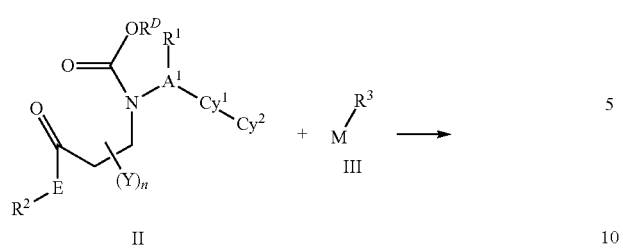

+ 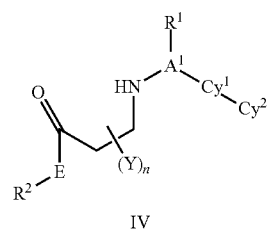

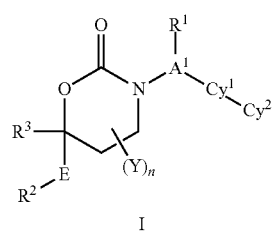

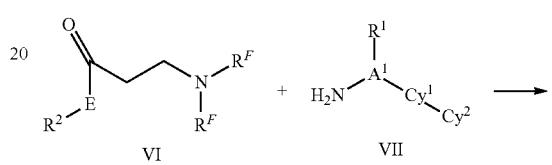

In specific examples, organometallic reagent III is allylmagnesium bromide, allylzinc bromide, (2-methylallyl)magnesium chloride or (2-methoxy-2-oxoethyl)zinc bromide. In certain cases when M is MgCl, MgBr or MgI, it is advantageous to add $CeCl_3$ to the reaction mixture.

Ketocarbamates of Formula II can be prepared by reaction of aminoketones of Formula IV with intermediates of Formula V wherein $R^E$ is a leaving group such as chlorine, succinyloxy, imidazolyl or t-butoxycarboxycarbonyl:

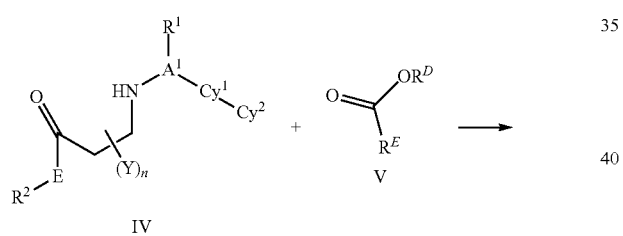

Aminoketones of Formula IV, wherein n is preferably but not necessarily 0, can be prepared by reaction of α,β-unsaturated ketones of Formula V with amines of Formula VII:

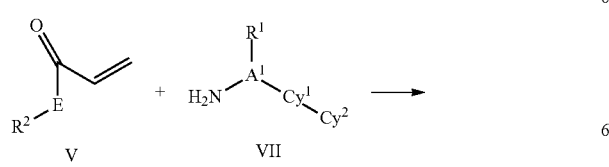

Alternatively, aminoketones of Formula IV, wherein n is preferably but not necessarily 0, can be prepared by reaction of β-dialkylaminoketones of Formula VI, wherein $R^F$ is lower alkyl especially methyl, with amines of Formula VII:

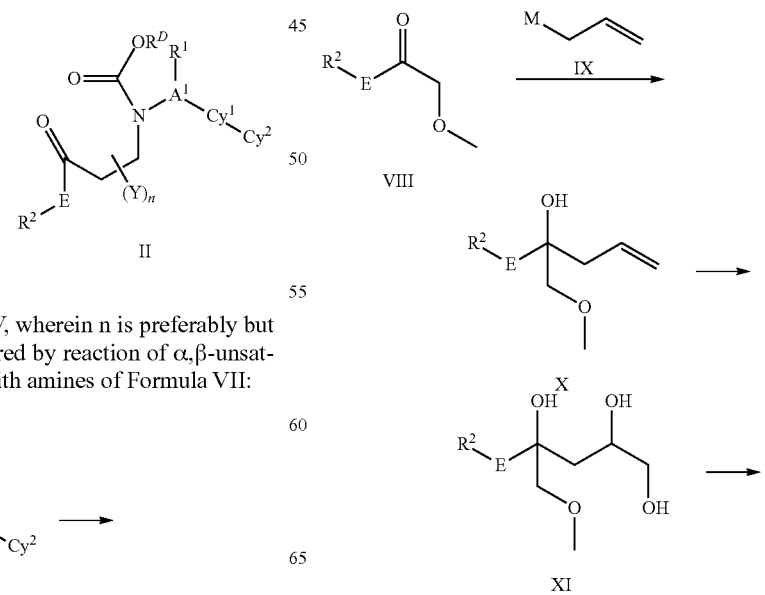

β-Dialkylaminoketones of Formula VI are in turn derived from α,β-unsaturated ketones of Formula V with dialkylamines of Formula $R^F NHR^F$.

Compounds of Formula $Ie^1$ can be prepared according to the following scheme:

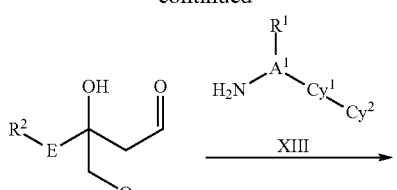

XII

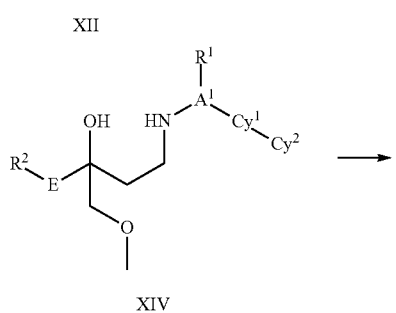

XIV

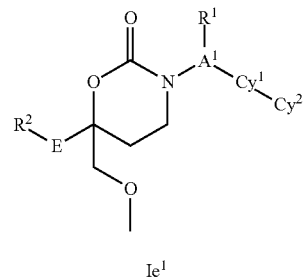

Ie¹

A methoxymethyl ketone of Formula VIII is reacted with an organometallic allyl reagent of Formula IX wherein M includes, but is not limited to, MgCl, MgBr, MgI or Li to yield an allyl compound of Formula X. In specific examples, organometallic reagent IX is allylmagnesium chloride, allylmagnesium bromide or allylzinc(II) bromide. The reaction is optionally carried out in the presence of anhydrous cerium trichloride Allyl compound of Formula X is converted to the aldehyde of Formula XII by ozonolysis or by OsO₄ catalysed dihydroxylation followed by cleavage of the glycol of Formula XI by periodates like sodium periodate Aminocarbinol of Formula XIV can be prepared by reductive amination with an amine of Formula XIII using sodium cyanoborohydride or sodium triacetoxyborohydride as reducing agent. Cyclisation of the aminocarbinol of Formula XIV to the compounds of Formula Ie¹ can be achieved by reacting with activated carbonic acid derivates such as phosgene, diphosgene, triphosgene or 1,1'-carbonyl-diimidazol.

Alternatively compounds of Formula (I) can be prepared from the reaction product of compounds represented by formulas II and III wherein Cy¹ is phenyl substituted with a leaving group such as bromine, for example, by using a "Suzuki" coupling reaction with Cy²-X[X is —B(OH)₂] as described in Example 111 of U.S. Provisional Patent Application No. 60/962,058, filed Jul. 26, 2007. The entire teachings of this application are incorporated herein by reference.

A compound of Formula I can also be prepared by reaction of a halo compound, wherein Hal is chlorine or bromine, with an isocyanate in the presence of a base:

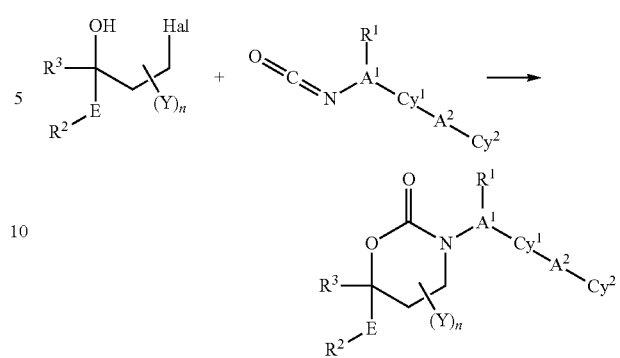

Halo compounds of this type can be prepared by reaction of β-haloketones with organometallic reagents $R^3$-M, wherein M is a metal containing residue including MgCl, MgBr, MgI or Li. The reaction is optionally carried out in the presence of anhydrous cerium trichloride:

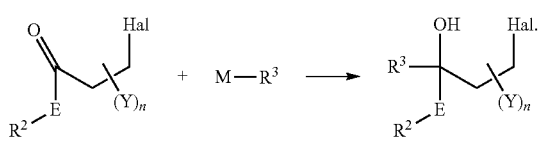

Specific conditions for these reactions are described in SYNTHESIS OF INHIBITORS OF 11BETA-HYDROXYSTEROID DEHYDROGENASE TYPE 1 (11β-HSD1), filed Jul. 25, 2008 as U.S. Provisional Application No. 61/137,013, the entire teachings of which are incorporated herein by reference.

| LC-MS METHODS | | | |
|---|---|---|---|
| LC-MS method 1: | | | |
| Column | Merck Cromolith Speed ROD, RP18e, 50 × 4.6 mm | | |
| Mobile Phase | A: water + 0.1% HCO₂H | | |
| | B: acetonitrile + 0.1% HCO₂H | | |
| | TIME (min) | A % | B % |
| | 0 | 90 | 10 |
| | 4.50 | 10 | 90 |
| | 5.00 | 10 | 90 |
| | 5.50 | 90 | 10 |
| Flow Rate | 1.5 mL/min | | |
| Wavelength | UV 220, 230, or 254 nm | | |
| LC-MS method 2: | | | |
| Column | Waters Xbridge C18, 30 × 4.6 mm, 2.5 μm | | |
| Mobile Phase | A: water + 0.1% NH₃ | | |
| | B: methanol | | |
| | TIME (min) | A % | B % |
| | 0 | 90 | 10 |
| | 0.15 | 90 | 10 |
| | 4.00 | 0 | 100 |
| | 4.40 | 0 | 100 |
| | 4.55 | 90 | 10 |
| | 5.00 | 90 | 10 |
| Flow Rate | 1.6 mL/min | | |
| Wavelength | UV 220, 230, or 254 nm | | |

Intermediate I

3-[(S)-1-(4-Chloro-phenyl)-ethylamino]-1-phenyl-propan-1-one

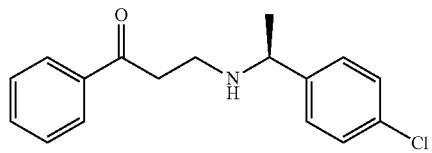 [SMILES: C[C@H](NCCC(=O)c1ccccc1)c1ccc(Cl)cc1]

NEt$_3$ (60 mL) followed by (S)-1-(4-chloro-phenyl)-ethylamine (20.5 g) was added to a solution of 3-chloro-1-phenyl-propan-1-one (23.2 g) in tetrahydrofuran (200 mL). The resulting mixture was stirred at room temperature overnight. Then, the solution was concentrated, water (100 mL) was added to the residue, and the resulting mixture was extracted with tert-butyl methyl ether. The combined organic extracts were washed with water and brine and dried (MgSO$_4$). The title compound was obtained after removal of the solvent.

Yield: 38.0 g (quantitative); Mass spectrum (EST$^+$): m/z=288/290 (Cl) [M+H]$^+$ The following compound was obtained in analogy to Intermediate I:

(1) 3-[(S)-1-(4-Bromo-phenyl)-ethylamino]-1-phenyl-propan-1-one

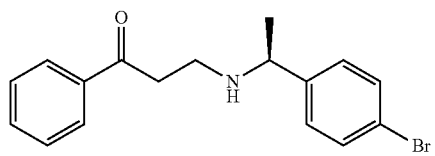 [SMILES: C[C@H](NCCC(=O)c1ccccc1)c1ccc(Br)cc1]

Mass spectrum (EST$^+$): m/z=332/334 (Br) [M+H]$^+$

Intermediate II

[(S)-1-(4-Chloro-phenyl)-ethyl]-(3-oxo-3-phenyl-propyl)-carbamic acid methyl ester

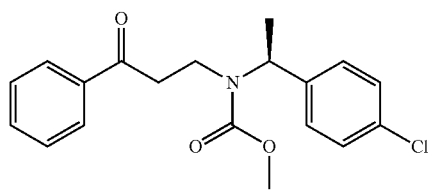 [SMILES: COC(=O)N(CCC(=O)c1ccccc1)[C@@H](C)c1ccc(Cl)cc1]

Methyl chloroformate (15.5 mL) dissolved in dichloromethane (100 mL) was added to a mixture of 3-[(S)-1-(4-chloro-phenyl)-ethylamino]-1-phenyl-propan-1-one (38.0 g) and Na$_2$CO$_3$ (23.5 g) in a mixture of dichloromethane (100 mL) and water (100 mL) at such a rate that the solution temperature remained between 20 and 26° C. After complete addition, the solution was stirred at ambient temperature for an additional 30 min. Then, the organic phase was separated and the aqueous phase was extracted once with dichloromethane. The combined organic phases were washed with brine and dried (MgSO$_4$). Then, silica gel (20 g) was added and the resulting mixture was stirred vigorously for 30 min. The silica gel was separated by filtration, washed with dichloromethane (200 mL), and the combined filtrate was concentrated under reduced pressure to give an oil. The oil was treated with iPr$_2$O (150 mL) to precipitate the title compound that was separated by filtration, washed with petroleum ether (30 mL), and dried. The filtrate was concentrated and the residue was taken up in petroleum ether (60 mL). The precipitate formed after a while of stirring was separated by filtration, washed with petroleum ether (20 mL), dried, and combined with the precipitate obtained before.

Yield: 38.2 g (82% of theory); Mass spectrum (ESI$^+$): m/z=346/348 (Cl) [M+H]$^+$.

The following compound was obtained in analogy to Intermediate II:

(1) [(S)-1-(4-Bromo-phenyl)-ethyl]-(3-oxo-3-phenyl-propyl)-carbamic acid methyl ester

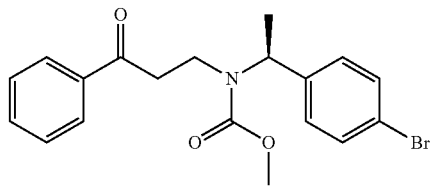 [SMILES: COC(=O)N(CCC(=O)c1ccccc1)[C@@H](C)c1ccc(Br)cc1]

Mass spectrum (ESI$^+$): m/z=390/392 (Br) [M+H]$^+$

Intermediate III

5-{[(S)-1-(4-Chloro-phenyl)-ethyl]-methoxycarbonyl-amino}-3-hydroxy-3-phenyl-pentanoic acid methyl ester (mixture of two diastereomers)

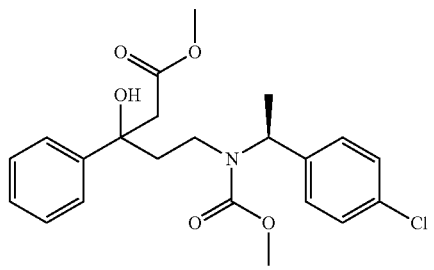 [SMILES: COC(=O)CC(O)(CCN(C(=O)OC)[C@@H](C)c1ccc(Cl)cc1)c1ccccc1]

Et$_2$Zn (1 M in hexane, 55 mL) was added dropwise to [(S)-1-(4-chloro-phenyl)-ethyl]-(3-oxo-3-phenyl-propyl)-carbamic acid methyl ester (3.80 g) dissolved in 1,2-dichloroethane (30 mL) and chilled to 0° C. under argon atmosphere. Then, (Ph$_3$P)$_3$RhCl (0.50 g) was added followed by the dropwise addition of methyl bromoacetate (1.0 mL) dissolved in 1,2-dichloroethane (10 mL). The resulting solution was stirred at 0-5° C. for 1 h and at ambient temperature for another 1.5 h. The solution was poured into ice-cold half-saturated aqueous NH$_4$Cl solution (150 mL). After addition of dichloromethane, the mixture was filtered through Celite which was extracted with an additional portion of dichloromethane. The organic phase was separated and washed with water and dried (MgSO$_4$). The solvent was removed and the residue was purified by chromatography on silica gel (cyclohexane/ethyl acetate 85:15→70:30) to give the title compound as a mixture of two diastereomers.

Yield: 4.6 g (quantitative); Mass spectrum (ESI$^+$): m/z=420/422 (Cl) [M+H]$^+$.

The following compound was obtained in analogy to Intermediate III:

(1) 5-{[(S)-1-(4-Bromo-phenyl)-ethyl]-methoxycarbonyl-amino}-3-hydroxy-3-phenyl-pentanoic acid methyl ester (mixture of two diastereomers)

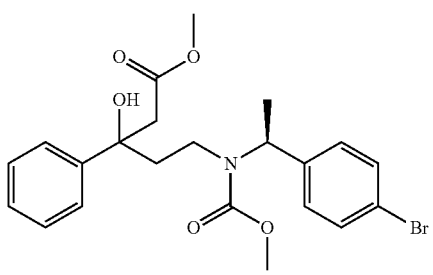 [SMILES: COC(=O)CC(O)(CCN(C(=O)OC)[C@@H](C)c1ccc(Br)cc1)c1ccccc1]

Mass spectrum (ESI+): m/z=464/466 (Br) [M+H]+

Intermediate IV

[(S)-1-(4-Chloro-phenyl)-ethyl]-(3,5-dihydroxy-5-methyl-3-phenyl-hexyl)-carbamic acid methyl ester (mixture of two diastereomers)

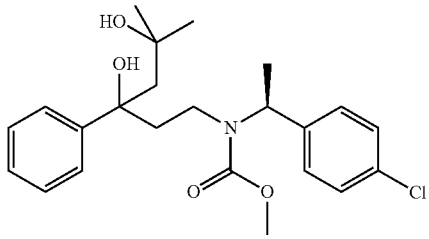 [SMILES: COC(=O)N(CCC(O)(CC(C)(C)O)c1ccccc1)[C@@H](C)c1ccc(Cl)cc1]

MeLi (1.6 M in Et$_2$O, 5.1 mL) diluted with tetrahydrofuran (3 mL) was added to a solution of 5-{[(S)-1-(4-chloro-phenyl)-ethyl]-methoxycarbonyl-amino}-3-hydroxy-3-phenyl-pentanoic acid methyl ester (product from Intermediate III, 1.10 g) in tetrahydrofuran (8 mL) chilled to −75° C. under argon atmosphere. The solution was stirred at ca. −70° C. for 2.5 h and then poured into half-saturated aqueous NH$_4$Cl solution (150 mL). The resulting mixture was extracted with ethyl acetate and the combined extracts were washed with brine and dried (MgSO$_4$). The solvent was removed and the residue was purified by chromatography on silica gel (cyclohexane/ethyl acetate 85:15→70:30) to give the title compound as a mixture of two diastereomers.

Yield: 0.62 g (56% of theory); Mass spectrum (ESI+): m/z=420/422 (Cl) [M+H]+. The reaction may also be conducted using MeMgCl instead of MeLi as described above.

The following compound was obtained in analogy to Intermediate IV:

(1) [(S)-1-(4-Bromo-phenyl)-ethyl]-(3,5-dihydroxy-5-methyl-3-phenyl-hexyl)-carbamic acid methyl ester (mixture of two diastereomers)

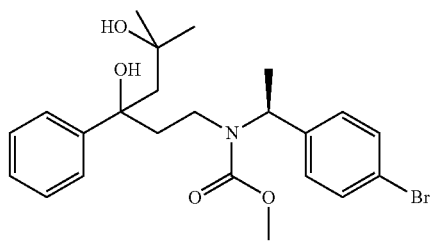 [SMILES: COC(=O)N(CCC(O)(CC(C)(C)O)c1ccccc1)[C@@H](C)c1ccc(Br)cc1]

Mass spectrum (ESI+): m/z=464/466 (Br) [M+H]+.

Intermediate V

3-[(S)-1-(4-Chloro-phenyl)-ethyl]-(S)-6-(2-hydroxy-2-methyl-propyl)-6-phenyl-[1,3]oxazinan-2-one and
3-[(S)-1-(4-chloro-phenyl)-ethyl]-(R)-6-(2-hydroxy-2-methyl-propyl)-6-phenyl-[1,3]oxazinan-2-one

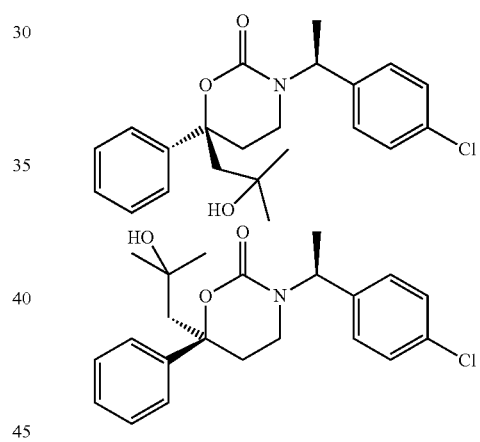

NaH (60% in mineral oil, 0.15 g) was added to a solution of [(S)-1-(4-chloro-phenyl)-ethyl]-(3,5-dihydroxy-5-methyl-3-phenyl-hexyl)-carbamic acid methyl ester (Intermediate IV, 0.60 g) in tetrahydrofuran (10 mL) under argon atmosphere. The resulting mixture was stirred at reflux temperature for 2.5 h. Then, aqueous NH$_4$Cl solution was added and the resulting mixture was extracted with ethyl acetate. The combined organic extracts were washed with brine, dried (MgSO$_4$), and concentrated. The residue was purified by chromatography on silica gel (cyclohexane/ethyl acetate 60:40→0:100) to separate the two title compounds.

3-[(S)-1-(4-Chloro-phenyl)-ethyl]-(S)-6-(2-hydroxy-2-methyl-propyl)-6-phenyl-[1,3]oxazinan-2-one: Yield: 40 mg (7% of theory). Mass spectrum (ESI+): m/z=388/390 (Cl) [M+H]+. $^1$H NMR (400 MHz, DMSO-d$_6$) δ 0.80 (s, 3H), 1.18 (s, 3H), 1.41 (d, J=7.0 Hz, 3H), 2.01 (s, 2H), 2.08 (td, J=11.5, 5.4 Hz, 1H), 2.37-2.51 (m, 2H), 2.95-3.02 (m, 1H), 4.23 (s, 1H), 5.38 (q, J=7.0 Hz, 1H), 6.86 (d, J=8.4 Hz, 2H), 7.14 (d, J=8.4 Hz, 2H), 7.27-7.39 (m, 5H).

3-[(S)-1-(4-Chloro-phenyl)-ethyl]-(R)-6-(2-hydroxy-2-methyl-propyl)-6-phenyl-[1,3]oxazinan-2-one: Yield: 93 mg (17% of theory). Mass spectrum (ESI+): m/z=388/390 (Cl) [M+H]+. 1H NMR (400 MHz, DMSO-$d_6$) δ 0.81 (s, 3H), 1.16 (s, 3H), 1.18 (d, J=7.3 Hz, 3H), 2.03 (s, 2H), 2.31-2.41 (m, 2H), 2.51-2.59 (m, 1H), 2.64-2.71 (m, 1H), 4.20 (s, 1H), 5.31 (q, J=7.1 Hz, 1H), 7.25 (d, J=8.4 Hz, 2H), 7.28-7.35 (m, 3H), 7.37-7.43 (m, 4H).

The following compound was obtained in analogy to Intermediate V:

(1) 3-[(S)-1-(4-Bromo-phenyl)-ethyl]-(S)-6-(2-hydroxy-2-methyl-propyl)-6-phenyl-[1,3]oxazinan-2-one

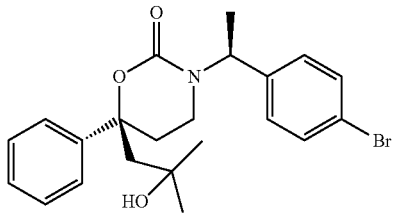

The compound was obtained from [(S)-1-(4-bromo-phenyl)-ethyl]-(3,5-dihydroxy-5-methyl-3-phenyl-hexyl)-carbamic acid methyl ester (mixture of two diastereomers) in a mixture with 3-[(S)-1-(4-bromo-phenyl)-ethyl]-(R)-6-(2-hydroxy-2-methyl-propyl)-6-phenyl-[1,3]oxazinan-2-one that was resolved into the pure diastereomers by chromatography as described above.

Intermediate VI (S)-6-(2-Hydroxy-2-methyl-propyl)-6-phenyl-3-{ (S)-1-[4-(4,4,5,5-tetramethyl-[1,3,2]dioxaborolan-2-yl)-phenyl]-ethyl}-[1,3]oxazinan-2-one

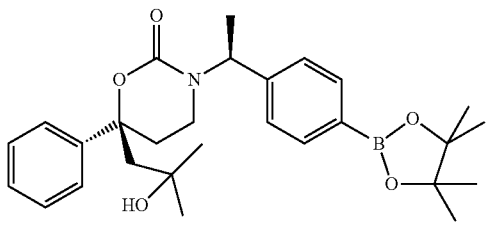

A flask charged with a stir bar, 3-[(S)-1-(4-bromo-phenyl)-ethyl]-(S)-6-(2-hydroxy-2-methyl-propyl)-6-phenyl-[1,3]oxazinan-2-one (4.00 g), bis(pinacolato)diboron (3.05 g), 1,1'-bis(diphenylphosphino)ferrocene (0.25 g), $KO_2CCH_3$ (3.18 g), and dimethyl sulfoxide (30 mL) was sparged with argon for 15 min. Then, [1,1'-bis(diphenylphosphino)ferrocene]-dichloro-palladium(II)dichloromethane complex (0.38 g) was added and the resulting mixture was heated to 90° C. and stirred at this temperature overnight. After cooling to ambient temperature, ethyl acetate (150 mL) was added and the mixture was washed with water (3×50 mL) and brine (50 mL) and dried ($MgSO_4$). The solvent was removed under reduced pressure and the residue was purified by chromatography on silica gel (cyclohexane/ethyl acetate 33:66→0:100) to give the title compound as a colorless solid.

Yield: 3.50 mg (79% of theory); Mass spectrum (ESI+): m/z=480 [M+H]+

The following compound was obtained in analogy to Intermediate VI:

(1) (R)-6-Methoxymethyl-6-phenyl-3-{(S)-1-[4-(4,4,5,5-tetramethyl-[1,3,2]dioxaborolan-2-yl)-phenyl]-ethyl}-[1,3]oxazinan-2-one

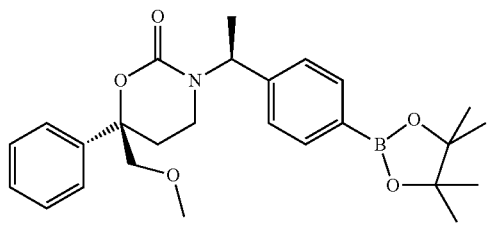

3-[(S)-1-(4-Bromo-phenyl)-ethyl]-(R)-6-methoxymethyl-6-phenyl-[1,3]oxazinan-2-one was used as starting compound.

Intermediate VII

6-Chloro-4-methyl-2H-pyridazin-3-one and 6-chloro-5-methyl-2H-pyridazin-3-one

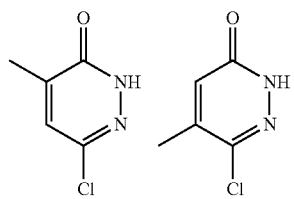

A suspension of 3,6-dichloro-4-methylpyridazine (6.60 g) in 3.3 M aqueous NaOH solution (66 mL) was stirred at reflux temperature for 2 h. The heating bath was removed and 50% aqueous acetic acid (25 mL) was added. The aqueous solution was adjusted to pH value 6 and the precipitate formed thereafter was separated by filtration and washed with little water. The precipitate was chromatographed on silica gel (cyclohexane/ethyl acetate 90:10→0:100) to separate the two title compounds.

6-Chloro-4-methyl-2H-pyridazin-3-one: Yield: 2.70 g (46% of theory). Mass spectrum (ESI+): m/z=145/147 (Cl) [M+H]+. 1H NMR (400 MHz, DMSO-$d_6$) δ 2.06 (d, J=1.3 Hz, 3H), 7.44 (incompletely resolved q, J=1.3 Hz, 1H), 13.03 (broad s, 1H).

6-Chloro-5-methyl-2H-pyridazin-3-one: Yield: 1.90 g (32% of theory). Mass spectrum (ESI+): m/z=145/147 (Cl) [M+H]+. 1H NMR (400 MHz, DMSO-$d_6$) δ 2.19 (d, J=1.3 Hz, 3H), 6.91 (incompletely resolved q, J=1.3 Hz, 1H), 13.02 (broad s, 1H).

The following compound was obtained in analogy to Intermediate VII:

(1) 6-Chloro-2H-pyridazin-3-one

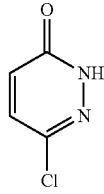

Mass spectrum (ESI+): m/z=131/133 (Cl) [M+H]+

Intermediate VIII

6-Chloro-2,4-dimethyl-2H-pyridazin-3-one

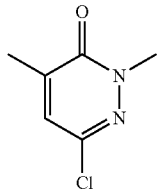

Methyl iodide (1.3 mL) was added to a mixture of 6-chloro-4-methyl-2H-pyridazin-3-one (2.70 g) and $K_2CO_3$ (3.40 g) in N,N-dimethylformamide (27 mL). The resulting mixture was stirred at ambient temperature overnight. Then, water was added and the mixture was extracted with ethyl acetate. The combined organic extracts were washed with water and brine and dried ($MgSO_4$). After removal of the solvent, the title compound was obtained as a solid.

Yield: 2.97 g (100% of theory); Mass spectrum (ESI$^+$): m/z=159/161 (Cl) [M+H]$^+$.

The following compound was obtained in analogy to Intermediate VIII:

(1) 6-Chloro-2,5-dimethyl-2H-pyridazin-3-one

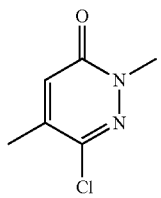

Mass spectrum (ESI$^+$): m/z=159/161 (Cl) [M+H]$^+$.

Intermediate IX (5-Bromo-2-nitro-phenyl)-methyl-amine

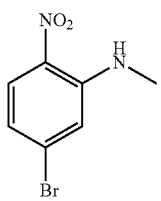

Methylamine (2 M in tetrahydrofuran, 11.4 mL) was added to a mixture of 4-bromo-2-fluoro-1-nitro-benzene (2.50 g) and $K_2CO_3$ (1.90 g) in N,N-dimethylformamide (40 mL). The resulting mixture was stirred at ambient temperature overnight. Then, the mixture was concentrated under reduced pressure and dichloromethane was added. The resulting mixture was washed with 0.5 M aqueous HCl solution and brine and dried ($MgSO_4$). The solvent was removed to give the product as a solid.

Yield: 2.60 g (99% of theory); Mass spectrum (ESI$^+$): m/z=231/233 (Br) [M+H]$^+$.

The following compound was obtained in analogy to Intermediate IX:

(1) (4-Bromo-2-nitro-phenyl)-methyl-amine

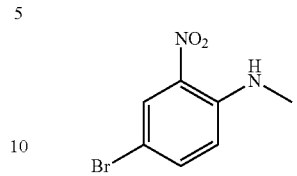

Mass spectrum (ESI$^+$): m/z=231/233 (Br) [M+H]$^+$.

Intermediate X

4-Bromo-2-methylamino-aniline

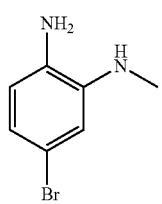

A mixture of (5-bromo-2-nitro-phenyl)-methyl-amine (2.60 g) and Raney nickel (0.25 g) in tetrahydrofuran (100 mL) was shaken under hydrogen atmosphere (50 psi) at room temperature overnight. Then, the catalyst was separated by filtration and the filtrate was concentrated under reduced pressure to give the crude title compound as a brown oil that was used without further purification.

Yield: 2.20 g (97% of theory); Mass spectrum (ESI$^+$): m/z=201/203 (Br) [M+H]$^+$.

The following compound was obtained in analogy to Intermediate X:

(1) 5-Bromo-2-methylamino-aniline

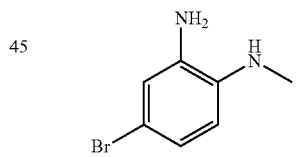

Mass spectrum (ESI$^+$): m/z=201/203 (Br) [M+H]$^+$.

Intermediate XI

6-Bromo-1,2-dimethyl-1H-benzoimidazole

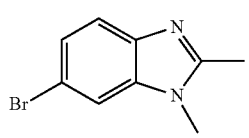

A solution of 4-bromo-2-methylamino-aniline (1.10 g) in acetic acid (15 mL) was stirred at 130° C. for 2 h. After cooling to ambient temperature, the solution was concentrated under reduced pressure and the residue was taken up in ethyl acetate. The resulting solution was washed with 10% aqueous K$_2$CO$_3$ solution and brine and dried (MgSO$_4$). The solvent was removed and the remainder was purified by chromatography on silica gel (CH$_2$Cl$_2$/MeOH/NH$_4$OH 99:1:0.1→9:1:0.1) to give the title compound as a solid.

Yield: 0.58 g (47% of theory); Mass spectrum (ESI$^+$): m/z=225/227 (Br) [M+H]$^+$.

The following compound was obtained in analogy to Intermediate XI:

(1) 5-Bromo-1,2-dimethyl-1H-benzoimidazole

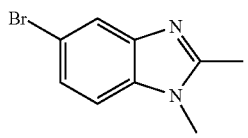

Mass spectrum (ESI$^+$): m/z=225/227 (Br) [M+H]$^+$

Intermediate XII

6-Chloro-2-cyclopropylmethyl-2H-pyridazin-3-one

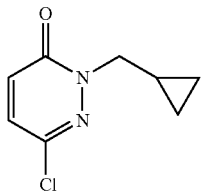 [SMILES: O=c1ccc(Cl)nn1CC1CC1]

Cyclopropylmethyl bromide (0.82 mL) was added to a mixture of 6-chloro-2H-pyridazin-3-one (1.0 g) and K$_2$CO$_3$ (2.10 g) in N,N-dimethylformamide (10 mL). The resulting mixture was stirred at 60° C. overnight. Then, water was added and the mixture was extracted with ethyl acetate. The combined organic extracts were washed with water and brine and dried (MgSO$_4$). After removal of the solvent, the residue was purified by chromatography on silica gel (CH$_2$Cl$_2$/MeOH/NH$_4$OH 99:1:0.1) to afford the title compound as an oil.

Yield: 0.85 g (60% of theory); Mass spectrum (ESI$^+$): m/z=185/187 (Cl) [M+H]$^+$.

Intermediate XIII

6-Chloro-2-cyclopropyl-2H-pyridazin-3-one

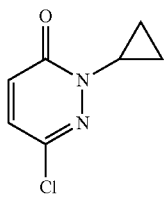

A microwave-suited vessel charged with a stir bar, 6-chloro-2H-pyridazin-3-one (0.15 g), cyclopropylboronic acid (0.30 g), pyridine (0.75 mL), triethylamine (0.8 mL), and tetrahydrofuran (5 mL) was sparged with argon for 5 min. Then, Cu(O$_2$CCH$_3$)$_2$ (0.42 g) was added and the mixture was stirred in a microwave oven under microwave irradiation at 140° C. for 10 min. After cooling to room temperature, the solvent was evaporated and water was added. The resultant mixture was extracted with ethyl acetate and the combined organic extracts were washed with water and aqueous NaHCO$_3$ solution. After drying (MgSO$_4$) and removing the solvent, the residue was purified by chromatography on silica gel (CH$_2$Cl$_2$/MeOH/NH$_4$OH 99:1:0.1→9:1:0.1) to afford the title compound.

Yield: 35 mg (18% of theory); Mass spectrum (ESI$^+$): m/z=171/173 (Cl) [M+H]$^+$.

The following compound was obtained in analogy to Intermediate XIII:

(1) 1-Cyclopropyl-4-(4-methoxy-benzyloxy)-1H-pyridin-2-one

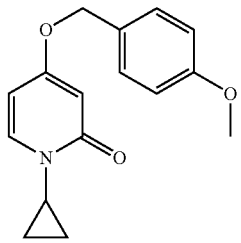 [SMILES: COc1ccc(COc2ccn(C3CC3)c(=O)c2)cc1]

Mass spectrum (ESI$^+$): m/z=272 [M+H]$^+$.

Intermediate XIV 4-(4-{(S)-1-[(S)-6-(2-Hydroxy-2-methyl-propyl)-2-oxo-6-phenyl-[1,3]oxazinan-3-yl]-ethyl}-phenyl)-3,6-dihydro-2H-pyridine-1-carboxylic acid tert-butyl ester

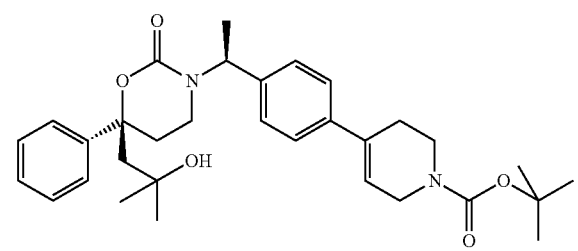

N,N-Dimethylformamide (5 mL) was added to a flask charged with a stir bar, 3-[(S)-1-(4-bromo-phenyl)-ethyl]-(S)-6-(2-hydroxy-2-methyl-propyl)-6-phenyl-[1,3]oxazinan-2-one (0.30 g), 4-(4,4,5,5-tetramethyl-[1,3,2]dioxaborolan-2-yl)-3,6-dihydro-2H-pyridine-1-carboxylic acid tert-butyl ester (0.22 g), K$_2$CO$_3$ (0.29 g), and [1,1'-bis(diphenylphosphino)-ferrocene]-dichloropalladium(II) (57 mg) under argon atmosphere. The resulting mixture was stirred at 80° C. overnight. After cooling to ambient temperature, water was added and the resulting mixture was extracted with ethyl acetate. The combined organic extracts were washed with brine, dried (MgSO$_4$), and concentrated. The residue was purified by chromatography on silica gel (cyclohexane/ethyl acetate 40:60→0:100) to afford the title compound.

Yield: 0.35 g (93% of theory); Mass spectrum (ESI$^+$): m/z=535 [M+H]$^+$.

Intermediate XV 4-(4-{(S)-1-[(S)-6-(2-Hydroxy-2-methyl-propyl)-2-oxo-6-phenyl-[1,3]oxazinan-3-yl]-ethyl}-phenyl)-piperidine-1-carboxylic acid tert-butyl ester

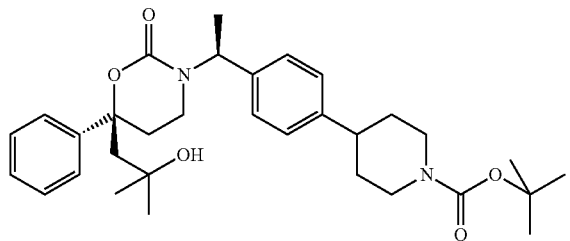

A mixture of 4-(4-{(S)-1-[(S)-6-(2-hydroxy-2-methyl-propyl)-2-oxo-6-phenyl-[1,3]oxazinan-3-yl]-ethyl}-phenyl)-3,6-dihydro-2H-pyridine-1-carboxylic acid tert-butyl ester (0.34 g) and 10% palladium on carbon (60 mg) in methanol (10 mL) was shaken in hydrogen atmosphere (50 psi) for 4 h. Then, the catalyst was separated by filtration and the filtrate was concentrated to yield the title compound.

Yield: 0.30 g (88% of theory); LC (method 1): $t_R$=4.31 min; Mass spectrum (ESI$^+$): m/z=537 [M+H]$^+$.

Intermediate XVI 5-(4-{(S)-1-[(S)-6-(2-Hydroxy-2-methyl-propyl)-2-oxo-6-phenyl-[1,3]oxazinan-3-yl]-ethyl}-phenyl)-pyridine-2-carboxylic acid

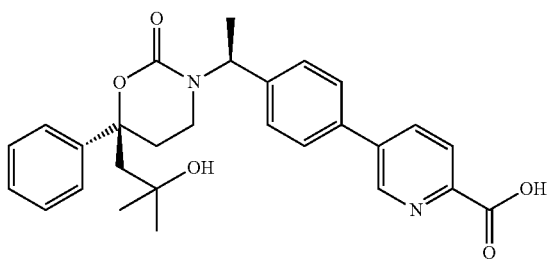

2 M aqueous Na$_2$CO$_3$ solution (1.3 mL) was added to a solution of (S)-6-(2-hydroxy-2-methylpropyl)-6-phenyl-3-{(S)-1-[4-(4,4,5,5-tetramethyl-1,3,2-dioxaborolan-2-yl)phenyl]-ethyl}-1,3-oxazinan-2-one (0.60 g) and 5-bromo-pyridine-2-carboxylic acid methyl ester (0.41 g) in N,N-dimethylformamide (4 mL). The resulting mixture was sparged with argon for 10 min, before [1,1'-bis(diphenylphosphino)ferrocene]-dichloropalladium(II)dichloromethane complex (61 mg) was added. The mixture was heated to 100° C. and stirred at this temperature overnight. After cooling to ambient temperature, the mixture was diluted with ethyl acetate and extracted with water and brine. The aqueous extracts were combined, acidified (pH ca. 5-6) using citric acid, and extracted with CH$_2$Cl$_2$/MeOH (ca. 10:1). The combined organic extracts were washed with brine and dried (MgSO$_4$). The solvent was removed and the residue was purified by chromatography on silica gel (CH$_2$Cl$_2$/MeOH 98:2→50:50) to afford the title compound as a resin-like solid.

Yield: 0.44 g (73% of theory); Mass spectrum (ESI$^+$): m/z=475 [M+H]$^+$.

Intermediate XVII

3-[(S)-1-(4'-Amino-3'-nitro-biphenyl-4-yl)-ethyl]-(S)-6-(2-hydroxy-2-methyl-propyl)-6-phenyl-[1,3]oxazinan-2-one

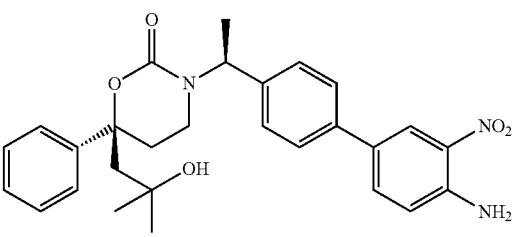

A flask charged with a stir bar, 3-[(S)-1-(4-bromo-phenyl)-ethyl]-(S)-6-(2-hydroxy-2-methyl-propyl)-6-phenyl-[1,3]oxazinan-2-one (1.00 g), 2-nitro-4-(4,4,5,5-tetramethyl-[1,3,2]dioxaborolan-2-yl)-phenylamine (0.92 g), and 2 M aqueous Na$_2$CO$_3$ solution (2.3 mL) was sparged with argon for 15 min. Then, [1,1'-bis(diphenylphosphino)ferrocene]-dichloro-palladium(II)dichloromethane complex (57 mg) was added and the mixture was stirred at 100° C. overnight. After cooling to ambient temperature, water was added and the resulting mixture was extracted with ethyl acetate. The combined organic extracts were washed with brine, dried (MgSO$_4$), and concentrated. The residue was purified by chromatography on silica gel (CH$_2$Cl$_2$/MeOH 98:2→80:20) to afford the title compound as an oil that was crystallized using a mixture of ethyl acetate and iPr$_2$O (ca. 10:1).

Yield: 0.53 g (93% of theory); Mass spectrum (ESI$^+$): m/z=490 [M+H]$^+$.

Intermediate XVIII

3-[(S)-1-(3',4'-Diamino-biphenyl-4-yl)-ethyl]-(S)-6-(2-hydroxy-2-methyl-propyl)-6-phenyl-[1,3]oxazinan-2-one

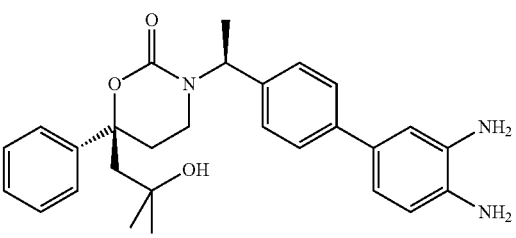

A mixture of 3-[(S)-1-(4'-amino-3'-nitro-biphenyl-4-yl)-ethyl]-(S)-6-(2-hydroxy-2-methyl-propyl)-6-phenyl-[1,3]oxazinan-2-one (0.50 g) and 10% palladium on carbon (0.10 g) in a mixture of methanol (10 mL) and tetrahydrofuran (10 mL) was shaken in hydrogen atmosphere (3 bar) at room temperature for 3.5 h. Then, the catalyst was separated by filtration and the filtrate was concentrated under reduced pressure to afford the title compound as an oil.

Yield: 0.46 g (97% of theory); Mass spectrum (ESI⁺): m/z=460 [M+H]⁺.

Intermediate XIX

1-Cyclopropyl-4-hydroxy-1H-pyridin-2-one

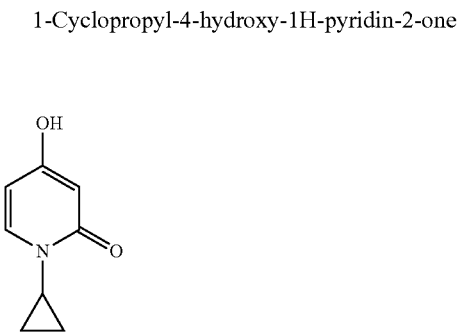

Trifluoroacetic acid (1 mL) was added to a flask charged with a stir bar and 1-cyclopropyl-4-(4-methoxy-benzyloxy)-1H-pyridin-2-one (0.17 g) and chilled in an ice/EtOH bath. The resulting mixture was stirred with cooling for 1.5 h and at ambient temperature for another 4.5 h. Then, the solution was concentrated under reduced pressure and the residue was triturated with tert-butyl methyl ether and dried to give the title compound as a solid.

Yield: 0.10 g (quantitative); Mass spectrum (ESI⁺): m/z=152 [M+H]⁺.

Intermediate XX

Trifluoro-methanesulfonic acid 1-cyclopropyl-2-oxo-1,2-dihydro-pyridin-4-yl ester

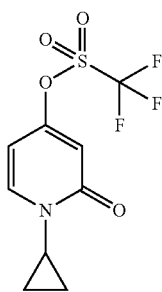

Trifluoromethanesulfonic anhydride (0.12 mL) was added to a flask charged with a stir bar, 1-cyclopropyl-4-hydroxy-1H-pyridin-2-one (0.10 g), NEt₃ (0.24 mL), and dichloromethane (8 mL) and chilled in an ice/EtOH bath. The resulting mixture was stirred with cooling for 2 h and at ambient temperature for another 2 h. Then, the solution was diluted with dichloro-methane and washed in succession with water, aqueous NaHCO₃ solution, and water. The organic solution was dried (MgSO₄), the solvent was removed, and the residue was purified by chromatography on silica gel (dichloromethane/methanol 99:1→90:10) to afford the title compound as a resin-like solid.

Yield: 0.07 g (36% of theory); Mass spectrum (ESI⁺): m/z=284 [M+H]⁺.

The following compound was obtained in analogy to Intermediate XX:

(1) Trifluoro-methanesulfonic acid 1-methyl-2-oxo-1,2-dihydro-pyridin-4-yl ester

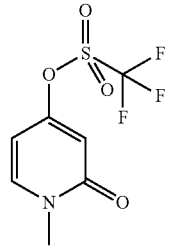 [SMILES: Cn1ccc(OS(=O)(=O)C(F)(F)F)cc1=O]

Mass spectrum (ESI⁺): m/z=258 [M+H]⁺

Intermediate XXI

5-Bromo-1-cyclopropylmethyl-1H-pyridin-2-one

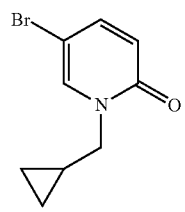

KOᵗBu (0.68 g) was added to a solution of 5-bromo-1H-pyridin-2-one (1.00 g) in tetrahydrofuran (20 mL) at room temperature. After stirring for 30 min, cyclopropylmethyl bromide (0.77 mL) and N,N-dimethylformamide (3 mL) were added to the suspension and the resulting mixture was warmed to 70° C. After stirring the mixture at 70° C. for 2 h, the reaction was finished. The mixture was cooled to room temperature, diluted with ethyl acetate (50 mL), and washed with water (2×20 mL) and brine (20 mL). Then, the solution was dried (MgSO₄) and the solvent was removed to give the title compound as a colorless oil.

Yield: 1.18 g (90% of theory); Mass spectrum (ESI⁺): m/z=228/230 (Br) [M+H]⁺.

Intermediate XXII

1-Methoxy-2-phenyl-pent-4-en-2-ol

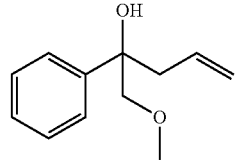

2-Methoxy-1-phenyl-ethanone (5.00 g) dissolved in tetrahydrofuran (50 mL) was added to 2 M allylmagnesium chloride in tetrahydrofuran (21 mL) at room temperature. The solution was stirred at room temperature for 3 h and then 10% aqueous NH₄Cl solution (50 mL) was added. The resulting mixture was extracted with tert-butyl methyl ether (3×50 mL) and the combined extracts were washed with water (50 mL) and brine (50 mL). The solvent was evaporated to afford the title compound as a colorless oil.

Yield: 6.40 g (quantitative); Mass spectrum (ESI⁺): m/z=175 [M+H−H₂O]⁺.

Intermediate XXIII

5-Methoxy-4-phenyl-pentane-1,2,4-triol

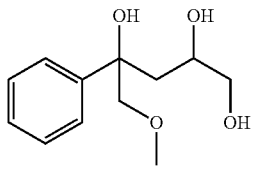 [SMILES: COCC(O)(CC(O)CO)c1ccccc1]

OsO$_4$ (4% in water, 2 mL; alternatively, K$_2$OsO$_4$ may be used) followed by N-methyl-morpholine-N-oxide (5.20 g) was added to a solution of 1-methoxy-2-phenyl-pent-4-en-2-ol (1.10 g) in tetrahydrofuran (10 mL) chilled in an ice bath. The cooling bath was removed and the solution was stirred at room temperature overnight. Then, 10% aqueous Na$_2$S$_2$O$_5$ solution (10 mL) was added and the resulting mixture was stirred at room temperature for another 1.5 h. After removal of the organic solvent under reduced pressure, the remaining mixture was extracted with ethyl acetate. The combined extracts were washed with brine and dried (MgSO$_4$). The solvent was evaporated to afford the title compound in good purity (ca. 95%).

Yield: 1.20 g (96% of theory); Mass spectrum (ESI$^-$): m/z=225 [M−H]$^-$.

Intermediate XXIV

3-Hydroxy-4-methoxy-3-phenyl-butyraldehyde

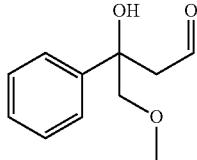

NaIO$_4$ (5.20 g) was added to a mixture of 5-methoxy-4-phenyl-pentane-1,2,4-triol (1.10 g), dichloromethane (10 mL), and water (5 mL) chilled in an ice bath. The mixture was stirred vigorously while warming to ambient temperature in the cooling bath and further stirred at this temperature overnight. Then, water (20 mL) and dichloromethane (50 mL) were added, the organic layer was separated, and the aqueous layer was extracted with dichloromethane (2×25 mL). The combined organic phases were washed with water and dried (MgSO$_4$). After removal of the solvent, the title compound was obtained which was used without further purification.

Yield: 0.94 g (quantitative).

Intermediate XXV

4-[(S)-1-(4-Bromo-phenyl)-ethylamino]-1-methoxy-2-phenyl-butan-2-ol

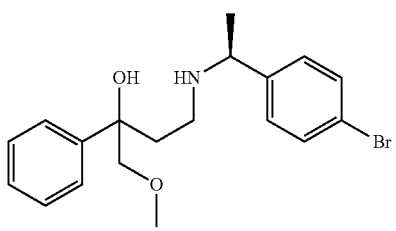 [SMILES: COCC(O)(CCN[C@@H](C)c1ccc(Br)cc1)c1ccccc1]

(S)-1-(4-Bromo-phenyl)-ethylamine (0.93 g), NaHB(O$_2$CH$_3$)$_3$ (0.98 g), and acetic acid (0.27 mL) were added in the given order to a solution of 3-hydroxy-4-methoxy-3-phenyl-butyraldehyde (0.90 g) in tetrahydrofuran (20 mL) at ca. 10-15° C. The cooling bath was removed and the mixture was stirred at room temperature for 2 h. Then, water (50 mL) and 1 M aqueous NaOH solution (20 mL) were added and the resulting mixture was stirred for another 30 min. The mixture was extracted with ethyl acetate and the combined extracts were washed with water and brine. After drying (MgSO$_4$), the solvent was removed to give the title compound which was used without further purification.

Yield: 1.80 g (quantitative); Mass spectrum (ESI$^+$): m/z=378/380 (Br) [M+H]$^+$.

Intermediate XXVI

4-{(S)-1-[(S)-6-(2-Hydroxy-2-methyl-propyl)-2-oxo-6-phenyl-[1,3]oxazinan-3-yl]-ethyl}-benzoic acid methyl ester

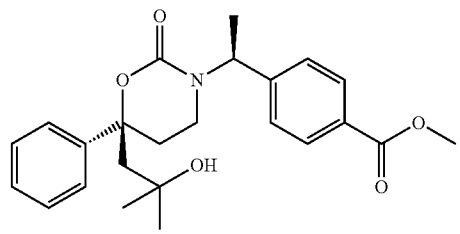

NEt$_3$ (0.47 mL) and [1,1'-bis(diphenylphosphino)ferrocene]-dichloropalladium(II)dichloromethane complex (0.15 g) were added to a solution of 3-[(S)-1-(4-bromo-phenyl)-ethyl]-(S)-6-(2-hydroxy-2-methyl-propyl)-6-phenyl-[1,3]oxazinan-2-one (1.04 g) in MeCN (2.5 mL), methanol (20 mL), and N,N-dimethylformamide (5 mL). The resulting mixture was sparged with argon for 5 min and then transferred to a pressure-resistant vessel that was filled with CO (5.5. bar). The mixture was heated to 70° C. and stirred at this temperature for 18 h before another portion of [1,1'-bis(diphenylphosphino)ferrocene]-dichloropalladium(II) dichloromethane complex (0.15 g) was added. After stirring at 70° C. for another 4 h, the mixture was cooled to ambient temperature, filtered, and concentrated under reduced pressure. The residue was taken up in ethyl acetate and the resulting mixture was washed with water and brine and dried (MgSO$_4$). The solvent was removed and the residue was purified by chromatography on silica gel (cyclohexane/ethyl acetate 40:60→0:100) to afford the title compound as an oil.

Yield: 0.73 g (55% of theory); Mass spectrum (ESI$^-$): m/z=456 [M+HCOO]$^-$

Intermediate XXVII

4-{(S)-1-[(S)-6-(2-Hydroxy-2-methyl-propyl)-2-oxo-6-phenyl-[1,3]oxazinan-3-yl]-ethyl}-benzoic acid

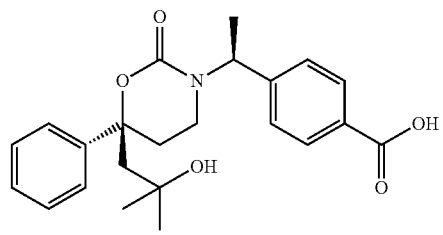

1 M aqueous NaOH solution (5 mL) was added to a solution of 4-{(S)-1-[(S)-6-(2-hydroxy-2-methyl-propyl)-2-oxo-6-phenyl-[1,3]oxazinan-3-yl]-ethyl}-benzoic acid methyl ester (0.73 g) in tetrahydrofuran (5 mL). The resulting solution was stirred at room temperature overnight. Then, the solution was concentrated and the residue was taken up in water and filtered. The aqueous filtrate was acidified with 1 M hydrochloric acid and the resulting mixture was extracted with ethyl acetate. The combined extracts were washed with brine and dried (MgSO$_4$). The solvent was removed to afford the title compound as a foam-like solid.

Yield: 0.38 g (72% of theory); LC (method 1): $t_R$=2.60 min; Mass spectrum (ESI$^+$): m/z=398 [M+H]$^+$ Intermediate XXVIII 4-{(S)-1-[(S)-6-(2-Hydroxy-2-methyl-propyl)-2-oxo-6-phenyl-[1,3]oxazinan-3-yl]-ethyl}-benzoic acid hydrazide

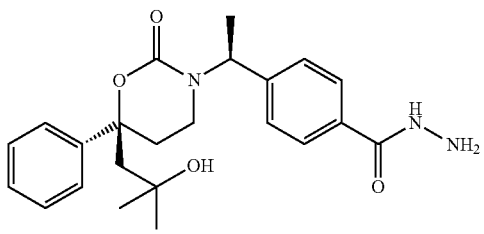

2-(1H-benzotriazol-1-yl)-1,1,3,3-tetramethyluronium tetrafluoroborate (0.33 g) was added to 4-{(S)-1-[(S)-6-(2-hydroxy-2-methyl-propyl)-2-oxo-6-phenyl-[1,3]oxazinan-3-yl]-ethyl}-benzoic acid (0.37 g) and EtNiPr$_2$ (0.41 mL) dissolved in N,N-dimethylformamide (5 mL). After stirring the solution at room temperature for 10 min, hydrazine hydrate (0.23 mL) was added. The solution was stirred at room temperature overnight and then diluted with water. The resulting mixture was extracted with ethyl acetate and the combined extracts were washed with brine and dried (MgSO$_4$). The solvent was removed and the residue was purified by chromatography on silica gel (CH$_2$Cl$_2$/MeOH 98:2→90:10) to afford the title compound as a colorless foam-like solid.

Yield: 0.19 g (50% of theory); Mass spectrum (ESI$^-$): m/z=410 [M−H]$^-$

Intermediate XXIX

4-Bromo-5-fluoro-1-methyl-1H-pyridin-2-one

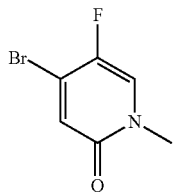

Methyl iodide (0.9 mL) was added to a mixture of potassium carbonate (2.34 g) and 4-bromo-5-fluoro-1H-pyridin-2-one (2.50 g) in N,N-dimethylformamide (25 mL) at room temperature. The mixture was stirred at room temperature overnight and then water was added. The resulting mixture was extracted with ethyl acetate and the combined extracts were washed with brine and dried (MgSO$_4$). The solvent was evaporated to afford the crude title compound that was recrystallized from Et$_2$O.

Yield: 1.22 g (45% of theory); Mass spectrum (ESI$^+$): m/z=206/208 (Br) [M+H]$^+$.

Example 1

3-{(S)-1-[4-(1,5-Dimethyl-6-oxo-1,6-dihydro-pyridazin-3-yl)-phenyl]-ethyl}-(S)-6-(2-hydroxy-2-methyl-propyl)-6-phenyl-[1,3]oxazinan-2-one

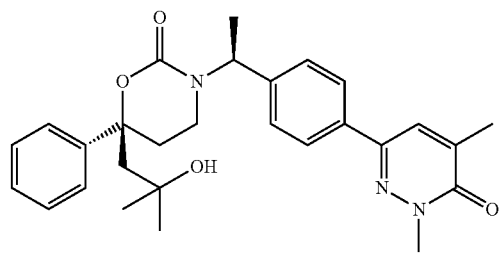

2 M aqueous Na$_2$CO$_3$ solution (0.31 mL) was added to a solution of (S)-6-(2-hydroxy-2-methylpropyl)-6-phenyl-3-[(S)-1-(4-(4,4,5,5-tetramethyl-1,3,2-dioxaborolan-2-yl)phenyl)ethyl]-1,3-oxazinan-2-one (0.15 g) and 6-chloro-2,4-dimethyl-2H-pyridazin-3-one (75 mg) in N,N-dimethylformamide (1 mL). The resulting mixture was sparged with argon for 10 min, before [1,1'-bis(diphenylphosphino)ferrocene]-dichloropalladium(II)dichloromethane complex (15 mg) was added. The mixture was heated to 100° C. and stirred at this temperature overnight. After cooling to ambient temperature, water was added and the resulting mixture was extracted with ethyl acetate. The combined organic extracts were washed with brine, dried (MgSO$_4$), and concentrated. The residue was purified by chromatography on silica gel (CH$_2$Cl$_2$/MeOH 98:2→80:20) to afford the title compound.

Yield: 0.10 g (67% of theory); LC (method 1): $t_R$=3.17 min; Mass spectrum (ESI$^+$): m/z=476 [M+H]$^+$.

The following compounds were obtained in analogy to Example 1: The reactions were carried out using either the bromo, chloro, or trifluoromethanesulfonyloxy derivatized coupling partners (=electrophilic component).

Example 2

3-{(S)-1-[4-(1,4-Dimethyl-6-oxo-1,6-dihydro-pyridazin-3-yl)-phenyl]-ethyl}-(S)-6-(2-hydroxy-2-methyl-propyl)-6-phenyl-[1,3]oxazinan-2-one

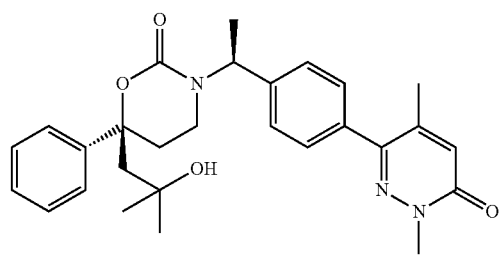

LC (method 1): $t_R$=2.99 min; Mass spectrum (ESI$^+$): m/z=476 [M+1-1]$^+$

Example 3

3-{(S)-1-[4-(2,3-Dimethyl-3H-benzoimidazol-5-yl)-phenyl]-ethyl}-(S)-6-(2-hydroxy-2-methyl-propyl)-6-phenyl-[1,3]oxazinan-2-one

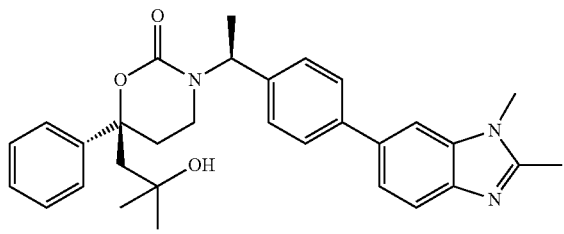

Mass spectrum (ESI⁺): m/z=498 [M+H]⁺.

Example 4

(S)-6-(2-Hydroxy-2-methyl-propyl)-3-{(S)-1-[4-(3-methyl-3H-benzoimidazol-5-yl)-phenyl]-ethyl}-6-phenyl-[1,3]oxazinan-2-one

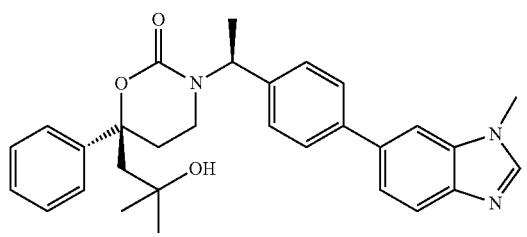

LC (method 1): $t_R$=2.54 min; Mass spectrum (ESI⁺): m/z=484 [M+H]⁺.

Example 5

(S)-6-(2-Hydroxy-2-methyl-propyl)-3-{(S)-1-[4-(1-methyl-1H-benzoimidazol-5-yl)-phenyl]-ethyl}-6-phenyl-[1,3]oxazinan-2-one

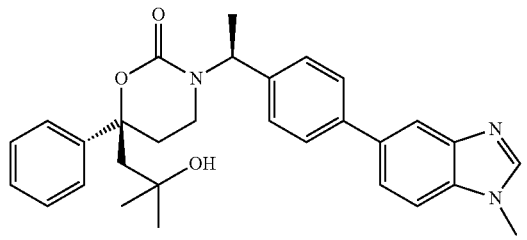

LC (method 1): $t_R$=2.44 min; Mass spectrum (ESI⁺): m/z=484 [M+H]±.

Example 6

3-{(S)-1-[4-(1,2-Dimethyl-1H-benzoimidazol-5-yl)-phenyl]-ethyl}-(S)-6-(2-hydroxy-2-methyl-propyl)-6-phenyl-[1,3]oxazinan-2-one

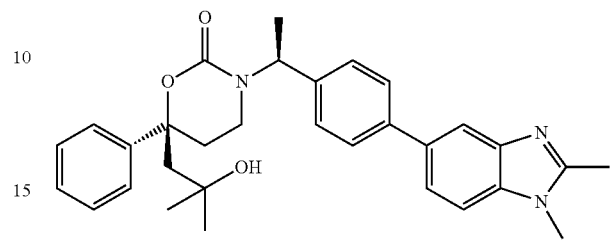

LC (method 1): $t_R$=2.45 min; Mass spectrum (ESI⁺): m/z=498 [M+1-1]⁺.

Example 7

3-{(S)-1-[4-(1-Cyclopropylmethyl-6-oxo-1,6-dihydro-pyridazin-3-yl)-phenyl]-ethyl}-(S)-6-(2-hydroxy-2-methyl-propyl)-6-phenyl-[1,3]oxazinan-2-one

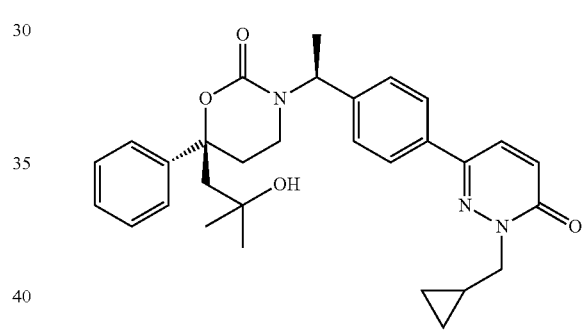

LC (method 1): $t_R$=3.46 min; Mass spectrum (ESI⁺): m/z=502 [M+1-1]⁺.

Example 8

3-{(S)-1-[4-(1-Cyclopropyl-6-oxo-1,6-dihydro-pyridazin-3-yl)-phenyl]-ethyl}-(S)-6-(2-hydroxy-2-methyl-propyl)-6-phenyl-[1,3]oxazinan-2-one

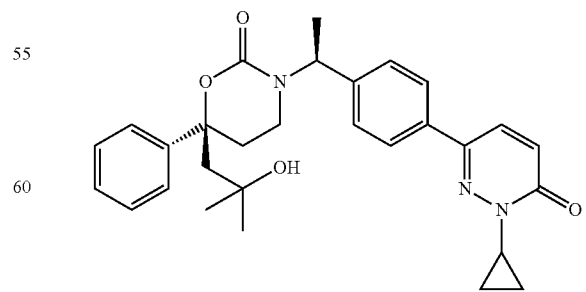

LC (method 1): $t_R$=3.22 min; Mass spectrum (ESI⁺): m/z=488 [M+H]⁺.

Example 9

3-{(S)-1-[4-(1-Cyclopropyl-2-oxo-1,2-dihydro-pyridin-4-yl)-phenyl]-ethyl}-(S)-6-(2-hydroxy-2-methyl-propyl)-6-phenyl-[1,3]oxazinan-2-one

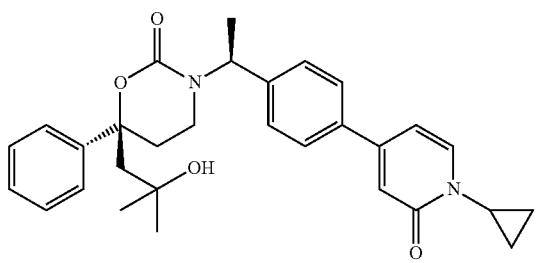

LC (method 2): $t_R$=2.41 min; Mass spectrum (ESI$^+$): m/z=487 [M+H]$^+$.

Trifluoro-methanesulfonic acid 1-cyclopropyl-2-oxo-1,2-dihydro-pyridin-4-yl ester was employed as the coupling partner under the conditions described above

Example 10

3-{(S)-1-[4-(1-Cyclopropylmethyl-6-oxo-1,6-dihydro-pyridin-3-yl)-phenyl]-ethyl}-(S)-6-(2-hydroxy-2-methyl-propyl)-6-phenyl-[1,3]oxazinan-2-one

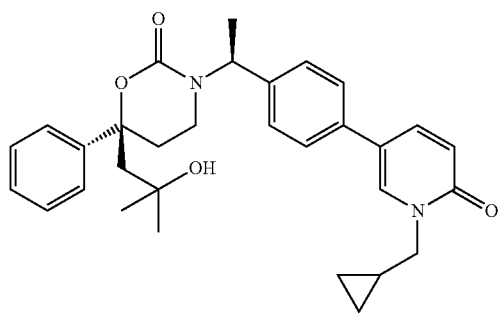

Mass spectrum (ESI$^+$): m/z=501 [M+1-1]$^+$.

Example 11

(R)-6-Methoxymethyl-3-{(S)-1-[4-(6-methyl-pyridazin-3-yl)-phenyl]-ethyl}-6-phenyl-1-[1,3]oxazinan-2-one

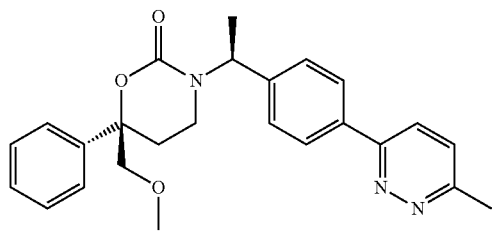

LC (method 1): $t_R$=2.92 min; Mass spectrum (ESI$^+$): m/z=418 [M+H]$^+$

Example 12

(R)-6-Methoxymethyl-3-{(S)-1-[4-(1-methyl-6-oxo-1,6-dihydro-pyridin-3-yl)-phenyl]-ethyl}-6-phenyl-[1,3]oxazinan-2-one

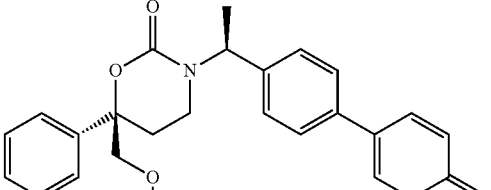

LC (method 1): $t_R$=2.98 min; Mass spectrum (ESI$^+$): m/z=433 [M+H]$^+$

Example 13

(R)-6-Methoxymethyl-3-{(S)-1-[4-(1-methyl-2-oxo-1,2-dihydro-pyridin-4-yl)-phenyl]-ethyl}-6-phenyl-[1,3]oxazinan-2-one

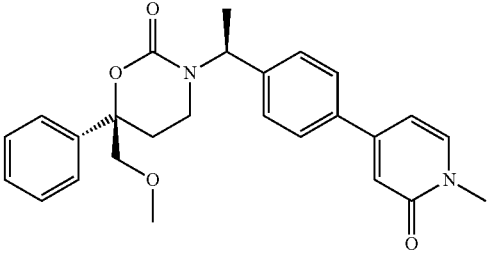

LC (method 1): $t_R$=2.92 min; Mass spectrum (ESI$^+$): m/z=433 [M+H]$^+$

Trifluoro-methanesulfonic acid 1-methyl-2-oxo-1,2-dihydro-pyridin-4-yl ester was used as the coupling partner under the conditions described above.

Example 14

3-{(S)-1-[4-(5-Fluoro-1-methyl-2-oxo-1,2-dihydro-pyridin-4-yl)-phenyl]-ethyl}-(S)-6-(2-hydroxy-2-methyl-propyl)-6-phenyl-[1,3]oxazinan-2-one

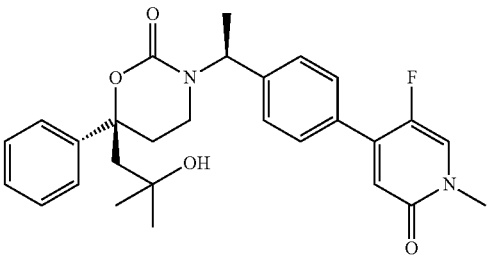

Mass spectrum (ESI$^+$): m/z=479 [M+H]$^+$

4-Bromo-5-fluoro-1-methyl-1H-pyridin-2-one was used as the coupling partner under the conditions described above.

Example 15

5-(4-{(S)-1-[(S)-6-(2-Hydroxy-2-methyl-propyl)-2-oxo-6-phenyl-[1,3]oxazinan-3-yl]-ethyl}-phenyl)-pyridine-2-carboxylic acid ethylamide

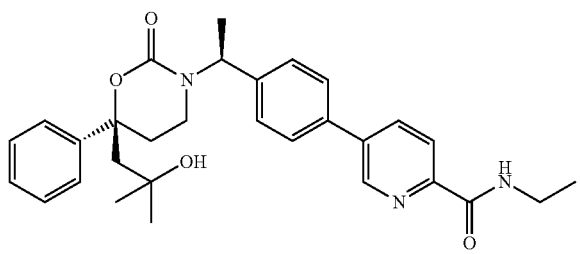

2-(1H-Benzotriazol-1-yl)-1,1,3,3-tetramethyluronium tetrafluoroborate (75 mg) was added to a solution of 5-(4-{(S)-1-[(S)-6-(2-hydroxy-2-methyl-propyl)-2-oxo-6-phenyl-[1,3]oxazinan-3-yl]-ethyl}-phenyl)-pyridine-2-carboxylic acid (0.10 g) and diisopropylethyl-amine (50 µL) in N,N-dimethylformamide (1 mL) at room temperature. The resulting solution was stirred for 25 min, before ethylamine (70% in water, 50 µL) was added. The solution was stirred at room temperature overnight and then concentrated under reduced pressure. The crude product was purified by HPLC on reversed phase (MeCN/H$_2$O) to afford the title compound as a foam-like solid.

Yield: 25 mg (24% of theory); TLC: r$_f$=0.37 (silica gel; CH$_2$Cl$_2$/MeOH 95:5);

Mass spectrum (ESI$^+$): m/z=502 [M+1-1]$^+$.

The following compounds were obtained in analogy to Example 15:

Example 16

5-(4-{(S)-1-[(S)-6-(2-Hydroxy-2-methyl-propyl)-2-oxo-6-phenyl-[1,3]oxazinan-3-yl]-ethyl}-phenyl)-pyridine-2-carboxylic acid methylamide

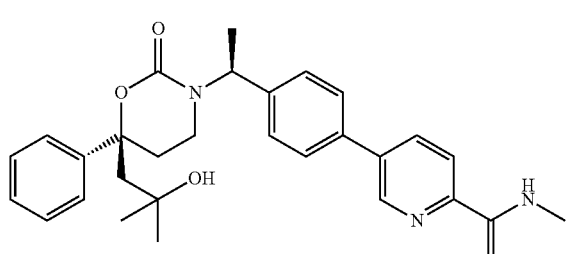

TLC: r$_f$=0.37 (silica gel; CH$_2$Cl$_2$/MeOH 95:5); Mass spectrum (ESI$^+$): m/z=488 [M+H]$^+$. Methylamine was the coupling partner.

Example 17

(4-{(S)-1-[(S)-6-(2-Hydroxy-2-methyl-propyl)-2-oxo-6-phenyl-[1,3]oxazinan-3-yl]-ethyl}-phenyl)-pyridine-2-carboxylic acid dimethylamide

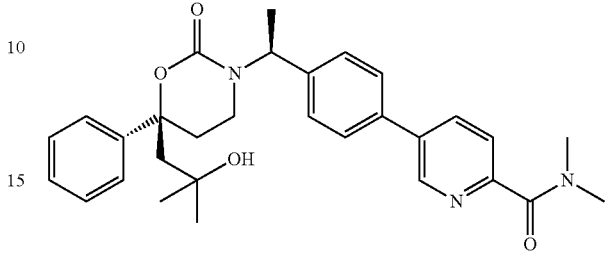

TLC: r$_f$=0.30 (silica gel; CH$_2$Cl$_2$/MeOH 95:5); Mass spectrum (ESI$^+$): m/z=502 [M+H]$^+$. Dimethylamine was the coupling partner.

Example 18

(S)-6-(2-Hydroxy-2-methyl-propyl)-6-phenyl-3-[(S)-1-(4-piperidin-4-yl-phenyl)-ethyl]-[1,3]oxazinan-2-one

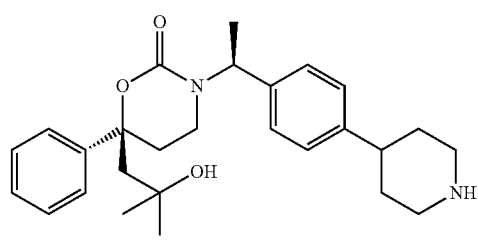

Trifluoroacetic acid (0.40 mL) was added to a solution of 4-(4-{(S)-1-[(S)-6-(2-hydroxy-2-methyl-propyl)-2-oxo-6-phenyl-[1,3]oxazinan-3-yl]-ethyl}-phenyl)-piperidine-1-carboxylic acid tert-butyl ester (0.29 g) in dichloromethane (10 mL). The resulting solution was stirred at room temperature overnight. Then, more dichloromethane was added and the solution was neutralized using aqueous saturated NaHCO$_3$ solution. The organic phase was separated, washed with water, and dried (MgSO$_4$). The solvent was removed under reduced pressure to yield the title compound.

Yield: 0.22 g (93% of theory); LC (method 1): t$_R$=2.09 min; Mass spectrum (ESI$^+$): m/z=437 [M+H]$^+$.

Example 19

3-{(S)-1-[4-(1-Acetyl-piperidin-4-yl)-phenyl]-ethyl}-(S)-6-(2-hydroxy-2-methyl-propyl)-6-phenyl-[1,3]oxazinan-2-one

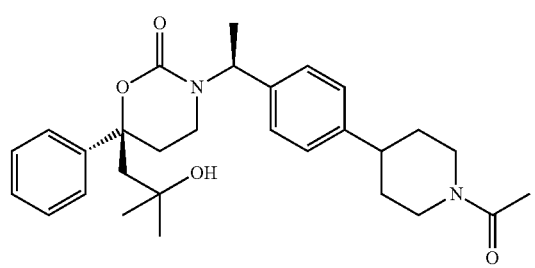

Triethylamine (0.10 mL), acetic anhydride (50 μL), and 4-dimethylaminopyridine (5 mg) were added consecutively to (S)-6-(2-hydroxy-2-methyl-propyl)-6-phenyl-3-[(S)-1-(4-piperidin-4-yl-phenyl)-ethyl]-[1,3]oxazinan-2-one (0.12 g) dissolved in tetrahydrofuran (5 mL) at room temperature. The solution was stirred at room temperature for 4 h and then diluted with ethyl acetate. The resulting solution was washed with aqueous saturated NaHCO$_3$ solution and brine and dried (Na$_2$SO$_4$). After removal of the solvent, the residue was purified by chromatography on silica gel (CH$_2$Cl$_2$/MeOH 98:2→90:10) to afford the title compound as a colorless foam-like solid.

Yield: 80 mg (61% of theory); TLC: r$_f$=0.60 (silica gel; CH$_2$Cl$_2$/MeOH 90:10);

Mass spectrum (ESI$^+$): m/z=479 [M+H]$^+$.

Example 20

4-(4-{(S)-1-[(S)-6-(2-Hydroxy-2-methyl-propyl)-2-oxo-6-phenyl-[1,3]oxazinan-3-yl]-ethyl}-phenyl)-piperidine-1-carboxylic acid methyl ester

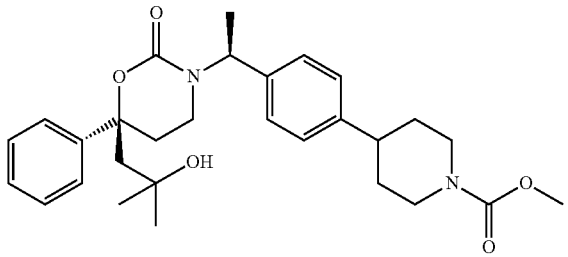

Triethylamine (0.10 mL) and methyl chloroformate (24 μL) were added consecutively to (S)-6-(2-hydroxy-2-methyl-propyl)-6-phenyl-3-[(S)-1-(4-piperidin-4-yl-phenyl)-ethyl]-[1,3]oxazinan-2-one (0.12 g) dissolved in dichloromethane (5 mL) at room temperature. The resulting solution was stirred at room temperature overnight and then diluted with dichloromethane. The resulting solution was washed with water and brine and dried (Na$_2$SO$_4$). After removal of the solvent, the residue was purified by chromatography on silica gel (CH$_2$Cl$_2$/MeOH 99:1→90:10) to afford the title compound as a foam-like solid.

Yield: 100 mg (70% of theory); TLC: r$_f$=0.60 (silica gel; CH$_2$Cl$_2$/MeOH 90:10); Mass spectrum (ESI$^+$): m/z=495 [M+H]$^+$.

Example 21

(S)-6-(2-Hydroxy-2-methyl-propyl)-3-{(S)-1-[4-(1-methyl-piperidin-4-yl)-phenyl]-ethyl}-6-phenyl-[1,3]oxazinan-2-one

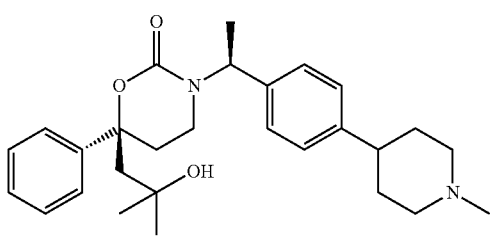

Acetic acid (27 μL) and NaHB(O$_2$CCH$_3$)$_3$ (160 mg) were added to a solution of (S)-6-(2-hydroxy-2-methyl-propyl)-6-phenyl-3-[(S)-1-(4-piperidin-4-yl-phenyl)-ethyl]-[1,3]oxazinan-2-one (200 mg) and formaldehyde (37% in water, 70 μL) in tetrahydrofuran (5 mL) at room temperature. After stirring the solution at room temperature overnight, ethyl acetate and 1 M aqueous NaOH solution were added and the resulting mixture was stirred for another 10 min. Then, the organic layer was separated and washed with water and brine and dried (MgSO$_4$). The solvent was evaporated and the residue was purified by HPLC on reversed phase (MeCN/H$_2$O/F$_3$CCO$_2$H) to afford the title compound as its trifluoroacetic acid salt.

Yield: 120 mg (46% of theory); LC (method 1): t$_R$=2.18 min; Mass spectrum (ESI$^+$): m/z=451 [M+H]$^+$.

Example 22

(S)-6-(2-Hydroxy-2-methyl-propyl)-3-{(S)-1-[4-(1-methanesulfonyl-piperidin-4-yl)-phenyl]-ethyl}-6-phenyl-[1,3]oxazinan-2-one

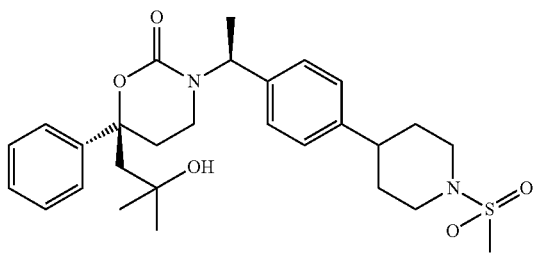

MeSO$_2$Cl (29 μL) was added to a solution of (S)-6-(2-hydroxy-2-methyl-propyl)-6-phenyl-3-[(S)-1-(4-piperidin-4-yl-phenyl)-ethyl]-[1,3]oxazinan-2-one (150 mg) and triethylamine (100 μL) in dichloromethane (3 mL) at room temperature. After stirring the solution at room temperature overnight, more dichloromethane was added and the resulting solution was washed with aqueous NaHCO$_3$ solution, water, and brine. The organic solution was then dried (MgSO$_4$) and concentrated. The residue was purified by HPLC on reversed phase (MeCN/H$_2$O/NH$_3$) to afford the title compound.

Yield: 52 mg (29% of theory); Mass spectrum (ESI$^+$): m/z=515 [M+H]$^+$.

Example 23

(S)-6-(2-Hydroxy-2-methyl-propyl)-6-phenyl-3-((S)-1-{4-[1-((S)-tetrahydro-furan-2-carbonyl)-piperidin-4-yl]-phenyl}-ethyl)-[1,3]oxazinan-2-one

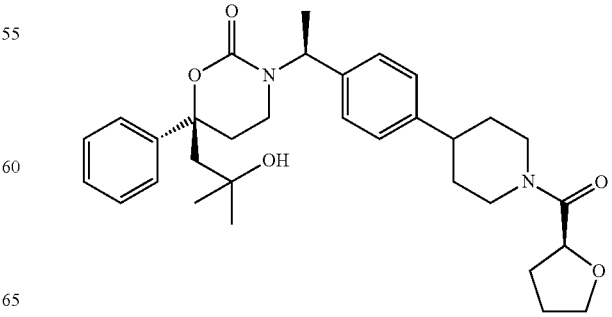

2-(1H-Benzotriazol-1-yl)-1,1,3,3-tetramethyluronium tetrafluoroborate (125 mg) was added to a solution of (S)-tetrahydro-furan-2-carboxylic acid (45 mg) and diisopropyl-ethyl-amine (200 μL) in N,N-dimethylformamide (2 mL) at room temperature. The resulting solution was stirred for 30 min, before (S)-6-(2-hydroxy-2-methyl-propyl)-6-phenyl-3-[(S)-1-(4-piperidin-4-yl-phenyl)-ethyl]-[1,3]oxazinan-2-one (150 mg) dissolved in dimethylformamide (1 mL) was added. The resulting solution was stirred at room temperature overnight and then concentrated under reduced pressure. The crude product was purified by HPLC on reversed phase (MeCN/H$_2$O/NH$_3$) to afford the title compound.

Yield: 110 mg (60% of theory); LC (method 1): t$_R$=3.20 min; Mass spectrum (ESI$^+$): m/z=535 [M+1-1]$^+$ The following compounds were obtained in analogy to Example 23:

Example 24

(S)-6-(2-Hydroxy-2-methyl-propyl)-6-phenyl-3-((S)-1-{4-[1-((R)-tetrahydro-furan-2-carbonyl)-piperidin-4-yl]-phenyl}-ethyl)-[1,3]oxazinan-2-one

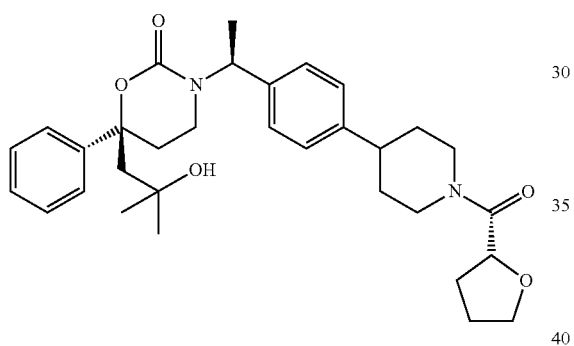

LC (method 1): t$_R$=3.20 min; Mass spectrum (ESI$^+$): m/z=535 [M+14]$^+$

Example 25

(S)-6-(2-Hydroxy-2-methyl-propyl)-6-phenyl-3-((S)-1-{4-[1-(2-hydroxy-2-propyl-carbonyl)-piperidin-4-yl]-phenyl}-ethyl)-[1,3]oxazinan-2-one

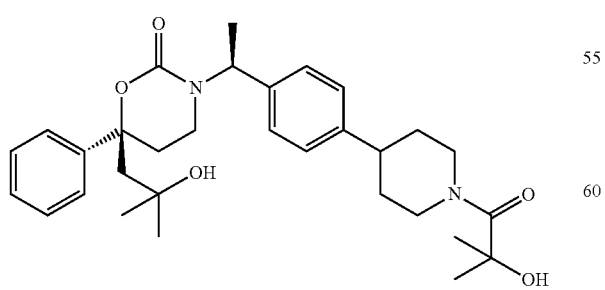

LC (method 1): t$_R$=3.17 min; Mass spectrum (ESI$^+$): m/z=535 [M+14]$^+$

Example 26

(S)-6-(2-Hydroxy-2-methyl-propyl)-3-((S)-1-{4-[1-((S)-1-methyl-pyrrolidine-2-carbonyl)-piperidin-4-yl]-phenyl}-ethyl)-6-phenyl-[1,3]oxazinan-2-one

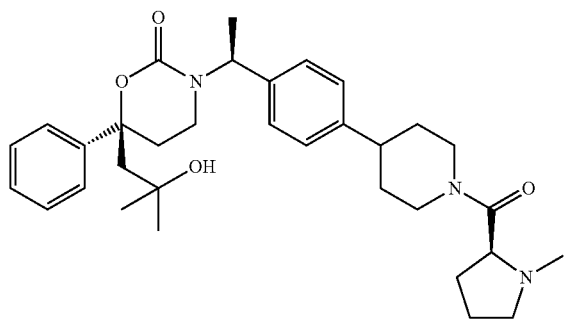

Mass spectrum (ESI$^+$): m/z=548 [M+H]$^+$

Example 27

(S)-6-(2-Hydroxy-2-methyl-propyl)-3-((S)-1-{4-[1-((R)-1-methyl-pyrrolidine-2-carbonyl)-piperidin-4-yl]-phenyl}-ethyl)-6-phenyl-[1,3]oxazinan-2-one

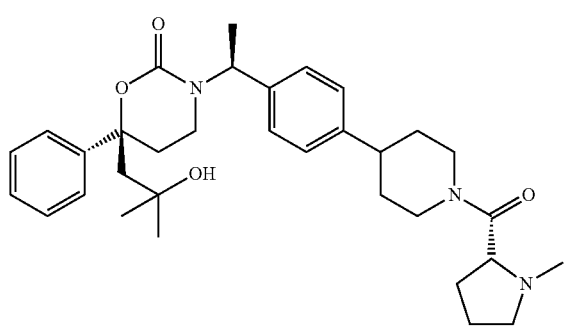

LC (method 1): t$_R$=2.37 min; Mass spectrum (ESI$^+$): m/z=548 [M+H]$^+$

Example 28

3-{(S)-1-[4-(3H-Benzotriazol-5-yl)-phenyl]-ethyl}-(S)-6-(2-hydroxy-2-methyl-propyl)-6-phenyl-[1,3]oxazinan-2-one

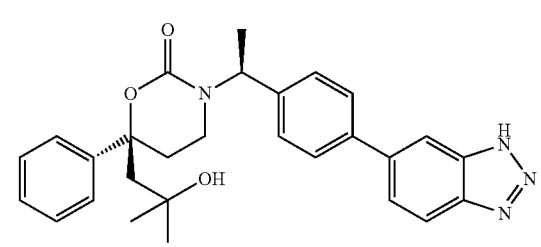

A solution of NaNO$_2$ (0.16 g) in water (2 mL) was added dropwise to an ice-cold solution of 3-[(S)-1-(3',4'-diamino-biphenyl-4-yl)-ethyl]-(S)-6-(2-hydroxy-2-methyl-propyl)-6-phenyl-[1,3]oxazinan-2-one (0.43 g) in acetic acid (10 mL). The resulting mixture was stirred with cooling for 2 h and at room temperature for another 1 h. Then, water (100 mL) was added and the resulting mixture is extracted with ethyl acetate. The combined organic extracts were washed with saturated aqueous NaHCO$_3$ solution, water, and brine and dried (Na$_2$SO$_4$). The solvent was removed and the residue was purified by chromatography on silica gel (ethyl acetate/MeOH 98:2→80:20) to afford the title compound as a foam-like solid.

Yield: 0.30 g (69% of theory); LC (method 1): t$_R$=3.02 min; Mass spectrum (ESI$^+$): m/z=471 [M+H]$^+$.

Example 29

(S)-6-(2-Hydroxy-2-methyl-propyl)-3-{(S)-1-[4-(2-methyl-3H-benzoimidazol-5-yl)-phenyl]-ethyl}-6-phenyl-[1,3]oxazinan-2-one

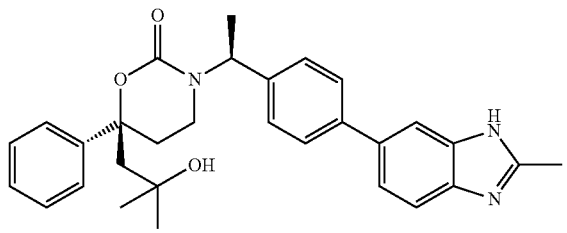

3-[(S)-1-(3',4'-Diamino-biphenyl-4-yl)-ethyl]-(S)-6-(2-hydroxy-2-methyl-propyl)-6-phenyl-[1,3]oxazinan-2-one (120 mg) taken up in acetic acid (2 mL) was stirred under microwave irradiation at 150° C. for 30 min. After cooling to ambient temperature, the mixture was concentrated under reduced pressure and the residue was purified by HPLC on reversed phase (MeCN/H$_2$O) to afford the title compound.

Yield: 77 mg (61% of theory); Mass spectrum (ESI$^+$): m/z=484 [M+H]$^+$.

Examples 30 and 31

3-[(S)-1-(4-Bromo-phenyl)-ethyl]-(R)-6-methoxymethyl-6-phenyl-[1,3]oxazinan-2-one and 3-[(S)-1-(4-Bromo-phenyl)-ethyl]-(S)-6-methoxymethyl-6-phenyl-[1,3]oxazinan-2-one

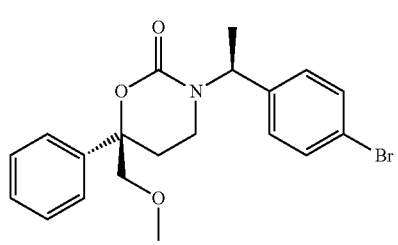

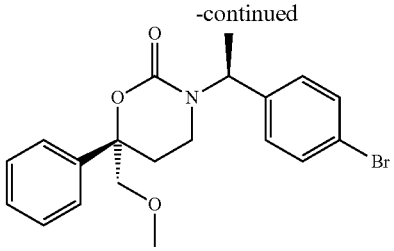

Triphosgene (157 mg) was added to an ice-cold solution of 4-[(S)-1-(4-bromo-phenyl)-ethylamino]-1-methoxy-2-phenyl-butan-2-ol (1:1 diastereomeric mixture, 200 mg) and EtNiPr$_2$ (91 µL) in dichloromethane (5 mL). The resulting solution was stirred with cooling for 2 h and at room temperature overnight. Then, the solution was concentrated under reduced pressure and the residue was purified by HPLC on reversed phase (MeCN/H$_2$O/NH$_3$) to afford the title compounds in separate fractions.

Example 30

3-[(S)-1-(4-Bromo-phenyl)-ethyl]-(R)-6-methoxymethyl-6-phenyl-[1,3]oxazinan-2-one Yield: 45 mg (21% of theory). Mass spectrum (ESI$^+$): m/z=404 [M+H]$^+$. $^1$H NMR (400 MHz, DMSO-d$_6$) δ 1.41 (d, J=7.1 Hz, 3H), 2.19 (td, J=11.2, 5.2 Hz, 1H), 2.24-2.34 (m, 1H), 2.34-2.41 (m, 1H), 3.02-3.09 (m, 1H), 3.27 (s, 3H), 3.49 (d, B part of an AB signal, J=10.6 Hz, 1H), 3.53 (d, A part of an AB signal, J=10.6 Hz, 1H), 5.34 (q, J=7.0 Hz, 1H), 6.80 (dm, J=8.4 Hz, 2H), 7.27 (dm, J=8.4 Hz, 2H), 7.32-7.42 (m, 5H).

Example 31

3-[(S)-1-(4-Bromo-phenyl)-ethyl]-(S)-6-methoxymethyl-6-phenyl-[1,3]oxazinan-2-one Yield: 45 mg (21% of theory). Mass spectrum (ESI$^+$): m/z=404 [M+H]$^+$. $^1$H NMR (400 MHz, DMSO-d$_6$) δ 1.20 (d, J=7.2 Hz, 3H), 2.13-2.23 (m, 1H), 2.32-2.40 (m, 1H), 2.63-2.72 (m, 1H), 2.73-2.81 (m, 1H), 3.26 (s, 3H), 3.48 (d, B part of an AB signal, J=10.6 Hz, 1H), 3.55 (d, A part of an AB signal, J=10.6 Hz, 1H), 5.35 (q, J=7.2 Hz, 1H), 7.19 (dm, J=8.4 Hz, 2H), 7.32-7.45 (m, 5H), 7.53 (dm, J=8.4 Hz, 2H).

Example 32

(S)-6-(2-Methyl-allyl)-3-{(S)-1-[4-(5-methyl-[1,3,4]oxadiazol-2-yl)-phenyl]-ethyl}-6-phenyl-[1,3]oxazinan-2-one

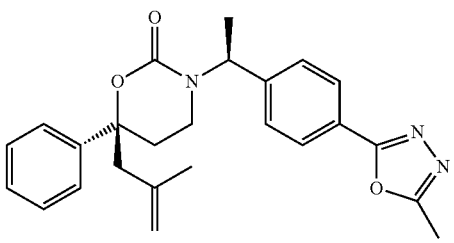

A mixture of 4-{(S)-1-[(S)-6-(2-hydroxy-2-methyl-propyl)-2-oxo-6-phenyl-[1,3]oxazin-an-3-yl]-ethyl}-benzoic acid hydrazide (90 mg), toluene-4-sulfonic acid monohydrate (10 mg), and 1,1,1-trimethoxy-ethane (1 ml) was stirred at room temperature for 1 h, at 80° C. for 2 h, and finally at reflux temperature for 1.5 h. After cooling to ambient temperature, ethyl acetate was added and the resulting mixture was washed with aqueous NaHCO₃ solution and brine. The solvent was removed under reduced pressure and the residue was purified by chromatography on silica gel (CH₂Cl₂/MeOH 99:1→95:5) to afford the title compound as a colorless resin-like solid.

Yield: 55 mg (60% of theory); TLC: $r_f$=0.70 (silica gel; CH₂Cl₂/MeOH 95:5); Mass spectrum (ESI⁺): m/z=418 [M+H]⁺.

Example 33

(S)-6-(2-Hydroxy-2-methyl-propyl)-3-{(S)-1-[4-(1-methyl-2-oxo-piperidin-4-yl)-phenyl]-ethyl}-6-phenyl-[1,3]oxazinan-2-one

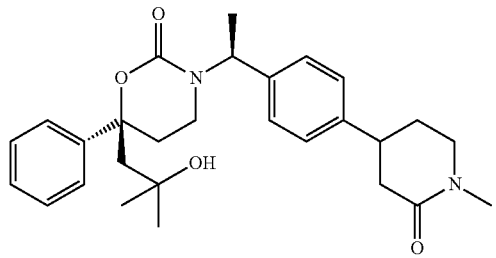

PtO₂ (50 mg) was added to (S)-6-(2-hydroxy-2-methyl-propyl)-3-{LS)-1-[4-(1-methyl-2-oxo-1,2-dihydro-pyridin-4-yl)-phenyl]-ethyl}-6-phenyl-[1,3]oxazinan-2-one (150 mg; the compound was obtained from (S)-6-(2-hydroxy-2-methylpropyl)-6-phenyl-3-[(S)-1-(4-(4,4,5,5-tetramethyl-1,3,2-dioxaborolan-2-yl)phenyl)ethyl]-1,3-oxazinan-2-one and 4-bromo-1-methyl-1H-pyridin-2-one employing the procedure described for Example 1) dissolved in methanol (5 mL). The resulting mixture was shaken in hydrogen atmosphere (50 psi) for 8 h. Then, the mixture was filtered and the filtrate was concentrated under reduced pressure. The residue was purified by HPLC on reversed phase (MeCN/H₂O) to afford the title compound.

Yield: 100 mg (66% of theory); LC (method 1): $t_R$=2.89 min; Mass spectrum (ESI⁺): m/z=482 [M+NH₄]⁺.

The following compound was obtained in analogy to Example 33:

Example 34

(S)-6-(2-Hydroxy-2-methyl-propyl)-3-{(S)-1-[4-(1-methyl-6-oxo-piperidin-3-yl)-phenyl]-ethyl}-6-phenyl-[1,3]oxazinan-2-one

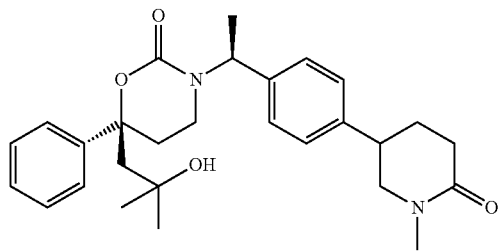

LC (method 1): $t_R$=2.89 min; Mass spectrum (ESI⁺): m/z=465 [M+H]⁺

The starting compound, (S)-6-(2-hydroxy-2-methyl-propyl)-3-{(S)-1-[4-(1-methyl-6-oxo-1,6-dihydro-pyridin-3-yl)-phenyl]-ethyl}-6-phenyl-[1,3]oxazinan-2-one, was obtained from (S)-6-(2-hydroxy-2-methylpropyl)-6-phenyl-3-[(S)-1-(4-(4,4,5,5-tetramethyl-1,3,2-dioxaborolan-2-yl)phenyl)ethyl]-1,3-oxazinan-2-one and 5-bromo-1-methyl-1H-pyridin-2-one employing the procedure described for Example 1.

Example 35

4-(4-{(S)-1-[(S)-6-(2-Hydroxy-2-methyl-propyl)-2-oxo-6-phenyl-[1,3]oxazinan-3-yl]-ethyl}-phenyl)-piperidine-1-carboxylic acid methylamide

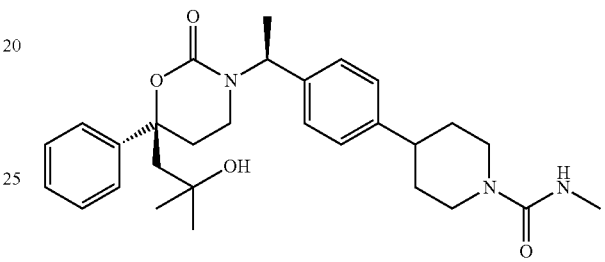

MeNH₂*HCl (27 mg) and K₂CO₃ (93 mg) were added to a solution of 4-nitrophenyl chloroformate (66 mg) in acetonitrile (2 mL) at room temperature. The resulting mixture was stirred at room temperature for 4 h, before (S)-6-(2-hydroxy-2-methyl-propyl)-6-phenyl-3-[(S)-1-(4-piperidin-4-yl-phenyl)-ethyl]-[1,3]oxazinan-2-one (110 mg) and NEt₃ (53 µL) were added. The mixture was further stirred at room temperature overnight. Then, diluted aqueous ammonia solution was added and the resulting mixture was filtered. The filtrate was concentrated under reduced pressure and the residue was purified by HPLC on reversed phase (MeOH/H₂O/NH₃) to afford the title compound.

Yield: 100 mg (80% of theory); Mass spectrum (ESI⁺): m/z=494 [M+H]⁺.

Example 36

4-((S)-4-{1-[(S)-6-(2-Hydroxy-2-methyl-propyl)-2-oxo-6-phenyl-[1,3]oxazinan-3-yl]-ethyl}-phenyl)-piperidine-1-carboxylic acid dimethylamide

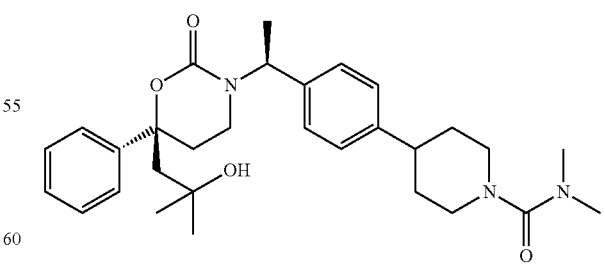

Dimethylcarbamoyl chloride (26 µL) was added to a solution of (S)-6-(2-hydroxy-2-methyl-propyl)-6-phenyl-3-[(S)-1-(4-piperidin-4-yl-phenyl)-ethyl]-[1,3]oxazinan-2-one (120 mg) and pyridine (40 µL) in N,N-dimethylformamide (2 mL) at room temperature. The solution was stirred at room temperature for 5 h, before another portion of dimethylcarbamoyl chloride (26 μL) and pyridine (20 μL) were added. The solution was stirred at room temperature overnight. Then, diluted aqueous ammonia solution was added and the resulting mixture was concentrated under reduced pressure. The residue was purified by HPLC on reversed phase (MeOH/H$_2$O/NH$_3$) to afford the title compound.

Yield: 70 mg (50% of theory); LC (method 1): t$_R$=3.17 min; Mass spectrum (ESI$^+$): m/z=508 [M+H]$^+$.

Example 37

3-{(S)-1-[4-(1,2-dimethyl-1H-benzo[d]imidazol-5-yl)phenyl]ethyl}-6-(2-hydroxy-2-methylpropyl)-6-isopropyl-1,3-oxazinan-2-one

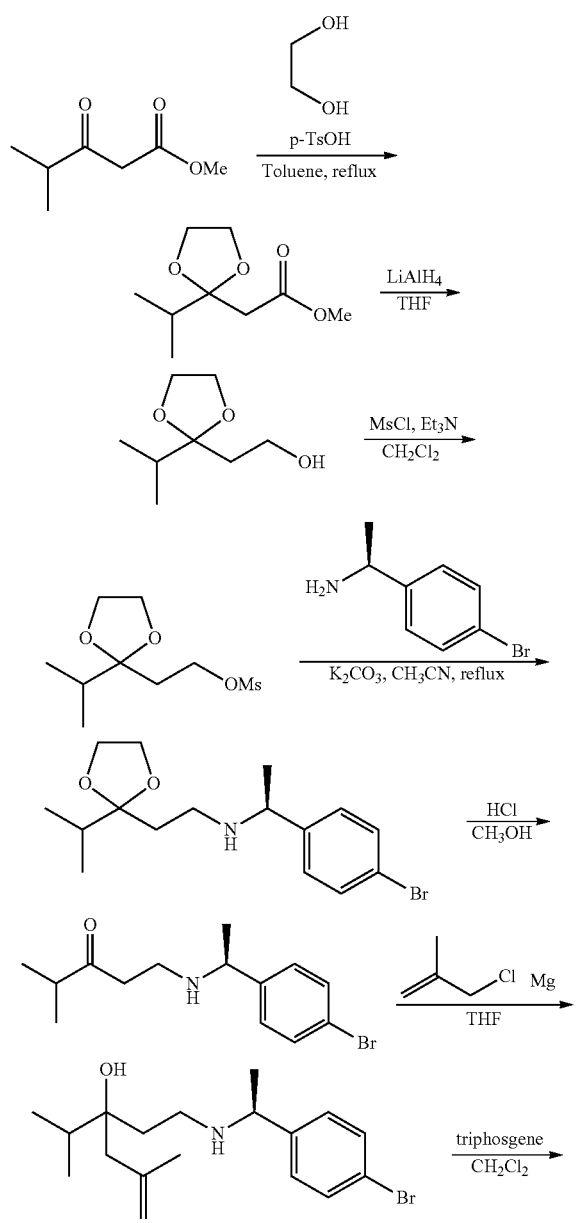

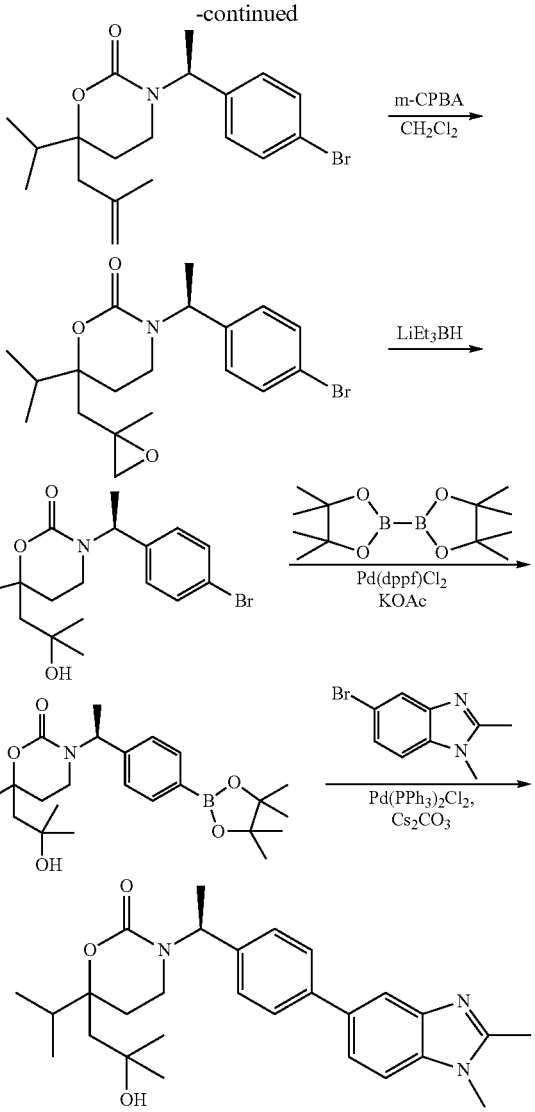

Step 1

To a solution of methyl 4-methyl-3-oxopentanoate (72 g, 0.5 mol) and ethylene glycol (56 g, 1 mol) in toluene (500 mL) was added 4-methylbenzenesulfonic acid (1.9 g, 0.01 mol). The mixture was stirred at reflux with a Dean-Stark trap to remove water. The reaction mixture was washed with a small amount of water and brine, dried over anhydrous Na$_2$SO$_4$, and concentrated in vacuum to give the crude (2-isopropyl-[1,3]dioxolan-2-yl)-acetic acid methyl ester (67 g 71% yield), which was used for the next step without further purification.

Step 2

In a flame-dried, three-neck flask equipped with an addition funnel, magnetic stirring bar, rubber septum, and a nitrogen inlet, was placed LiAlH$_4$ (3.12 g, 82.1 mmol) and tetrahydrofuran (700 mL). After being cooled at 0° C., a solution of (2-isopropyl-[1,3]dioxolan-2-yl)-acetic acid methyl ester (12 g, 63.8 mmol) in tetrahydrofuran (160 mL) was added dropwise with stirring. The mixture was warmed to room temperature and stirred for 24 hours. The reaction was quenched by adding water (5 mL), 15% aqueous NaOH (10 mL), and water (5 mL) slowly. The organic layer was separated, and the residue was extracted with EtOAc (3×100 mL). The combined organic phase was dried over Na$_2$SO$_4$ and concentrated to afford the crude product, which was purified by column chromatography to give 2-(2-isopropyl-[1,3]dioxolan-2-yl)-ethanol (6.8 g, 67%). $^1$H NMR (CDCl$_3$) δ 0.90 (d, J=6.8 Hz, 6H), 1.87-1.96 (m, 3H), 2.81 (br, 1H), 3.69-3.72 (m, 2H), 3.92-4.01 (m, 4H).

Step 3

To a solution of 2-(2-isopropyl-1,3-dioxolan-2-yl)-ethanol (8.0 g, 50 mmol) and triethylamine (23.5 mL, 170 mmol) in anhydrous CH$_2$Cl$_2$ (120 mL) was added methanesulfonyl chloride (11.6 mL, 150 mmol) at 0° C., and the reaction mixture was stirred at room temperature till the reaction was finished. The reaction mixture was washed with water and brine, dried over Na$_2$SO$_4$, filtered, and concentrated to give the crude methanesulfonic acid 2-(2-isopropyl-[1,3]diox-olan-2-yl)-ethyl ester (12 g), which was used for the next step without further purification.

Step 4

To a solution of methanesulfonic acid 2-(2-isopropyl-[1,3] dioxolan-2-yl)-ethyl ester (12 g, 50 mmol) and (S)-1-(4-bromophenyl)ethanamine (19.9 g, 100 mmol) in CH$_3$CN (250 mL) was added K$_2$CO$_3$ (8 g, 58 mmol), and the mixture was refluxed for 10 h. The solution was filtered, and the filtrate was concentrated to afford the crude product, which was purified by column chromatography to give [(S)-1-(4-bromophenyl)-ethyl]-[2-(2-isopropyl-[1,3]dioxolan-2-yl)-ethyl]-amine (6.5 g, 38%).

Step 5

To a solution of [(S)-1-(4-bromophenyl)-ethyl]-[2-(2-isopropyl-[1,3]dioxolan-2-yl)-ethyl]-amine (6.5 g, 19 mmol) in MeOH (60 mL) was added concentrated aqueous HCl (60 mL). The mixture was stirred at 65° C. till the reaction was finished. The mixture was cooled to 0° C., and the pH of the mixture was adjusted to 7 by adding saturated aqueous NaHCO$_3$. The mixture was concentrated, and the residue was extracted with EtOAc (3×100 mL). The organic layer was washed with brine, dried over Na$_2$SO$_4$, and concentrated to give 1-[(S)-1-(4-bromophenyl)-ethylamino]-4-methyl-pentan-3-one (5.5 g, 97%), which was used for the next step without further purification. $^1$H NMR (CDCl$_3$): δ 1.07 (d, J=6.8 Hz, 6H), 1.29 (d, J=6.4 Hz, 3H), 1.89 (br, 1H), 2.54-2.62 (m, 4H), 2.66-2.69 (m, 1H), 3.68-3.72 (m, 1H), 7.18-7.20 (m, 2H), 7.41-7.44 (m, 2H).

Step 6

To a suspension of Mg (11 g, 458 mmol) and I$_2$ (0.5 g) in anhydrous tetrahydrofuran (50 mL) was added 3-chloro-2-methylprop-1-ene (1 mL) to initiate the reaction. Tetrahydrofuran (300 mL) was added, more solution of 3-chloro-2-methylprop-1-ene (15 mL) in tetrahydrofuran (20 mL) was dropped into the reaction at 0° C. under N$_2$ over 30 min A solution of 1-[(S)-1-(4-bromophenyl)-ethylamino]-4-methyl-pentan-3-one (5 g) in tetrahydrofuran (50 mL) was added dropwise at −78° C. over 45 min. The reaction mixture was stirred at room temperature for 2 h. The reaction was cautiously quenched with saturated aqueous NH$_4$Cl, and the reaction mixture was filtered. The filtrate was extracted with EtOAc (3×100 mL) and the combined extracts were washed with brine, dried over anhydrous Na$_2$SO$_4$, and concentrated in vacuo to give 3-{(S)-2-[1-(4-bromophenyl)-ethylamino]-ethyl}-2,5-dimethyl-hex-5-en-3-ol (6.4 g, 90% yield), which was used for the next step without further purification.

Step 7

To a solution of 3-{(S)-2-[1-(4-bromophenyl)-ethylamino]-ethyl}-2,5-dimethyl-hex-5-en-3-ol (6.4 g, 16.8 mmol) and triethylamine (5.34 g, 52 mmol) in CH$_2$Cl$_2$ (260 mL) was added triphosgene (2.52 g, 8.5 mmol) at 0° C. under N$_2$, and the mixture was stirred at room temperature overnight. The reaction was quenched with water, and the mixture was extracted with CH$_2$Cl$_2$ (3×50 mL). The combined organic layer was washed with brine, dried over Na$_2$SO$_4$, filtered, and concentrated to afford the crude product, which was purified by column chromatography to give two isomers of 3-[(S)-1-(4-bromophenyl)ethyl]-6-isopropyl-6-(2-methylallyl)-1,3-oxazinan-2-one.

Isomer 1: (lower r$_f$ on silica gel TLC, 1.85 g, 27% yield). $^1$H NMR (CDCl$_3$) δ 0.83 (d, J=7.2 Hz, 3H), 0.89 (d, J=7.2 Hz, 3H), 1.45 (d, J=6.8 Hz, 3H), 1.64-1.70 (m, 2H), 1.79 (s, 3H), 1.88-1.95 (m, 1H), 2.20-2.34 (m, 2H), 2.59-2.65 (m, 1H), 3.01-3.08 (m, 1H), 4.70 (s, 1H), 4.87 (s, 1H), 5.68-5.77 (m, 1H), 7.14 (d, J=8.4 Hz, 2H), 7.41 (d, J=8.4 Hz, 2H).

Isomer 2: (higher r$_f$ on silica gel TLC, 1.25 g, 18% yield). $^1$H NMR (CDCl$_3$) δ 0.87 (d, J=6.8 Hz, 3H), 0.92 (d, J=6.8 Hz, 3H), 1.50 (d, J=7.2 Hz, 3H), 1.60-1.66 (m, 1H), 1.78 (s, 3H), 1.73-1.79 (m, 1H), 1.78-2.05 (m, 1H), 2.08 (d, J=14.0 Hz, 1H), 2.30 (d, J=14.0 Hz, 1H), 2.62-2.68 (m, 1H), 2.98-3.05 (m, 1H), 4.64 (s, 1H), 4.84 (s, 1H), 5.70-5.75 (m, 1H), 7.13 (d, J=8.4 Hz, 2H), 7.40 (d, J=8.4 Hz, 2H).

Step 8

To a solution of 3-[(S)-1-(4-bromophenyl)ethyl]-6-isopropyl-6-(2-methylallyl)-1,3-oxazinan-2-one isomer 1 (500 mg, 1.32 mmol) in dry CH$_2$Cl$_2$ (64 mL) was added 3-chloroperoxybenzoic acid (455 g, 2.64 mmol) at room temperature. The reaction mixture was stirred until the starting material was consumed (monitored by TLC). The mixture was diluted with (CH$_3$)$_3$COCH$_3$ (70 mL), washed with 30% aqueous Na$_2$S$_2$O$_3$ and aqueous NaHCO$_3$ (3×), dried over Na$_2$SO$_4$, filtered, and concentrated to give 3-[(S)-1-(4-bromophenyl) ethyl]-6-isopropyl-6-((2-methyloxiran-2-yl)methyl)-1,3-oxazinan-2-one isomer 1 (520 mg, 99%), which was used directly for the next step without further purification.

Step 9

To a solution of 3-[(S)-1-(4-bromophenyl)ethyl]-6-isopropyl-6-((2-methyloxiran-2-yl)methyl)-1,3-oxazinan-2-one isomer 1 (520 mg, 1.32 mmol) in tetrahydrofuran (32 mL) was added dropwise LiEt$_3$BH (13.6 mL, 13.6 mmol) at 0° C. under N$_2$ over 30 min. The resulting solution was stirred at 10-13° C. for 21.5 h. Then aqueous H$_2$O$_2$ (40 mL) was added to the mixture and the resulting solution was diluted with (CH$_3$)$_3$COCH$_3$ (380 mL), and washed with water, 30% aqueous Na$_2$S$_2$O$_3$, and brine. The organic phase was dried over Na$_2$SO$_4$ and filtered. The filtrate was concentrated to give the crude product, which was purified by column chromatography to afford 3-[(S)-1-(4-bromophenyl)ethyl]-6-(2-hydroxy-2-methylpropyl)-6-isopropyl-1,3-oxazinan-2-one isomer 1 (320 mg, 61%). $^1$H NMR (CDCl$_3$) δ 0.82 (d, J=6.8 Hz, 3H), 0.95 (d, J=6.8 Hz, 3H), 1.31 (s, 3H), 1.34 (s, 3H), 1.51 (d, J=10.0 Hz, 3H), 1.61 (d, J=15.2 Hz, 1H), 1.78-1.84 (m, 1H), 1.91 (d, J=15.2 Hz, 1H), 2.02-2.15 (m, 2H), 2.36 (br, 1H), 2.62-2.68 (m, 1H), 3.03-3.09 (m, 1H), 5.73 (t, J=7.2 Hz, 1H), 7.17-7.19 (m, 2H), 7.44-7.48 (m, 2H).

Step 10

To a solution of 3-[(S)-1-(4-bromophenyl)ethyl]-6-(2-hydroxy-2-methylpropyl)-6-isopropyl-1,3-oxazinan-2-one isomer 1 (315 mg, 0.793 mmol) in dimethyl sulfoxide (10 mL) was added 4,4,5,5-tetramethyl-1,3,2-dioxaborolan-2-yl)-1,3,2-dioxaborolane (602 mg, 2.38 mmol), CH$_3$CO$_2$K (770 mg, 79.3 mmol), and Pd[1,1'-bis(diphenylphosphino) ferreocene]$_2$Cl$_2$ (50 mg, 0.06 mmol) under N$_2$ and the reaction mixture was stirred at 90° C. for 4 h. The reaction was quenched with aqueous NH$_4$Cl, and the resulting mixture was extracted with EtOAc. The combined extracts were washed with water and brine. The organic phase was dried over Na$_2$SO$_4$ and filtered. The filtrate was concentrated to give the crude product, which was purified by preparative TLC to give 6-(2-hydroxy-2-methylpropyl)-6-isopropyl-3-{(S)-1-[4-(4,4,5,5-tetramethyl-1,3,2-dioxaborolan-2-yl)phenyl]ethyl}-1,3-oxazinan-2-one isomer 1 (250 mg, 71%).

Step 11

To a solution of 5-bromo-1,2-dimethyl-1H-benzo[d]imidazole (30 mg, 0.13 mmol), 6-(2-hydroxy-2-methylpropyl)-6-isopropyl-3-{(S)-1-[4-(4,4,5,5-tetramethyl-1,3,2-dioxaborolan-2-yl)phenyl]ethyl}-1,3-oxazinan-2-one isomer 1 (15 mg, 0.034 mmol) and $Na_2CO_3$ (10.74 mg, 0.10 mmol) in toluene (3 mL), EtOH (2 mL) and $H_2O$ (1 mL) was added $Pd(PPh_3)_4$ (0.39 mg, 0.003 mmol) at room temperature. The reaction mixture was heated to 100° C. under $N_2$ and stirred at this temperature for 2 h. The formed mixture was concentrated to afford an oil which was poured into $H_2O$ (10 mL) and extracted with EtOAc (10 mL×3). The combined organic layers were concentrated to afford an oil which was purified by preparative TLC and preparative HPLC to afford 3-{(S)-1-[4-(1,2-dimethyl-1H-benzo[d]imidazol-5-yl)phenyl]ethyl}-6-(2-hydroxy-2-methylpropyl)-6-isopropyl-1,3-oxazinan-2-one isomer 1 (5.5 mg, 8.9%). $^1$H NMR ($CD_3OD$) δ 0.79 (d, 3H), 0.89 (d, 3H), 1.21 (s, 1H), 1.22 (s, 6H), 1.51 (m, 3H), 1.62 (m, 1H), 1.82 (m, 2H), 2.03 (m, 1H), 2.12 (m, 1H), 2.52 (m, 3H), 2.72 (m, 1H), 3.72 (m, 3H), 5.62 (m, 1H), 7.31 (m, 2H), 7.42 (m, 2H), 7.55 (m, 2H), 7.69 (s, 1H); Mass spectrum (ESI$^+$): m/z=464 [M+H]$^+$.

The following compound was obtained in analogy to Step 11 of Example 37:

Example 38

6-(2-hydroxy-2-methylpropyl)-6-isopropyl-3-{(S)-1-[4-(1-methyl-1H-benzo[d]imidazol-5-yl)phenyl]ethyl}-1,3-oxazinan-2-one

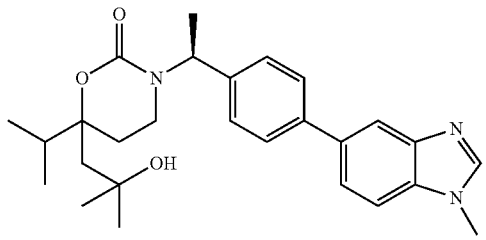 [SMILES: CC(C)C1(CC(C)(C)O)CCN([C@@H](C)c2ccc(-c3ccc4c(c3)ncn4C)cc2)C(=O)O1]

5-Bromo-1-methyl-1H-benzoimidazole was employed as the coupling partner.

$^1$H NMR ($CD_3OD$) 0.77 (d, 3H), 0.88 (d, 3H), 1.15-1.25 (6H), 1.55 (d, 3H), 1.60-1.90 (3H), 2.07 (m, 1H), 2.15 (m, 1H), 2.74 (2H), 4.08 (s, 3H), 5.58 (q, 1H), 7.40 (d, 2H), 7.64 (d, 2H), 7.87 (m, 2H), 7.94 (s, 1H), 9.28 (s, 1H); Mass spectrum (ESI$^+$): m/z=450 [M+H]±.

Biological Test Example 1

In vitro inhibition of 11 β-HSD1 by test compounds was determined with HTRF (Homogeneous Time-Resolved Fluorescence) technology (cisbio international, France) detecting cortisol generated from cortisterone by human liver microsomes. Briefly, compounds were incubated for 1 hour at 37° C. in Tris buffer (20 mM tris, 5 mM EDTA, pH 6.0) containing NADPH (200 μM) and cortisone (80 nM). Cortisol generated in the reaction is then detected with a competitive immunoassay, involving two HTRF conjugates: cortisol linked to XL665 and anti-cortisol antibody labeled with Europium cryptate. The incubation period for detection reaction was typically 2 hours. The amount of cortisol is determined by reading the time-resolved fluorescence of the wells (Ex 320/75 nm; Em 615/8.5 nm and 665/7.5 nm). The ratio of the two emission signals is then calculated (Em665*10000/Em615). Each assay contained incubations with vehicle controls instead of compound as controls for non-inhibited cortisol generation (100% CTL; 'high values') and incubations with carbenoxolone as controls for fully inhibited enzyme and cortisol background (0% CTL; 'low values'). Each assay also contained a calibration curve with cortisol to transform the fluorescent data into cortisol concentrations. Percent inhibition of each compound was determined relative to the carbenoxolone signal.

In Table 1 the 11β-HSD 1 inhibitory activities, determined as described above, are compiled, wherein 100% indicates no inhibition and a value of zero or below zero indicates complete inhibition.

TABLE 1

| Example | Average % control inhibition at 100 nM |
|---------|----------------------------------------|
| 1 | 14 |
| 2 | 63 |
| 3 | −3 |
| 4 | 3 |
| 5 | −5 |
| 6 | −19 |
| 7 | 10 |
| 8 | 9 |
| 9 | −14 |
| 10 | 17 |
| 11 | 43 |
| 12 | 59 |
| 13 | 58 |
| 14 | 15 |
| 15 | −34 |
| 16 | −24 |
| 17 | −10 |
| 18 | 93 |
| 19 | −1 |
| 20 | −13 |
| 21 | 97 |
| 22 | 17 |
| 23 | 44 |
| 24 | 53 |
| 25 | 71 |
| 26 | 80 |
| 27 | 86 |
| 28 | 34 |
| 29 | 23 |
| 30 | 28 |
| 31 | 88 |
| 33 | −27* |
| 34 | −17* |
| 35 | 1 |
| 36 | 31 |

*Average % control inhibition refers to 1 μM inhibitor concentration

Biological Test Example 2

The inhibition of a microsomal preparation of 11β-HSD1 by compounds of the invention was measured essentially as previously described (K. Solly, S. S. Mundt, H. J. Zokian, G. J. Ding, A. Hermanowski-Vosatka, B. Strulovici, and W. Zheng, High-Throughput Screening of 11-Beta-Hydroxyseroid Dehydrogenase Type 1 in Scintillation Proximity Assay Format. Assay Drug Dev Technol 3 (2005) 377-384). All reactions were carried out at rt in 96 well clear flexible PET Microbeta plates (PerkinElmer). The assay begins by dispensing 49 μl of substrate solution (50 mM HEPES, pH 7.4, 100 mM KCl, 5 mM NaCl, 2 mM MgCl$_2$, 2 mM NADPH and 160 nM [$^3$H]cortisone (1 Ci/mmol)) and mixing in 1 μL of the test compounds in DMSO previously diluted in half-log increments (8 points) starting at 0.1 mM. After a 10 minute pre-incubation, 50 μL of enzyme solution containing microsomes isolated from CHO cells overexpressing human 11β-HSD1 (10-20 μg/ml of total protein) was added, and the plates were incubated for 90 minutes at rt. The reaction was stopped by adding 50 μL of the SPA beads suspension containing 10 μM 18-β-glycyrrhetinic acid 5 mg/ml protein A coated YSi SPA beads (GE Healthcare) and 3.3 μg/ml of anti-cortisol antibody (East Coast Biologics) in Superblock buffer (Bio-Rad). The plates were shaken for 120 minutes at rt, and the SPA signal corresponding to [$^3$H]cortisol was measured on a Microbeta plate reader.

TABLE 2

11β-HSD 1 inhibitory activities of compounds of the invention determined as described above.

| Example | IC$_{50}$ |
|---|---|
| 37 | 6.9 nM |
| 38 | 7.7 nM |

The compounds of the invention are useful for ameliorating or treating disorders or diseases in which decreasing the level of cortisol is effective in treating a disease state. Thus, the compounds of the invention can be used in the treatment or prevention of diabetes mellitus, obesity, symptoms of metabolic syndrome, glucose intolerance, hyperglycemica, hypertension, hyperlipidemia, insulin resistance, cardiovascular disease, dyslipidemia, atherosclerosis, lipodystrophy, osteoporosis, glaucoma, Cushing's syndrome, Addison's Disease, visceral fat obesity associated with glucocorticoid therapy, depression, anxiety, Alzheimer's disease, dementia, cognitive decline (including age-related cognitive decline), polycystic ovarian syndrome, infertility and hypergonadism. The compounds of the invention can be used as therapeutic agents for pseudo Cushing's Syndrome associated with alcoholic liver disease. In addition, the compounds modulate the function of B and T cells of the immune system and can therefore be used to treat diseases such as tuberculosis, leprosy and psoriasis. They can also be used to promote wound healing, particularly in diabetic patients.

Additional diseases or disorders that are related to 11β-HSD1 activity include those selected from the group consisting of lipid disorders, hypretriglyceridemia, hypercholesterolemia, low HDL levels, high LDL levels, vascular restenosis, pancreatitis, abdominal obesity, neurodegenerative disease, retinopathy, nephropathy, neuropathy, diabetes, coronary heart disease, stroke, peripheral vascular disease, Cushing's syndrome, hyperinsulinemia, viral diseases, and Syndrome X. A further disease related to 11β-HSD1 activity is pseudo Cushing's Syndrome associated with alcoholic liver disease.

A pharmaceutical composition of the invention may, alternatively or in addition to a compound of Formula I, comprise a pharmaceutically acceptable salt of a compound of Formula I or a prodrug or pharmaceutically active metabolite of such a compound or salt and one or more pharmaceutically acceptable carriers therefore. Alternatively, a pharmaceutical composition of the invention may comprise a compound of Formula I, Ia-1 or a pharmaceutical salt thereof as the only pharmaceutically active agent in the pharmaceutical composition. The disclosed 11β-HSD1 inhibitors can be used alone or in a combination therapy with one or more additional agents for the treatment of diabetes, dyslipidemia, cardiovascular disease, hypertension, obesity, cancer or glaucoma.

The compositions of the invention are 11β-HSD1 inhibitors. Said compositions contain compounds having a mean inhibition constant (IC$_{50}$) against 11β-HSD1 of below about 1,000 nM; preferably below about 100 nM; more preferably below about 50 nM; even more preferably below about 5 nM; and most preferably below about 1 nM.

The invention includes a therapeutic method for treating or ameliorating an 11β-HSD1 mediated disorder in a subject in need thereof comprising administering to a subject in need thereof an effective amount of a compound of Formula I, or an enantiomer, diastereomer, or pharmaceutically acceptable salt thereof of composition thereof. As used herein, "treating" or "treatment" includes both therapeutic and prophylactic treatment. Therapeutic treatment includes reducing the symptoms associated with a disease or condition and/or increasing the longevity of a subject with the disease or condition. Prophylactic treatment includes delaying the onset of a disease or condition in a subject at risk of developing the disease or condition or reducing the likelihood that a subject will then develop the disease or condition in a subject that is at risk for developing the disease or condition.

An embodiment of the invention includes administering an 11β-HSD1 inhibiting compound of Formula I or composition thereof in a combination therapy with one or more additional agents for the treatment of diabetes, dyslipidemia, cardiovascular disease, hypertension, obesity, cancer or glaucoma. Agents for the treatment of diabetes include insulins, such as Humulin® (Eli Lilly), Lantus® (Sanofi Aventis), Novolin (Novo Nordisk), and Exubera® (Pfizer); PPAR gamma agonists, such as Avandia® (rosiglitizone maleate, GSK) and Actos® (pioglitazone hydrochloride, Takeda/Eli Lilly); sulfonylureas, such as Amaryl® (glimepiride, Sanofi Aventis), Diabeta® (glyburide, Sanofi Aventis), Micronase®/Glynase® (glyburide, Pfizer), and Glucotrol®/Glucotrol XL® and (glipizide, Pfizer); meglitinides, such as Prandin®/NovoNorm® (repaglinide, Novo Nordisk), Starlix® (nateglinide, Novartis), and Glufast® (mitiglinide, Takeda); biguanides, such as Glucophase®/Glucophase XR® (metformin HCl, Bristol Myers Squibb) and Glumetza (metformin HCl, Depomed); thiazolidinediones; amylin analogs, GLP-1 analogs; DPP-IV inhibitors; PTB-1B inhibitors; protein kinase inhibitors (including AMP-activated protein kinase inhibitors); glucagon antagonists, glycogen synthase kinase-3 beta inhibitors; glucose-6-phoshatase inhibitors; glycogen phosphorylase inhibitors; sodium glucose co-transporter inhibitors, and alpha-glucosidase inhibitors, such as Precose®/Glucobay®/Prandase®/Glucor® (acarbose, Bayer) and Glyset® (miglitol, Pfizer). Agents for the treatment of dyslipidemia and cardiovascular disease include statins, fibrates, and ezetimbe. Agents for the treatment of hypertension include alpha-blockers, beta-blockers, calcium channel blockers, diuretics, angiotensin converting enzyme (ACE) inhibitors, dual ACE and neutral endopeptidase (NEP) inhibitors, angiotensin-receptor blockers (ARBs), aldosterone synthase inhibitors, aldosterone-receptor antagonists, or endothelin receptor antagonist. Agents for the treatment of obesity include orlistat, phentermine, sibutramine and rimonabant.

An embodiment of the invention includes administering an 11β-HSD1 inhibiting compound of Formula I or composition thereof in a combination therapy with one or more other 11β-HSD1 inhibitors (whether such inhibitors are also compounds of Formula I or are compounds of a different class/genus), or with combination products, such as Avandamet® (metformin HCl and rosiglitazone maleate, GSK); Avandaryl® (glimepiride and rosiglitazone maleate, GSK);

Metaglip® (glipizide and metformin HCl, Bristol Myers Squibb); and Glucovance® (glyburide and metformin HCl, Bristol Myers Squibb).

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Additionally, the compounds of the present invention can be administered intranasally or transdermally. It will be obvious to those skilled in the art that the following dosage forms may comprise as the active ingredient, either compounds or a corresponding pharmaceutically acceptable salt of a compound of the present invention.

For preparing pharmaceutical compositions from the compounds of the present invention, pharmaceutically acceptable carriers can either be solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material. In powders, the carrier is a finely divided solid which is in a mixture with the finely divided active ingredient.

In tablets, the active ingredient is mixed with the carrier having the necessary binding properties in suitable proportions and compacted in the shape and size desired.

The powders and tablets preferably contain from about one to about seventy percent of the active ingredient. Suitable carriers are magnesium carbonate, magnesium stearate, talc, sugar, lactose, pectin, dextrin, starch, gelatin, tragacanth, methylcellulose, sodium caboxymethylcellulose, a low-melting wax, cocoa butter, and the like. Tablets, powders, cachets, lozenges, fast-melt strips, capsules and pills can be used as solid dosage forms containing the active ingredient suitable for oral administration.

For preparing suppositories, a low-melting wax, such as a mixture of fatty acid glycerides or cocoa butter, is first-melted and the active ingredient is dispersed homogeneously therein, as by stirring. The molten homogeneous mixture is then poured into convenient sized molds, allowed to cool, and thereby to solidify.

Liquid form preparations include solutions, suspensions, retention enemas, and emulsions, for example, water or water propylene glycol solutions. For parenteral injection, liquid preparations can be formulated in solution in aqueous polyethylene glycol solution.

Aqueous solutions suitable for oral administration can be prepared by dissolving the active ingredient in water and adding suitable colorants, flavors, stabilizing, and thickening agents as desired. Aqueous suspensions for oral administration can be prepared by dispersing the finely divided active ingredient in water with viscous material, such as natural or synthetic gums, resins, methylcellulose, sodium carboxymethylcellulose, and other well-known suspending agents.

The pharmaceutical composition is preferably in unit dosage form. In such form, the composition is subdivided into unit doses containing appropriate quantities of the active ingredient. The unit dosage form can be a packaged preparation, the package containing discrete quantities of, for example, tablets, powders, and capsules in vials or ampules. Also, the unit dosage form can be a tablet, cachet, capsule, or lozenge itself, or it can be the appropriate amount of any of these in packaged form.

The quantity of active ingredient in a unit dose preparation may be varied or adjusted from about 0.1 mg to about 1000.0 mg, preferably from about 0.1 mg to about 100 mg. The dosages, however, may be varied depending upon the requirements of the patient, the severity of the condition being treated, and the compound being employed. Determination of the proper dosage for a particular situation is within the skill in the art. Also, the pharmaceutical composition may contain, if desired, other compatible therapeutic agents.

In therapeutic treatment or as a method-of-use as an inhibitor of 11β-HSD1 or an inhibitor in the production of cortisol in the cell, the active ingredient is preferably administered orally in a solid dosage form as disclosed above in an amount of about 0.1 mg to about 100 mg per daily dose where the dose is administered once or more than once daily.

All publications, patents and patent applications mentioned in this specification are herein incorporated by reference to the same extent as if each individual publication or patent application were specifically and individually designated as having been incorporated by reference. It is understood that the examples and embodiments described herein are for illustrative purposes only, and it will be appreciated that the invention is susceptible to modification, variation and change without departing from the proper scope or fair meaning of the appended claims.

What is claimed is:

1. A compound represented by one of the following structural formulas:

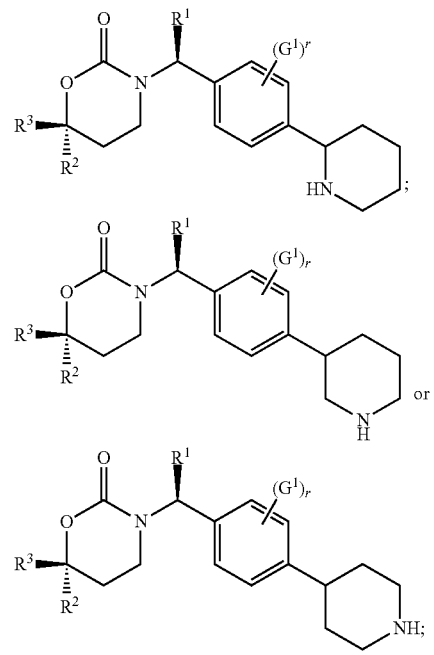

wherein:

$R^1$ is (a) absent or (b) is selected from $(C_1-C_6)$alkyl, $(C_2-C_6)$alkenyl, $(C_2-C_6)$alkynyl, $(C_1-C_3)$alkoxy$(C_1-C_3)$alkoxy, and $(C_1-C_3)$alkoxy$(C_1-C_3)$alkyl and is optionally substituted with up to four groups independently selected from fluorine, cyano, oxo, $R^4$, $R^4O$—, $(R^4)_2N$—, $R^4O_2C$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$—, $(R^4O)_2P(=O)O$—, $(R^4O)_2P(=O)NR^4$—, $R^4OS(=O)_2NR^4$—, $(R^4)_2NS(=O)_2O$—, $(R^4)_2NS(=O)_2NR^4$—, $R^4S(=O)_2NR^4$—, $R^4S(=O)_2NHC(=O)$—, $R^4S(=O)_2NHC(=O)O$—, $R^4S(=O)_2NHC(=O)NR^4$—, $R^4OS(=O)_2NHC$ (=O)—, $R^4OS(=O)_2NHC(=O)O$—, $R^4OS(=O)_2$ $NHC(=O)NR^4$—, $(R^4)_2NS(=O)_2NHC(=O)$—, $(R^4)_2NS(=O)_2NHC(=O)O$—, $(R^4)_2NS(=O)_2NHC(=O)NR^4$—, $R^4C(=O)NHS(=O)_2$—, $R^4C(=O)NHS(=O)_2O$—, $R^4C(=O)NHS(=O)_2NR^4$—, $R^4OC(=O)NHS(=O)_2$—, $R^4OC(=O)NHS(=O)_2O$—, $R^4OC(=O)NHS(=O)_2NR^4$—, $(R^4)_2NC(=O)NHS(=O)_2$—, $(R^4)_2NC(=O)NHS(=O)_2O$—, $(R^4)_2NC(=O)NHS(=O)_2NR^4$—, heterocyclyl, heteroaryl, arylamino and heteroarylamino;

$R^2$ is $(C_1-C_6)$alkyl, aryl, heteroaryl, cycloalkyl or heterocyclyl and is optionally substituted with up to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylthio, $(C_4-C_7)$cycloalkylalkylthio, halo$(C_1-C_6)$alkylthio, halo$(C_3-C_6)$cycloalkylthio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cycloalkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclylsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxy, $(C_1-C_6)$alkylcarbonyl, $(C_3-C_6)$cycloalkylcarbonyl, $(C_3-C_6)$cycloalkylaminocarbonyl, $\{(C_3-C_6)$cycloalkyl$\}\{(C_1-C_6)$alkyl$\}$aminocarbonyl, di$(C_3-C_6)$cycloalkylaminocarbonyl, $(C_3-C_6)$cycloalkylaminosulfonyl, $\{(C_3-C_6)$cycloalkyl$\}\{(C_1-C_6)$alkyl$\}$aminosulfonyl, di$(C_3-C_6)$cycloalkylaminosulfonyl, cyano$(C_1-C_6)$alkyl, aminocarbonyl$(C_1-C_6)$alkyl, $(C_1-C_6)$alkylaminocarbonyl$(C_1-C_6)$alkyl, di$(C_1-C_6)$alkylaminocarbonyl$(C_1-C_6)$alkyl, $(C_3-C_6)$cycloalkylaminocarbonyl$(C_1-C_6)$alkyl, $\{(C_3-C_6)$cycloalkyl$\}\{(C_1-C_6)$alkyl$\}$aminocarbonyl$(C_1-C_6)$alkyl and di$(C_3-C_6)$cycloalkylaminocarbonyl$(C_1-C_6)$alkyl;

$R^3$ is selected from $(C_1-C_6)$alkyl, $(C_2-C_6)$alkenyl, $(C_2-C_6)$alkynyl, $(C_3-C_5)$cycloalkyl$(C_1-C_4)$alkyl, $(C_1-C_3)$alkoxy $(C_1-C_3)$alkoxy, and $(C_1-C_3)$alkoxy$(C_1-C_3)$alkyl and is optionally substituted with up to four groups independently selected from fluorine, cyano, oxo, $R^4$, $R^4O$—, $(R^4)_2N$—, $R^4O_2C$—, $R^4C(=O)O$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$—, $(R^{4O})_2P(=O)O$—, $(R^4O)_2P(=O)NR^4$—, $R^4OS(=O)_2NR^4$—, $(R^4)_2NS(=O)_2O$—, $(R^4)_2NS(=O)_2NR^4$—, $R^4S(=O)_2NR^4$—, $R^4S(=O)_2NHC(=O)$—, $R^4S(=O)_2NHC(=O)O$—, $R^4S(=O)_2NHC(=O)NR^4$—, $R^4OS(=O)_2NHC(=O)$—, $R^4OS(=O)_2NHC(=O)O$—, $R^4OS(=O)_2NHC(=O)NR^4$—, $(R^4)_2NS(=O)_2NHC(=O)$—, $(R^4)_2NS(=O)_2NHC(=O)O$—, $(R^4)_2NS(=O)_2NHC(=O)NR^4$—, $R^4C(=O)NHS(=O)_2$—, $R^4C(=O)NHS(=O)_2O$—, $R^4C(=O)NHS(=O)_2NR^4$—, $R^4OC(=O)NHS(=O)_2$—, $R^4OC(=O)NHS(=O)_2O$—, $R^4OC(=O)NHS(=O)_2NR^4$—, $(R^4)_2NC(=O)NHS(=O)_2$—, $(R^4)_2NC(=O)NHS(=O)_2O$—, $(R^4)_2NC(=O)NHS(=O)_2NR^4$—, spirocycloalkyl; heterocyclyl (which in turn may be optionally substituted with alkyl, haloalkyl, halogen or oxo), heteroaryl (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo), arylamino (which in turn may be optionally substituted with alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido) and heteroarylamino (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo);

$R^4$ is independently selected from H, $(C_1-C_6)$alkyl, halo$(C_1-C_6)$alkyl, amino$(C_1-C_6)$alkyl, $(C_1-C_6)$alkylamino$(C_1-C_6)$alkyl, di$(C_1-C_6)$alkylamino$(C_1-C_6)$alkyl, hydroxy$(C_1-C_6)$alkyl and $(C_1-C_6)$alkoxy$(C_1-C_6)$alkyl;

each substitutable ring nitrogen atom in the piperidinyl ring is optionally substituted with $(C_1-C_4)$alkyl, $(C_1-C_4)$alkylcarbonyl, $CONH_2$, $(C_1-C_4)$alkylaminocarbonyl or di$(C_1-C_4)$alkylaminocarbonyl; wherein each substitutable ring carbon atom in the piperidinyl ring is optionally substituted with fluorine, chlorine, cyano, hydroxy, amino, $(C_1-C_4)$alkyl, $(C_3-C_4)$cycloalkyl, $(C_3-C_4)$cycloalkyl$(C_1-C_2)$alkyl, halo$(C_1-C_4)$alkyl, $(C_1-C_4)$alkoxy, $(C_1-C_4)$haloalkoxy, $CONH_2$, $(C_1-C_4)$alkylcarbonyl, $(C_1-C_4)$alkoxycarbonyl, $(C_1-C_4)$alkylaminocarbonyl, di$(C_1-C_4)$alkylaminocarbonyl or $(C_1-C_4)$alkylcarbonylamino;

each $G^1$ is independently halogen, cyano, oxo, nitro, hydroxy, amino, $(C_1-C_4)$alkyl, $(C_3-C_4)$cycloalkyl, $(C_3-C_4)$cycloalkyl$(C_1-C_2)$alkyl, halo$(C_1-C_4)$alkyl, $(C_1-C_4)$alkoxy, $(C_1-C_4)$haloalkoxy, $(C_1-C_4)$alkoxycarbonyl, benzoxycarbony, $CONH_2$, $(C_1-C_4)$alkylaminocarbonyl, di$(C_1-C_4)$alkylaminocarbonyl, $(C_3-C_4)$cycloalkylaminocarbonyl, $\{(C_1-C_4)$alkyl$\}\{(C_3-C_4)$cycloalkyl$\}$aminocarbonyl or $(C_1-C_4)$alkylcarbonylamino; and r is 0, 1 or 2;

or a pharmaceutically acceptable salt, enantiomer or diastereomer thereof.

2. The compound of claim 1, wherein the compound is represented by one of the following structural formulas:

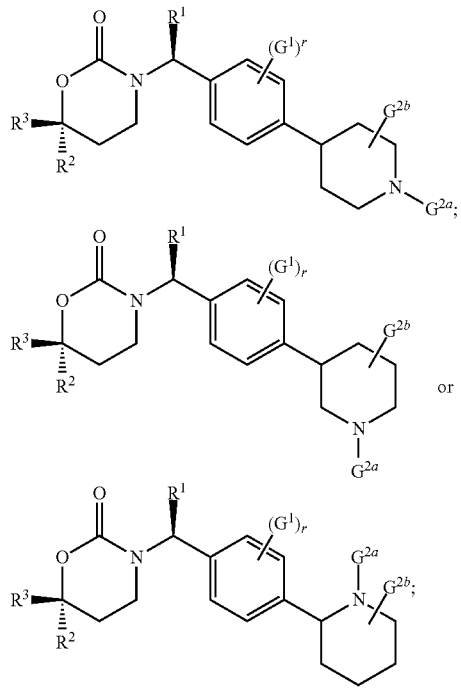

wherein
each $G^1$ is independently $(C_1$-$C_4)$alkyl, $(C_1$-$C_4)$alkoxy, $(C_1$-$C_4)$haloalkyl, $(C_1$-$C_4)$haloalkoxy, halogen, cyano or nitro;
r is 0, 1 or 2;
$G^{2a}$ is $(C_1$-$C_4)$alkyl, $(C_1$-$C_4)$alkylcarbonyl, or $(C_1$-$C_4)$alkoxycarbonyl; and
each $G^{2b}$ is independently hydrogen, fluorine, chlorine, cyano, hydroxy, amino, $(C_1$-$C_4)$alkyl, $(C_3$-$C_4)$cycloalkyl, $(C_3$-$C_4)$cycloalkyl$(C_1$-$C_2)$alkyl, halo$(C_1$-$C_4)$alkyl, $(C_1$-$C_4)$alkoxy, $(C_1$-$C_4)$alkylcarbonyl, $(C_1$-$C_4)$alkoxycarbonyl, $(C_1$-$C_4)$haloalkoxy, $CONH_2$, $(C_1$-$C_4)$alkylaminocarbonyl, di$(C_1$-$C_4)$alkylaminocarbonyl or $(C_1$-$C_4)$alkylcarbonylamino;
or a pharmaceutically acceptable salt, enantiomer or diastereomer thereof.

3. The compound of claim 1, wherein
$R^2$ is phenyl, thienyl, or pyridyl, each optionally substituted with halogen, nitro, cyano, $(C_1$-$C_6)$alkyl, halo$(C_1$-$C_6)$alkyl, hydroxy$(C_1$-$C_3)$alkyl, $(C_1$-$C_3)$alkoxy, halo$(C_1$-$C_3)$alkoxy, $CONH_2$ or $SO_2Me$; and
$R^3$ is methyl, ethyl, propyl, butyl, vinyl, allyl, propenylmethyl or ethoxyethyl each optionally substituted with up to two groups independently selected from $(C_1$-$C_4)$alkyl, $(C_1$-$C_4)$alkoxy, $(C_1$-$C_4)$alkoxycarbonyl, hydroxy$(C_1$-$C_4)$alkyl, cyano$(C_1$-$C_4)$alkyl, $(C_1$-$C_4)$haloalkyl, $(C_1$-$C_4)$haloalkoxy, $(C_1$-$C_4)$alkylamino, di$(C_1$-$C_4)$alkylamino, halogen, cyano, oxo, nitro, hydroxy, amino, $MeSO_2$—, $MeSO_2N(Me)(C_1$-$C_4)$alkyl, $MeSO_2NH(C_1$-$C_4)$alkyl, $H_2NC(=O)CMe_2(C_1$-$C_4)$alkyl, $H_2NC(=O)CHMe(C_1$-$C_4)$alkyl and $H_2NC(=O)CH_2(C_1$-$C_4)$alkyl.

4. The compound of claim 1, wherein $R^1$ is methyl or ethyl.

5. A pharmaceutical composition comprising: i) a pharmaceutically acceptable carrier or diluent; and ii) the compound of claim 1; or a pharmaceutically acceptable salt, enantiomer or diastereomer thereof.

6. A method of treating a subject with a disease or disorder selected from diabetes mellitus, obesity, symptoms of metabolic syndrome, glucose intolerance, hyperglycemia, hypertension, hyperlipidemia, insulin resistance, cardiovascular disease, dyslipidemia, atherosclerosis, lipodystrophy, osteoporosis, glaucoma, Cushing's syndrome, Addison's Disease, visceral fat obesity associated with glucocorticoid therapy, depression, anxiety, Alzheimer's disease, dementia, cognitive decline, polycystic ovarian syndrome, infertility, hypergonadism, tuberculosis, leprosy, psoriasis, wound healing, lipid disorders, hypertriglyceridemia, hypercholesterolemia, low HDL levels, high LDL levels, vascular restenosis, pancreatitis, abdominal obesity, neurodegenerative disease, retinopathy, nephropathy, neuropathy, coronary heart disease, stroke, peripheral vascular disease, hyperinsulinemia, viral diseases, and Syndrome X, comprising the step of administering to the subject an effective amount of the compound of claim 1.

\* \* \* \* \*